(12) United States Patent
Chaudry et al.

(10) Patent No.: US 9,301,970 B2
(45) Date of Patent: Apr. 5, 2016

(54) METHODS AND COMPOSITIONS FOR TREATING TRAUMA-HEMORRHAGE USING ESTROGEN AND DERIVATIVES THEREOF

(75) Inventors: Irshad H. Chaudry, Vestavia Hills, AL (US); William J. Hubbard, Hoover, AL (US); Zheng Feng Ba, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 574 days.

(21) Appl. No.: 12/706,584

(22) Filed: Feb. 16, 2010

(65) Prior Publication Data

US 2011/0021981 A1    Jan. 27, 2011

Related U.S. Application Data

(63) Continuation of application No. 11/748,453, filed on May 14, 2007, now abandoned.

(60) Provisional application No. 60/802,352, filed on May 22, 2006.

(51) Int. Cl.
  *A61K 31/565* (2006.01)
  *A61K 31/721* (2006.01)
  *A61K 31/56* (2006.01)

(52) U.S. Cl.
  CPC ............. *A61K 31/721* (2013.01); *A61K 31/56* (2013.01); *A61K 31/565* (2013.01); *C12N 2501/392* (2013.01)

(58) Field of Classification Search
  CPC ... A61K 31/565; A61K 31/57; C07K 5/0005; C07K 1/0066; C07K 1/007
  See application file for complete search history.

(56) References Cited

U.S. PATENT DOCUMENTS

| | | | | |
|---|---|---|---|---|
| 5,798,338 A * | 8/1998 | Backensfeld et al. | ...... | 514/26 |
| 6,011,023 A * | 1/2000 | Clark et al. | ...... | 514/171 |
| 6,326,365 B1 | 12/2001 | Simpkins | ...... | 514/179 |
| 6,339,078 B1 * | 1/2002 | Simpkins et al. | ...... | 514/179 |
| 6,350,739 B1 | 2/2002 | Simpkins | ...... | 514/182 |
| 7,163,931 B2 | 1/2007 | Backensfeld | ...... | 514/58 |
| 2007/0254329 A1 | 11/2007 | Rubin | ...... | 435/29 |
| 2007/0287684 A1 | 12/2007 | Chaudry | ...... | 514/58 |
| 2011/0021981 A1 | 1/2011 | Chaudry | ...... | 514/58 |

FOREIGN PATENT DOCUMENTS

| WO | WO 98/22113 | | 5/1998 |
|---|---|---|---|
| WO | WO 01/68074 | * | 9/2001 |
| WO | WO 2013/172969 | | 11/2013 |

OTHER PUBLICATIONS

Chu et al., "Transport of Ethinylestradiol Glucuronide and Ethinylestradiol Sulfate by the Multidrug Resistance Proteins MRP1, MRP2, and MRP3" The Journal of Pharmacology and Experimental Therapeutics (2004) vol. 309 pp. 156-164.*

Qian et al., "Targeted Disruption of the Mouse Estrogen Sulfotransferase Gene Reveals a Role of Estrogen Metabolism in Intracrine and Paracrine Estrogen Regulation" Endocrinology (2001) vol. 142 No. 12 pp. 5342-5350.*

Knoferl et al., "no Female Sex Steroids Adversely or Beneficially Affect the Depressed Immune Responses in Males After Trauma-Hemorrhage?" Archives of Surgery (2000) vol. 135 pp. 425-433.*

Kuebler et al., "Estradiol Administration Improves Splanchnic Perfusion Following Trauma-Hemorrhage and Sepsis" Archives of Surgery (2002) vol. 137 pp. 74-79.*

Shafi et al., "Fluid Resuscitation and Blood Replacement in Patients with Polytrauma" Clinical Orthopaedics and Related Research (2004) vol. 422 pp. 37-42.*

Stern et al., "Low-volume Fluid resuscitation for presumed hemorrhagic shock: helpful or harmful?" Current Opinion in Critical Care (2001) vol. 7 pp. 422-430.*

FDA label for Premarin® intravenous, conjugated estrogens for injection, published Jan. 2005, pp. 1-17, downloaded from www.fda.gov.*

Miller et al., "Efficacy of 17-alpha-ethynylestradiol-3-sulfate for severe hemorrhage in minipigs in the absence of fluid resuscitation" J Trauma Acute Care Surg (2014) vol. 76 No. 6 pp. 1409-1416.*

Hubbard et al., "17-alpha-ethynylestradiol-3-sulfate treatment of severe blood loss in rats" Jurnal of Surgical Research (2015) vol. 193 pp. 355-360.*

Ahmed, Simi T., et al., "Inhibition of IL-6 and IL-10 signaling and stat activation by inflammatory and stress pathways," J. Immunol. 165, 5227-5237 (2000).

Angele, Martin K., et al., "Testosterone receptor blockade following hemorrhage in males: Restoration of the depressed immune functions and improved survival after subsequent sepsis." Arch Surg 132, 1207-1214 (1997).

Angele, Martin K., et al., "Effects of gender and sex hormones on the immune response following trauma—potential clinical applications," Shock 25, Supplement 1:11 Abstract 34 (2006).

Angele, Martin K., et al., "Gender dimorphism in trauma-hemorrhage-induced thymocyte apoptosis," Shock 12, 316-322 (1999).

Angele, Martin K., et al., "L-arginine restores the depressed cardiac output and regional perfusion after trauma-hemorrhage," Surgery 124, 394-401 (1998).

Angele, Martin K., et al., "Sex steroids regulate pro- and anti-inflammatory cytokine release by macrophages after trauma-hemorrhage," Am J Physiol, 277, C35-C42 (1999).

Angele, Martin K., et al., "Testosterone and/or low estradiol: normally required but harmful immunologically for males after trauma-hemorrhage," J. Trauma 44, 78-85 (1998).

Ayala, Alfred, et al., "Defective macrophage antigen presentation following hemorrhage is associated with the loss of MHC class II (Ia) antigens," Immunology 70:33-39 (1990).

Ayala, Alfred, et al., "Differential effects of hemorrhage on Kupffer cells: decreased antigen presentation despite increased inflammatory cytokine (IL-1, IL-6 and TNF) release," Cytokine 4, 66-75 (1992).

Ayala, Alfred, et al., "Enhanced susceptibility to sepsis after simple hemorrhage: Depression of Fc and C3b receptor mediated phagocytosis," Arch Surg; 125, 70-75 (1990).

(Continued)

*Primary Examiner* — Eric Olson
(74) *Attorney, Agent, or Firm* — Ballard Spahr Andrews & Ingersoll, LLP; Scott D. Marty

(57) ABSTRACT

Disclosed are methods and materials for treating or preventing complications due to traumatic injuries using estrogen or derivatives thereof.

22 Claims, 42 Drawing Sheets

(56) References Cited

OTHER PUBLICATIONS

Ayala, Alfred, et al., "Hemorrhage induces enhanced Kupffer cell cytotoxicity while decreasing peritoneal or splenic macrophage capacity: involvement of cell-associated TNF and reactive nitrogen," J Immunol 147, 4147-4154 (1991).

Ayala, Alfred, et al., "Increased susceptibility to sepsis following hemorrhage: Defective Kupffer cell mediated antigen presentation," Surg Forum 40, 102-104 (1989).

Ayala, Alfred, et al., "Mechanism of enhanced susceptibility to sepsis after hemorrhage: Interleukin (IL)-10 suppression of T-cell response is mediated by eicosanoid induced IL-4 release," Arch Surg 129, 1172-1178 (1994).

Ayala, Alfred, et al., "Polymicrobial sepsis selectively activates peritoneal but not alveolar macrophage to release inflammatory mediators (IL-1, IL-6 and TNF)," Circ Shock 36, 191-199 (1992).

Ayub, A., et al., "17Beta-estradiol 3,17 disulfate improves physiological parameters in brain after traumatic brain injury," Shock (Suppl) 35:67 (2011) (Abstract).

Ayub, A., et al., "Estrogen-SO4 administration Post-TBI decreases intracranial pressure, increases partial brain O2 pressure and facilitates a faster return to normothermic brain temperature," ATACCC, Harbor Beach Resort, Fort Lauderdale FL, Aug. 16-17, 2011, NT32: 65.

Baker, C. C., et al., "Evaluation of factors affecting mortality rate after sepsis in murine cecal ligation and puncture model," Surgery 94, 331-335 (1983).

Balentine, J. D., "Hypotheses in spinal cord trauma research," In: Becker DP & Povlishock JT, (eds). Central Nervous System Trauma Status Report: NIH Bethesda Maryland. pp. 455-461 (1985).

Barton, R.G., et al., "Initial management of trauma. The first 5 minutes," Postgrad Med 88, 83-90 (1990).

Basso, D. M., et al., "A sensitive and reliable locomotor rating scale for open field testing in rats," J Neurotrauma, 12, 1-21(1995).

Baue, A. E., et al. "Systemic inflammatory response syndrome (SIRS), multiple organ dysfunction syndrome (MODS), multiple organ failure (MOF): are we winning the battle?" Shock. 10, 79-89 (1998).

Baumann, H., et al., "Stimulation of hepatic acute phase response by cytokines and glucocorticoids," Ann NY Acad Sci, 557:280-295 (1989).

Beckman, Joseph S., "Oxidative damage and tyrosine nitration from peroxynitrite," Chem Res Toxicol, 9, 866-844 (1996).

Beiche, F., et al., "Expression of cyclooxygenase isoforms in the rat spinal cord and their regulation during adjuvant-induced arthritis," Inflamm Res, 47: 482-487 (1998).

Blight, A. R., "Macrophages and inflammatory damage in spinal cord injury," J Neurotrauma 1: 83-91 (1992).

Bone, R. C., "Toward an epidemiology and natural history of SIRS (systemic inflammatory response syndrome)," JAMA 268, 3452-3455 (1992).

Bucci, M., et al. "17-β-oestradiol-induced vasorelaxation in vitro is mediated by eNOS through hsp90 and akt/pkb dependent mechanism," Br. J. Pharmacol. 135(7), 1695-700 (Apr. 2002).

Bynoe, Margaret S., et al. "Estrogen up-regulates Bcl-2 and blocks tolerance induction of naive B cells," Proc Natl Acad Sci USA, 97, 2703-2708 (2000).

Brown, C. M., et al., "Estradiol is a potent protective, restorative, and trophic factor after brain injury," Semin. Reprod. Med. 27(3), 240-49 (May 2009).

Caulin-Glaser, Teresa, et al., "17β-Estradiol regulation of human endothelial cell basal nitric oxide release, independent of cytosolic $Ca^{2+}$ mobilization," Circ Res, 81, 885-892 (1997).

Chaudry, et al., "The role of gender and sex steroids in influencing organ functions following trauma-hemorrhage," pp. 1-2, presented at a Cornell seminar on Sep. 15, 2002 and at Eli Lilly on Apr. 16, 2002.

Chaudry, I. H., et al., Immunological aspects of hemorrhage. Austin, TX: Medical Intelligence Unit; R.G. Landes Co.,1-132 (1992).

Chaudry, I. H., et al., "Rat and mouse models of hypovolemic-traumatic shock," In: Pathophysiology of Shock: Sepsis and Organ Failure, edited by Schlag G and Redl H. Berlin: Springer-Verlag, p. 371-383 (1993).

Chaudry, I. H., et al. "Hemorrhage and resuscitation: immunological aspects," Am J Physiol, 259, R663-R678 (1990).

Chen, J.G. , et al. "17beta-estradiol (E2) administration after major blood loss improves liver ATP, 3-hour survival and also long-term survival following prolonged hypotension (3-hour) and fluid resuscitation." Shock 25(Supp 1): 11 (2006) (Abstract).

Chen, Zhong, et al. "Estrogen receptor alpha mediates the nongenomic activation of endothelial nitric oxide synthase by estrogen," J Clin Invest, 103, 401-406 (1999).

Chittenden, Thomas, et al., "Induction of apoptosis by the Bcl-2 homologue Bak," Nature, 374, 733-736, (1995).

Cuzzocrea, Salvatore, et al., "17beta-estradiol anti-inflammatory activity in carrageenan-induced pleurisy," Endocrinology, 141: 1455-1463, (2000).

Deshpande, R, et al., "Estradiol down-regulates LPS-induced cytokine production and NF B activation in murine macrophages," Am J Reprod Immunol, 38, 46-54 (1997).

Diano, S., et al., "Aromatase and estrogen receptor immunoreactivity in the coronary arteries of monkeys and human subjects," Menopause; 6:21-28 (1999).

Diodato, M. D., Knöferl MW, Angele MK, Schwacha MG, Ci- offi WG, Bland KI, & Chaudry, I. H., "Females tolerate the deleterious consequences of hemorrhage better than males (Abstract)," Shock 11: 68 (1999).

Diodato, M. D., et al., "Gender differences in the inflammatory response and survival following hemorrhage and subsequent sepsis," Cytokine, 14, 162-169 (2000).

Douketis, J. D., et al., "The effects of hormone replacement therapy on thrombin generation, fibrinolysis inhibition, and resistance to activated protein C: prospective cohort study and review of literature," Thromb Res, 99, 25-34 (2000).

Dubal, Dena B., et al., "Estradiol modulates bcl-2 in cerebral ischemia: a potential role for estrogen receptors," J Neurosci, 19, 6385-6393 (1999).

Eachempati, Soumitra R., et al., "Gender-based differences in outcome in patients with sepsis," Arch Surg, 134, 1342-1347 (1999).

Echeverria, Olga M., et al., "Immuno-electron microscopic localization of estradiol receptor in cells of male and female reproductive and non-reproductive organs," Biol Cell; 81, 257-265 (1994).

Endoh, M., et al., "Expression of the inducible form of nitric oxide synthase by reactive astrocytes after transient global ischemia," Brain Res 651, 92-100 (1994).

Ertel, W., et al., "Biological significance of elevated TNF levels: in vivo administration of monoclonal antibody against TNF after haemorrhage shock increases the capacity of macrophages to release TNF while restoring immunoresponsiveness," Cytokine, 6, 624-632 (1994).

Ertel, W., et al., "Chloroquine attenuates hemorrhagic shock induced suppression of Kupffer cell antigen presentation and MHC class II antigen expression through blockade of tumor necrosis factor and prostaglandin release," Blood 78:1781-1788 (1991).

Escheverria, O. M., et al., "Immuno-electron microscopic localization of estradiol receptor in cells of male and female reproductive and non-reproductive organs," Biol. Cell, 81(3), 257-65 (1994).

Evans, M. J., et al. "Estrogen decreases in vitro apoptosis of peripheral blood mononuclear cells from women with normal menstrual cycles and decreases TNF-alpha production in SLE but not in normal cultures," Clin Immunol Immunopathol, 82, 258-262 (1997).

Everson, G. T., "Gastrointestinal motility in pregnancy," Gastroenterol Clin North Am, 21, 751-776 (1992).

Fraser, H, et al., "Enhancement of post-ischemic myocardial function by chronic 17b-estradiol treatment: role of alterations in glucose metabolism," J Mol Cell Cardiol, 31, 1539-1549 (1999).

Frazier-Jessen, M. R., et al., "Estrogen suppression of connective tissue deposition in a murine model of peritoneal adhesion formation," J Immunol, 156, 3036-3042 (1996).

Freay, A. D., et al., "Mechanism of vascular smooth muscle relaxation by estrogen in depolarized rat and mouse aorta. Role of nuclear estrogen receptor and Ca-1 uptake," Circ Res, 81, 242-248 (1997).

(56) References Cited

OTHER PUBLICATIONS

Genovese, T., et al., "Immunomodulatory effects of etanercept in an experimental model of spinal cord injury," J Pharmacol Exp Ther, 316, 1006-1016 (2005).
Genovese, T., et al., "Neuroprotection and enhanced recovery with hypericum perforatum extract after experimental spinal cord injury in mice," Shock, 25, 608-617 (2006).
Gohel, A., et al., "Estrogen prevents glucocorticoid-induced apoptosis in osteoblasts in vivo and in vitro," Endocrinology, 140, 5339-5347 (1999).
Gregory, M.S., et al. "Estrogen mediates the sex difference in post-burn immunosuppression." J Endocrinol 164:129-138 (2000).
Gulshan, S, et al., "Oestrogen receptors in macrophages," Scand J Immunol, 31, 691-697 (1990).
Harbrecht, B. G., et al , "Inhibition of nitric oxide synthase during hemorrhagic shock increases hepatic injury," Shock, 4, 332-337 (1995).
Hauptman, J., et al., "Improved methodology for the evaluation of the velocity of clearance of indocyanine green in the rat," Circ Shock, 33, 26-32 (1991).
Hauptman, J. G., et al. "Measurement of hepatocellular function, cardiac output, effective blood volume, and oxygen saturation in rats," Am J Physiol, 257, R439-R444 (1989).
Herson, P.S., et al. "Sex, sex steroids, and brain injury." Semin. Reprod. Med. 27(3): 229-39 (May 2009).
Hierholzer, C., et al., "Essential role of induced nitric oxide in the initiation of the inflammatory response after hemorrhagic shock," J Exp Med, 187, 917-928 (1998).
Hobbs, M. V., et al., "Patterns of cytokine gene expression by CD41 T cells from young and old mice," J Immunol, 150, 3602-3614 (1993).
Hofmann-Lehmann, R., et al., "Female cats have lower rates of apoptosis in peripheral blood lymphocytes than male cats: correlation with estradiol-17β, but not with progesterone blood levels," Vet Immunol Immunopathol, 65, 151-160 (1998).
Holcomb, J. B., et al., "Implications of new dry fibrin sealant technology for trauma surgery," Surg Clin North Am., 77(4), 943-52 (1997).
Homo-Delarche, F., et al., "Sex steroids, glucocorticoids, stress and autoimmunity," J. J. Steroid Biochem. Mol. Biol., 40, 619-637 (1991).
Howard, M. & O'Garra, A. "Biological properties of interleukin-10," Immunol Today, 13, 198-200 (1992).
Howard, M, et al., "Biological properties of interleukin 10," J Clin Immunol, 12, 239-247 (1992).
Hsu, C. Y., et al. "Vascular permeability in experimental spinal cord injury," J Neurol Sci, 70, 275-282 (1985).
Ihle, J. N., et al., "Phenotypic characteristics of cell lines requiring IL-3 for growth," J Immunol, 129, 1377-1383 (1982).
Jarrar, D, et al., "Organ dysfunction following hemorrhage and sepsis: mechanisms and therapeutic approaches," Int J Mol Med, 4, 575-583 (1999).
Jarrar, D, et al., "Insight into the mechanism by which estradiol improves organ functions after trauma-hemorrhage," Surgery, 128(2), 246-25 (2000).
Jarrar, D, et al., "Metoclopramide: a novel adjunct for improving cardiac and hepatocellular functions after trauma-hemorrhage," Am J Physiol Endocrinol Metab, 278, E90-E95 (2000).
Jarrar, D, et al., "The female reproductive cycle is an important variable in the response to trauma-hemorrhage and resuscitation [abstract]," Shock, 11(suppl1), 70 (1999).
Jarrar, D, et al., "The female reproductive cycle is an important variable in the response to trauma-hemorrhage," Am J Physiol Heart Circ Physiol, 279(3), H1015-H1021 (2000).
Joshi, M, et al., "Development and characterization of a novel, graded model of clip compressive spinal cord injury in the mouse: Part 1. Clip design, behavioral outcomes, and histopathology," J Neurotrauma, 19, 175-190 (2002a).
Joshi, M., et al., "Development and characterization of a novel, graded model of clip compressive spinal cord injury in the mouse: Part 2. Quantitative neuroanatomical assessment and analysis of the relationships between axonal tracts, residual tissue, and locomotor recovery," J Neurotrauma 19, 19 1-203 (2002b).
Kabadi, S.V., et al. "Fluid-percussion-induced traumatic brain injury model in rats." Nat. Protoc. 5(9): 1552-63 (Sep. 2010).
Kahlke, V., et al., "Gender and age are important factors that influence immune responses after trauma-hemorrhage (Abstract)," Shock 11, Suppl 1, 70 (1999).
Kahlke, V., et al., "Immune dysfunction following trauma-hemorrhage: influence of gender and age," Cytokine, 12, 69-77 (2000).
Kahlke, V., et al., "Reversal of sexual dimorphism in splenic T lymphocyte responses after trauma-hemorrhage with aging," Am J Physiol Cell Physiol, 278, C509-C516 (2000).
Karas, R. H. & Mendelsohn, M. E., "Rapid vasomotor effects of estrogen: men are part of the club," Chest 114: 1508-1509 (1998).
Kerger, H, et al., "Systemic and microcirculatory effects of autologous whole blood resuscitation in severe hemorrhagic shock," Am J Physiol Heart Circ Physiol, 276, H2035-H2043 (1999).
Kim, H, et al. "Single photon emission computed tomography demonstrated efficacy of 17-beta-estradiol therapy in male rats following trauma-hemorrhage and extended hypotension." J. Trauma 69: 1266-1273 (2010).
Kim, H, et al. "Blood-pool and gated-SPECT imaging confirms enhancement of cardiovascular function by 17-beta-estradiol (E2) following severe and prolonged hypotension even without fluid resuscitation in a rat model." J. Nuc. Med. 48(Suppl): 54 (2007).
Kitazawa, T., et al., "Non-genomic mechanism of 17β-oestradiol-induced inhibition of contraction in mammalian vascular smooth muscle," J Physiol (Lond), 499, 497-511 (1997).
Knöferl, M, et al., "17β-estradiol normalizes immune responses in ovariectomized females after trauma-hemorrhage," Am J Physiol Cell Physiol, 281, C1131-C1138 (2001).
Knöferl, M, et al., "Female sex hormones regulate macrophage function after trauma-hemorrhage and prevent increased death rate from subsequent sepsis," Ann Surg 235, 105-112 (2002).
Knöferl, M. W., et al., "Do female sex steroids adversely or beneficially affect the depressed immune responses in males after trauma-hemorrhage?" Arch Surg 135, 425-433 (2000).
Knöferl, MW, et al., "Surgical ovariectomy produces immunodepression following trauma-hemorrhage and increases mortality from subsequent sepsis," Surg Forum 50: 235-237 (1999).
Kowalenko, Terry, et al. 1992. "Improved outcome with hypotensive resuscitation of uncontrolled hemorrhagic shock in a swine model." J Trauma-Injury Infection & Critical Care.
Kozlov, AV, et al. "Effect of estrogen on mitochondrial function and intracellular stress markers in rat liver and kidney following trauma-hemorrhagic shock and prolonged hypotension." J. Mol. Med. 16(7-8), 254-261(2010).
Kuebler, Joachim F., et al., "Estradiol administration improves splanchnic perfusion following trauma-hemorrhage and sepsis," Arch Surg, vol. 137, 74-79 (2002).
LaFlamme, A. C., et al., "Role of IL-6 in directing the initial immune response to schistosome eggs," J Immunol, 164, 2419-2426 (2000).
Lantin-Hermoso, R. L., et al., "Estrogen acutely stimulates nitric oxide synthase activity in fetal pulmonary artery endothelium," Am J Physiol Lung Cell Mol Physiol, 273, L119-L126 (1997).
Lefer, A.M., "Endotoxin, cytokines, and nitric oxide in shock," Shock 1, 79-80 (1994).
Lindner, V., et al., "Increased expression of estrogen receptor-b mRNA in male blood vessels after vascular injury," Circ Res 83, 224-229 (1998).
Maegele, M., et al., "Characterization of a new rat model of experimental combined neurotrauma," Shock 23, 476-481, (2005).
Maier, B., et al., "Delayed elevation of soluble tumor necrosis factor receptors P75 and P55 in cerebrospinal fluid and plasma after traumatic brain injury," Shock, vol. 26(2), 122-127 (2006).
Matejuk, A., et al., "Estrogen treatment induces a novel population of regulatory cells, which suppresses experimental autoimmune encephalomyelitis," J Neurosci Res, 77, 119-126 (2004).
Matsuyama Y, Sato K, Kamiya M, Yano J, Iwata H, Isobe K: Nitric oxide: a possible etiologic factor in spinal cord cavitation. J Spinal Disord 11: 248-252 (1998).

(56) References Cited

OTHER PUBLICATIONS

McGowan, J. E., et a., "Bacteremia at Boston City Hospital: occurrence and mortality during 12 selected years (1935-972) with special reference to hospital-acquired cases," J Infect Dis 132, 316-335 (1975).

McLauchlan, G. J., et al., "Outcome of patients with abdominal sepsis treated in an intensive care unit," Br J Surg 82, 524-529 (1995).

McTigue, D. M., et al., "Localization of Transforming Growth Factor-β1 and Receptor mRNA after Experimental Spinal Cord Injury," Experimental Neurology, 163, 220-230 (2000).

McTigue, D. M., et al., "Strategies for spinal cord injury repair," Prog Brain Res 128, 3-8 (2000).

McTigue, J., "The complexities of treating shoulder pain," JAAPA, 13(12), 80-81 (2000).

McTigue, T., et al., "Efficacy of a Skin Tear Education Program," J Wound Ostomy Continence Nurs., 36(5), 486-492 (2009).

Meldrum, D. R., et al., "Diltiazem restores IL-2, IL-3, IL-6 and IFN-synthesis and decreases susceptibility to sepsis following hemorrhage," J Surg Res 51, 158-164 (1991).

Mendelsohn, M. E. & Karas, R. H., "The protective effects of estrogen on the cardiovascular system," N Engl J Med 340, 1801-1811 (1999).

Merrill, J. E., et al., "Microglial cell cytotoxicity of oligodendrocytes is mediated through nitric oxide," J Immunol, 151, 2132-2141 (1993).

Miller, R. A., "Cellular and biochemical changes in the aging mouse immune system," Nutr Rev 53, S8-S14 (1995).

Mizel, S. B. Production and quantitation of lymphocyte-activating factor (interleukin 1). In: Manual of Macrophage Methodology, edited by Herscowitz HB, Holden HT, Bellanti JA, and Ghaffar A. New York: Dekker, p. 407-441 (1981).

Mizushima, Y., et al., "Preinduction of heat shock proteins protects cardiac and hepatic functions following trauma and hemorrhage," Am J Physiol Regulatory Integrative Comp Physiol, 278, R352-R359 (2000).

Mizushima, Y., et al., "Estradiol administration after trauma-hemorrhage improves cardiovascular and hepatocellular functions in male animals," Ann Surg 232, 673-679 (2000).

Mossalayi, M. D., et al., "In vitro differentiation and proliferation of purified human thymic and bone marrow CD71 CD22 T-cell precursors," Exp Hematol 18, 326-331 (1990).

Mullane, K. M., et al., "Myeloperoxidase activity as a quantitative assessment of neutrophil infiltration into ischemic myocardium," J Pharmacol Meth 14, 157-167 (1985).

Nathan, L., et al., "Estradiol inhibits leukocyte adhesion and transendothelial migration in rabbits in vivo: possible mechanisms for gender differences in atherosclerosis," Circ Res 85, 377-385 (1999).

Nelson, H. D. "Commonly used types of postmenopausal estrogen for treatment of hot flashes: scientific review," JAMA. 291(13), 1610-20 (Apr. 2004).

Nesic-Taylor, O., et al., "Exogenous BclxL fusion protein spares neurons after spinal cord injury," J Neurosci Res 79, 628-637 (2005).

Noppens, R.R., et al. "Dose-dependent neuroprotection by 17beta-estradiol after cardiac arrest and cardiopulmonary resuscitation." Crit Care Med 33(7):1595-1602 (2005).

Offner, P. J., et al., "Male gender is a risk factor for major infections after surgery," Arch Surg, vol. 134, 935-940 (1999).

Ogle, T. F., et al., "Ovarian and adrenal steroids during pregnancy and the oestrous cycle in the rat," J Endocrinol 74, 89-98 (1977).

O'Neill, P. J., et al., "Role of Kupffer cells in interleukin-6 release following trauma-hemorrhage and resuscitation," Shock, 1(1), 43-7 (1994).

Palaszynski, K. M., et al., "Estriol treatment ameliorates disease in males with experimental autoimmune encephalomyelitis: implications for multiple sclerosis," J Neuroimmunol, 149, 84-89 (2004).

Papanicolaou, D. A., et al., "The pathophysiologic roles of interleukin-6 in human disease," Ann Intern Med, 128, 127-137 (1998).

Pepe, P. E., et al., "Prehospital fluid resuscitation of the patient with major trauma," Prehosp Emerg Care, 6(1), 81-91 (Jan.-Mar. 2002).

Pines, A., et al., "Effect of estradiol on rat ileum," Gen Pharmacol, 31, 735-736 (1998).

Popovich, P. G., et al., "Concept of autoimmunity following spinal cord injury: possible roles for T lymphocytes in the traumatized central nervous system," J Neurosci Res, 45, 349-363 (1996).

Purtilo, D. T., et al., "Depressed maternal lymphocyte response to phytohaemagglutinin in human pregnancy," Lancet 1, 769-771 (1972).

Qian, Y.M., et al., "Targeted disruption of the mouse estrogen sulfotransferase gene reveals a role of estrogen metabolism in intracrine and paracrine estrogen regulation," Endocrinology, 142(12), 5342-50 (2001).

Ramachandran, C., et al., "Estrogenic regulation of uterine 90-kilodalton heat shock protein," Endocrinology, 123, 956-961 (1988).

Ray, S. K., et al., "Inhibition of cysteine proteases in acute and chronic spinal cord injury," Neurotherapeutics. 8(2), 180-186 (Apr. 2011).

Remmers, D. E., et al., "Testosterone receptor blockade after trauma-hemorrhage improves cardiac and hepatic functions in males," Am J Physiol Heart Circ Physiol 273, H2919-H2925 (1997).

Remmers, D. E., et al., "Chronic resuscitation after trauma-hemorrhage and acute fluid replacement improves hepatocellular function and cardiac output," Ann Surg 227, 112-119 (1998).

Remmers, D. E., et al., "Testosterone: the crucial hormone responsible for depressing myocardial function in males after trauma—hemorrhage," Ann Surg 227, 790-799 (1998).

Robinson, D. A., et al., "Pentoxifylline restores the depressed cardiac performance after trauma-hemorrhage and resuscitation," J Surg Res 66, 51-56 (1996).

Rossouw, J. E., "Hormone replacement therapy and cardiovascular disease," Curr Opin Lipidol, 10, 429-434 (1999).

Sairanen, T., et al., "Cyclooxygenase-2 is induced globally in infarcted human brain," Ann Neurol 43, 738-747 (1998).

Samantaray, S., et al., "Neuroprotective efficacy of estrogen in experimental spinal cord injury in rats," Ann. N.Y. Acad. Sci., 1199, 90-94 (Jun. 2010).

Samy, T. S., et al., "Androgen and estrogen receptors in splenic T lymphocytes: effects of flutamide and trauma-hemorrhage," Shock 14, 465-470 (2000).

Schneider, E. M., et al., "Generation of mature CD31 and T cell receptor 1 T cells from a leukemic analogue of the putative human (TCR) stem cell by T cell conditioned medium containing IL-3, IL-2, and GM-CSF," Leukemia, 2, 282-289 (1988).

Schröder, J., et al., "Gender differences in human sepsis," Arch Surg 133, 1200-1205 (1998).

Schwacha, M. G., et al., "The immunologic consequences of hemorrhagic shock," Crit Care Shock, 2, 42-64 (1999).

Shafi, Shahid., "Fluid resuscitation and blood replacement in patients with polytrauma," Clinical Orthopaedics & Related Research, 37-42. (2004).

Shea, T. B., "Technical report. An inexpensive densitometric analysis system using a Macintosh computer and a desktop scanner," Biotechniques 16: 1126-1128 (1994).

Sirin, B. H., et al "Ischaemic preconditioning reduces spinal cord injury in transient ischaemia," Acta Cardiol 57, 279-285 (2002).

Slimmer, L. M. & Blair, M. L., "Female reproductive cycle influences plasma volume and protein restitution after hemorrhage in the conscious rat," Am J Physiol Regulatory Integrative Comp Physiol, 271, R626-R633 (1996).

Smith, M. S., et al., "The control of progesterone secretion during the estrous cycle and early pseudo- pregnancy in the rat: prolactin, gonadotropin and steroid levels associated with rescue of the corpus luteum of pseudopregnancy," Endocrinology, 96, 219-226 (1975).

Sribnick, E. A., et al., "Estrogen treatment of spinal cord injury attenuates calpain activation and apoptosis," J Neurosci Res. 84(5), 1064-75 (Oct. 2006).

Sribnick, E. A., et al., "Estrogen as a neuroprotective agent in the treatment of spinal cord injury," Ann N Y Acad Sci, 993, 125-133 (2003).

(56) References Cited

OTHER PUBLICATIONS

Sribnick, A., et al., "Estrogen attenuated markers of inflammation and decreased lesion volume in acute spinal cord injury in rats," J Neurosci Res, 82, 283-293 (2005).
Stampfer, M. J., et al., "Postmenopausal estrogen therapy and cardiovascular disease: ten-year follow-up from the nurses' health study," N Engl J Med, 325, 756-762 (1991).
Starr, R., et al., "A family of cytokine-inducible inhibitors of signaling," Nature, 387, 917-921 (1997).
Stephan, R. N., et al., "Hemorrhage without tissue trauma produces immunosuppression and enhances susceptibility to sepsis," Arch Surg 122, 62-68 (1987).
Stern, et al. 1993. "Effect of blood pressure on hemorrhage volume and survival in a near-fatal hemorrhage model incorporating a vascular injury," Ann Emerg Med, 22(2):155-63.
Stern, S. A., "Low-volume fluid resuscitation for presumed hemorrhagic shock: helpful or harmful?" Curr Opin Crit Care, 7(6), 422-30 (2001).
Stern, Susan A., et al., "Under-resuscitation of near-lethal uncontrolled hemorrhage: effects on mortality and end-organ function at 72 hours," Shock, vol. 15 (1), 16-23 (2001).
Szabó, C., et al., "Protection against peroxynitrite-induced fibroblast injury and arthritis development by inhibition of poly (ADP-ribose) synthetase," Proc Natl Acad Sci USA, 95, 3867-3872 (1998).
Tilg, H., et al., "Interleukin-6 (IL-6) as an anti-inflammatory cytokine: induction of circulating IL-1 receptor antagonist and soluble tumor necrosis factor receptor p55," Blood, 83, 113-118 (1994).
Tonai, T., et al., "Cyclooxygenase-2 induction in rat spinal cord injury mediated by proinflammatory tumor necrosis factor-alpha and interleukin-1," Adv Exp Med Biol., 507, 397-401 (2002).
Tonai, T., et al., "Possible involvement of interleukin-1 in cyclooxygenase-2 induction after spinal cord injury in rats," J Neurochem, 72, 302-309 (1999).
Trinchieri, G., "Interleukin-12 and its role in the generation of TH1 cells," Immunol Today 14, 335-338 (1993).
Vanegas, H., "Schaible HG: Prostaglandins and cyclooxygenases [correction of cycloxygenases] in the spinal cord," Prog Neurobiol, 64, 327-63 (2001).
Vegeto, S., et al.,"Regulation of the lipopolysaccharide signal transduction pathway by 17beta-estradiol in macrophage cells," J Steroid Biochem Mol Biol, 91, 59-66 (2004).
Wang, P., et al., "Is gut the 'motor' for producing hepatocellular dysfunction after trauma and hemorrhagic shock?" J. Surgical Research, 74, 141-148 (1998).
Wang, P., et al., "Measurement of circulating blood volume in vivo after trauma-hemorrhage and hemodilution," Am J Physiol Regulatory Integrative Comp Physiol, 266, R368-R374 (1994).
Wang, P., et al., "Mechanism of adrenal insufficiency following trauma and severe hemorrhage: role of hepatic 11beta-hydroxysteroid dehydrogenase," Arch Surg 134: 394-401 (1999).
Wang, P., et al., "Hepatocellular dysfunction occurs early after hemorrhage and persists despite fluid resuscitation," J Surg Res 48, 464-470 (1990).
Wang, W., et al., "Intestinal alkaline phosphatase: role in the depressed gut lipid transport after trauma-hemorrhagic shock," Shock 8, 40-44 (1997).
Wang, P. & Chaudry, I. H., "Crystalloid resuscitation restores but does not maintain cardiac output following severe hemorrhage," J Surg Res 50, 163-169 (1991).
Watanakunakorn, C., "Staphylococcus aureus endocarditis at a community teaching hospital, 1980 to 1991. An analysis of 106 cases," Arch Intern Med, 154, 2330-2335 (1994).

Wichmann, M. W., et al., "Flutamide: a novel agent for restoring the depressed cell-mediated immunity following soft-tissue trauma and hemorrhagic shock," Shock 8, 1-7; 242-248 (1997).
Wichmann, M. W., et al., "Male sex steroids are responsible for depressing macrophage immune function after trauma-hemorrhage," Am J Physiol, 273, C1335-C1340 (1997).
Wichmann, M. W., et al., "Mechanism of immunosuppression in males following trauma-hemorrhage: critical role of testosterone," Arch Surg; 131:1186-1191 (1996).
Wichmann, M. W., et al., "Enhanced immune responses in females as opposed to decreased responses in males following hemorrhagic shock," Cytokine 8, 853-863 (1996).
Wolfgang, Ertel, et al., "Biological significance of elevated TNF levels: in vivo administration of monoclonal antibody against TNF after hemorrhage shock increases the capacity of macrophages to release TNF while restoring immuno-responsiveness," Cytokine, 6, 624-632 (1994).
Xu, J, et al., "iNOS and nitrotyrosine expression after spinal cord injury," J Neurotrauma, 18, 523-532 (2001).
Xu, Y. X., et al., "Prolonged immunodepression after trauma and hemorrhagic shock," J Trauma, 44, 335-341 (1998).
Yamanishi, Y, et al., "Regulation of joint destruction and inflammation by p53 in collagen-induced arthritis," Am J Pathol, 160, 123-130, (2002).
Yune, T. Y., et al., "Systemic administration of 17beta-estradiol reduces apoptotic cell death and improves functional recovery following traumatic spinal cord injury in rats," J Neurotrauma, 21, 293-306 (2004).
Zellweger, R, et al., "Trauma-hemorrhage causes prolonged depression in cellular immunity," Shock, 4, 149-153 (1995).
Zellweger, R, et al., "Females in proestrus state maintain splenic immune functions and tolerate sepsis better than males," Crit Care Med 25, 106-110 (1997).
Zellweger, R, et al., "Prolactin administration following hemorrhagic shock improves macrophage cytokine release capacity and decreases mortality from subsequent sepsis," J Immunol., 157, 5748-5754 (1996).
International Search Report and Written Opinion mailed on Jun. 7, 2013 for international application No. PCT/US2013/031887, which was filed on Mar. 15, 2013 and published as WO2013/172969 on Nov. 21, 2013. (Inventor—Chaudry; Applicant—The UAB Research Foundation) (pp. 1-2).
Examiner Interview Summary Record issued on Oct. 12, 2010 for U.S. Appl. No. 11/748,453, filed May 14, 2007 and published as US-2007-0287684 on Dec. 13, 2007. (Inventor—Chaudry; Applicant—The UAB Research Foundation) (pp. 1-2).
Final Rejection issued on Mar. 19 , 2010 for U.S. Appl. No. 11/748,453, filed May 14, 2007 and published as US-2007-0287684 on Dec. 13, 2007. (Inventor—Chaudry; Applicant—The UAB Research Foundation) (pp. 1-10).
Preliminary Amendment filed on Oct. 15, 2009 for U.S. Appl. No. 11/748,453, filed May 14, 2007 and published as US-2007-0287684 on Dec. 13, 2007. (Inventor—Chaudry; Applicant—The UAB Research Foundation) (pp. 1-6).
Non-Final Rejection issued on Aug. 13, 2009 for U.S. Appl. No. 11/748,453, filed May 14, 2007 and published as US-2007-0287684 on Dec. 13, 2007. (Inventor—Chaudry; Applicant—The UAB Research Foundation) (pp. 1-13).
Examiner Interview Summary Record issued on Aug. 13, 2009 for U.S. Appl. No. 11/748,453, filed May 14, 2007 and published as US-2007-0287684 on Dec. 13, 2007. (Inventor—Chaudry; Applicant—The UAB Research Foundation) (pp. 1-2).
Preliminary Amendment filed on Aug. 4, 2009 for U.S. Appl. No. 11/748,453, filed May 14, 2007 and published as US-2007-0287684 on Dec. 13, 2007. (Inventor—Chaudry; Applicant—The UAB Research Foundation) (pp. 1-8).

* cited by examiner

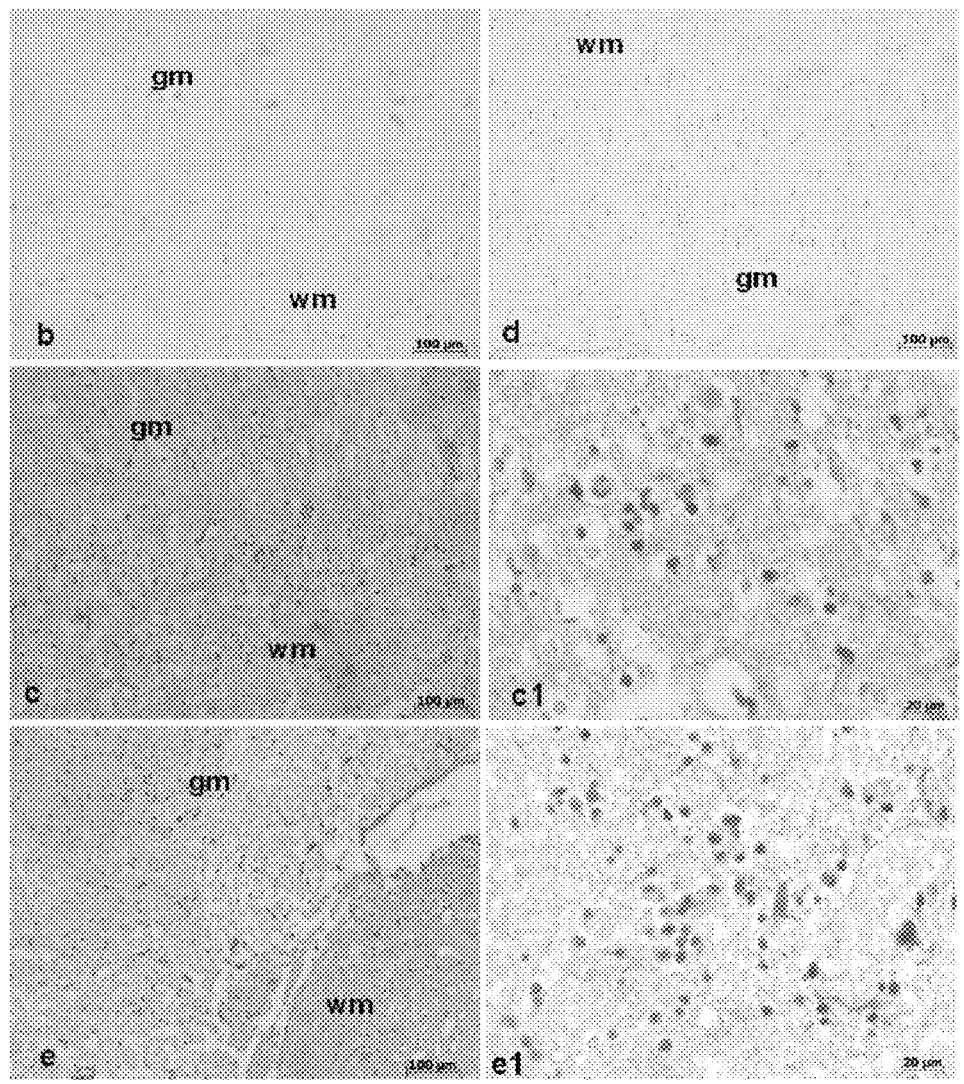
FIG. 32B, FIG. 32C, FIG. 32C1, FIG. 32D, FIG. 32E, FIG. E1

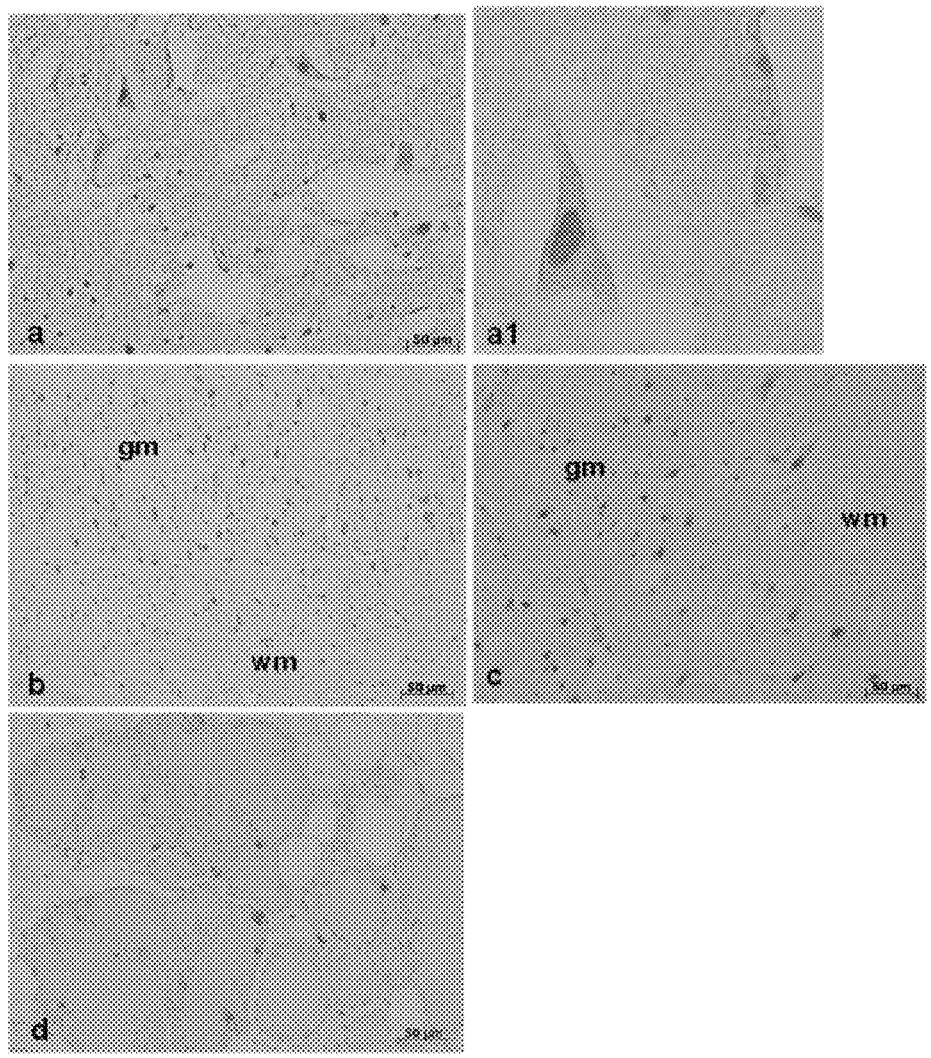
FIG. 37A, FIG. 37A1, FIG. 37B, FIG. 37C, FIG. 37D

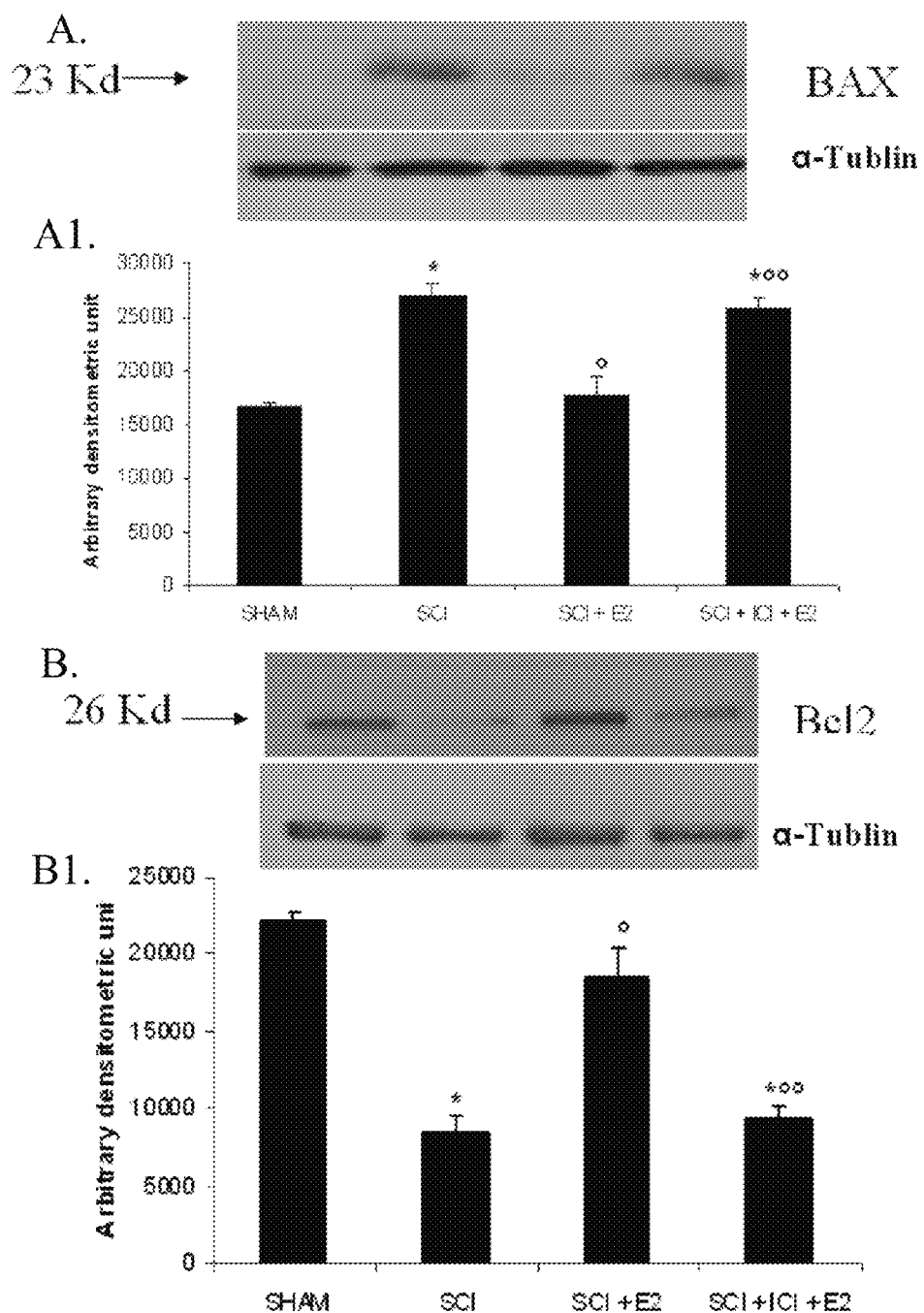
FIG. 38A, FIG. 38A1, FIG. 38B, FIG. 38B1

METHODS AND COMPOSITIONS FOR TREATING TRAUMA-HEMORRHAGE USING ESTROGEN AND DERIVATIVES THEREOF

CROSS REFERENCE TO RELATED APPLICATION

This application is a continuation of and claims priority to U.S. application Ser. No. 11/748,453, filed May 14, 2007, now abandoned, which claims the benefit of U.S. Provisional Application No. 60/802,352, filed on May 22, 2006, which are hereby incorporated in their entirety.

ACKNOWLEDGEMENT

This invention was made with government support under grant number W81XWH-05-2-0046 and W911NF-06-1-0219 awarded by the DARPA. The United States Government has certain rights in this invention.

BACKGROUND OF THE INVENTION

Hemorrhage is the most common cause of death among injured or treated individuals including those who die prior to reaching care, who die in emergency medical care, e.g. emergency room, or who die in the operating room (Holcomb 1997; Holcomb 1999). The most common causes of death of individuals in post-operative critical care are those involving sequellae of poorly controlled hemorrhage and shock. In the prehospital setting, most internal bleeding is not accessible for direct intervention. In the hospital setting, there are sources of bleeding which cannot be immediately controlled with the best surgical techniques, e.g. deep liver injuries with liver vein disruption, pelvic ring fractures with direct bone bleeding, pelvic venous plexus tears, etc.

Clinical and epidemiological studies have indicated gender differences in the response to various adverse circulatory conditions (Offner 1999). In this regard, studies have shown that sex steroids have either deleterious or beneficial effects on cardiac and hepatic functions not only under normal conditions but also after circulatory stress. For example, testosterone-receptor blockade after trauma-hemorrhage has been shown to improve organ functions in males (Remmers 1998). Alternatively, castration days before hemorrhagic shock prevented the depression in myocardial functions that is usually observed in males under those conditions (Remmers 1997). Furthermore, significantly reduced cardiovascular morbidity and mortality has been reported in post-menopausal women receiving hormone replacement therapy (Stampfer 1991). Moreover, studies have indicated that 17β-estradiol is involved in various physiologic processes such as vascular response modulation.

It has been demonstrated that the proestrus state of the female rodent shows the highest plasma concentration of estradiol and prolactin (Smith 1975). The plasma levels of both hormones are low on the morning of estrus and then gradually increase over diestrus to achieve their peak levels on the morning of proestrus (Smith 1975). Studies by Slimmer and Blair (Slimmer 1996) have shown that female rats in the proestrus stage of the reproductive cycle exhibit a more vigorous restitution response than either estrus females or males after simple hemorrhage.

Furthermore, Wichmann et al. (1996) have shown that female mice subjected to hemorrhage during the proestrus state have enhanced immune responses as opposed to decreased responses in males. Therefore, the female reproductive cycle is an important variable not only with regard to immunological responses but also by influencing physiological responses (i.e., cardiac and hepatic functions) after trauma-hemorrhage and resuscitation (Angele 1999).

Trauma-hemorrhage produces a pronounced depression of immune functions in males that persists for up to 10 days after resuscitation (Chaudry 1992; Xu 1998). Alterations in the function of various macrophage (MΦ) populations (peritoneal, splenic, hepatic [Kupffer cells]) has been implicated in the immune depression and subsequent increased susceptibility to sepsis observed under such conditions (Ayala 1989; Ayala 1990; Ayala 1991). It has been shown that testosterone plays a significant role in producing this immunodepression and increased susceptibility to subsequent sepsis after trauma-hemorrhage. (Wichmann 1997; Angele 1997; Wichmann 1997). In contrast, female mice in the proestrus state of the estrus cycle have maintained or enhanced immune responses under such conditions; this is associated with improved survival after the induction of subsequent sepsis. (Diodato 2000; Slimmer 1996). What is needed in the art are methods and compositions related to treating trauma-hemorrhage comprising administering estrogen to a subject in need thereof.

SUMMARY OF THE INVENTION

In accordance with the purpose(s) of this invention, as embodied and broadly described herein, this invention, in one aspect, relates to a method of ameliorating one or more effects of a traumatic injury in a subject comprising administering estrogen to the subject in a low volume of solution. For example, the estrogen can be administered in 40 mL of solution or less, or 0.5 ml/kg or less of estrogen in solution can be administered to the subject. The estrogen can be in a cyclodextrin complex. Administration can be, for example, intravenous or intraosseous. The estrogen can be β-estradiol or equiline sulfate. The traumatic injury can involve an inflammatory response, and can involve low blood pressure compared to a control blood pressure. The traumatic injury can involve severe blood loss. For example, the severe blood loss can comprise 40% or more blood loss from the subject. Administration of estrogen can maintain a state of permissive hypotension. The cyclodextrin complex can comprise, for example, 2-hydroxypropyl-β-cyclodextrin or sulfobutyl ether cyclodextran. The estrogen can be administered prior to the traumatic injury, after the traumatic injury but before treatment, or after treatment has begun.

Also disclosed is a method of ameliorating one or more effects of severe blood loss in a subject comprising administering estrogen to the subject. For example, the severe blood loss can comprise 40%, 50%, or 60% or more blood loss from the subject. The estrogen can be administered in, for example, 40 mL of solution or less, or 0.5 ml/kg or less of estrogen in solution can be administered to the subject. The estrogen can be in a cyclodextrin complex. Administration can be, for example, intravenous or intraosseous. The estrogen can be, for example, β-estradiol or equiline sulfate. The traumatic injury can involve an inflammatory response, and can involve low blood pressure compared to a control blood pressure. The traumatic injury can involve severe blood loss. Administration of estrogen can maintain a state of permissive hypotension. The cyclodextrin complex can comprise, for example, 2-hydroxypropyl-β-cyclodextrin or sulfobutyl ether cyclodextran. The estrogen can be administered prior to the traumatic injury, after the traumatic injury but before treatment, or after treatment has begun.

Also disclosed is a method of prolonging viability of tissue, organ, cell, or an entire body for donation comprising contacting the tissue, organ, cell, or entire body with estrogen. The contacting step can be performed in vivo by administering estrogen to the donor, in vitro, or ex vivo.

Also disclosed is a method of improving organ and cell viability of a transplanted tissue, organ or cell by contacting the tissue, organ, or cell with estrogen. The contacting step can be performed in vivo by administering estrogen to the recipient of the donated tissue, organ, or cell. The contacting step can also be performed in vivo by administering estrogen to the donor, in vitro, or ex vivo.

Further disclosed is a method of ameliorating one or more effects of an aortic cross clamp used during surgery in a subject in need thereof, comprising administering estrogen in a cyclodextrin complex to the subject. For example, administration of estrogen prior to, during, or after use of the aortic cross clamp can maintain a state of permissive hypotension.

Disclosed is a kit comprising microencapsulated estrogen, wherein the estrogen is in less than 40 mL of vehicle. The estrogen can also be in a syringe, and in one example, the syringe can be in a bullet-proof container. The estrogen can be in a cyclodextrin complex. The kit can comprise two separate compartments, one of which comprises sterile dried estrogen, and one comprising diluent.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 32 shows the effects of 17β-estradiol on myeloperoxidase (MPO) activity. Following the injury myeloperoxidase (MPO) activity in spinal cord of non-treated SCI-operated mice was significantly increased at 24 hours after the damage in comparison to sham mice. Treatment with 17β-estradiol significantly reduced the SCI-induced increase in MPO activity. Co-administration of ICI 182,780 and 17β-estradiol significantly blocked the effect of the 17β-estradiol on MPO activity. In addition, no positive staining for MPO was observed in spinal cord tissues collected from sham-operated mice (b). A significant positive staining for MPO was observed in the spinal cord tissues collected from SCI-operated mice (c see particle c1). In SCI-operated mice treated with 17β-estradiol (d) the staining for MPO was visibly and significantly reduced in comparison with the SCI-operated mice. Co-administration of ICI 182,780 and 17β-estradiol significantly blocked the effect of the 17β-estradiol on MPO formation in the spinal cord tissues (e see particle e1). Image is a representative of at least 3 experiments performed on different experimental days. Data are mean±S.E. mean of 10 mice for each group. *p<0.05 vs. vehicle. °p<0.01 vs. SCI. °°p<0.01 vs. 17β-estradiol. wm: White matter; gm: gray matter.

FIG. 37 shows representative TUNNEL coloration in rat spinal cord tissue section. The number of apoptotic cells increased at 24 hours after SCI (a) associated with a specific apoptotic morphology characterized by the compaction of chromatin into uniformly dense masses in perinuclear membrane, the formation of apoptotic bodies as well as the membrane blebbing (see particle a1). In contrast, tissues obtained from 17β-estradiol-treated mice (b) demonstrated a small number of apoptotic cells or fragments. Co-administration of ICI 182,780 and 17β-estradiol significantly blocked the effect of the 17β-estradiol on the presence of apoptotic cells (c). Section d demonstrates the positive staining in the Kit positive control tissue. Figure is representative of at least 3 experiments performed on different experimental days. wm: White matter; gm: gray matter.

FIG. 38 shows a representative Western blot of Bax levels (a) and Bcl-2 (b). Western blot analysis was realized in spinal cord tissue collected at 24 h after injury. Sham: basal level of Bax was present in the tissue from sham-operated mice. SCI: Bax band is more evident in the tissue from spinal cord-injured mice. SCI+17β-estradiol: Bax band disappeared in the tissue from spinal cord-injured mice which received 17β-estradiol. SCI+ICI 182,780+17β-estradiol: Bax band is more evident in comparison with the band present in the tissue from 17β-estradiol-treated mice. Sham: basal level of Bcl-2 was present in the tissue from sham-operated mice. SCI: Bcl-2 band disappeared in the tissue from spinal cord-injured mice. SCI+17β-estradiol: Bcl-2 band is more evident in the tissue from spinal cord-injured mice which received 17β-estradiol. SCI+ICI 182,780+17β-estradiol: BCL2 band is less evident in comparison with the band present in the tissue from 17β-estradiol-treated mice. (a1 and b1) The intensity of retarded bands (measured by phosphoimager) in all the experimental groups. Immunoblotting in panels A and B is representative of one spinal cord tissue out of 5-6 analyzed. The results in panels A1 and B1 are expressed as mean±S.E.M. from 5-6 spinal cord tissues. *p<0.05 vs. vehicle. °p<0.01 vs. SCI. °°p<0.01 vs. 17β-estradiol.

DETAILED DESCRIPTION OF THE INVENTION

Figure 1:
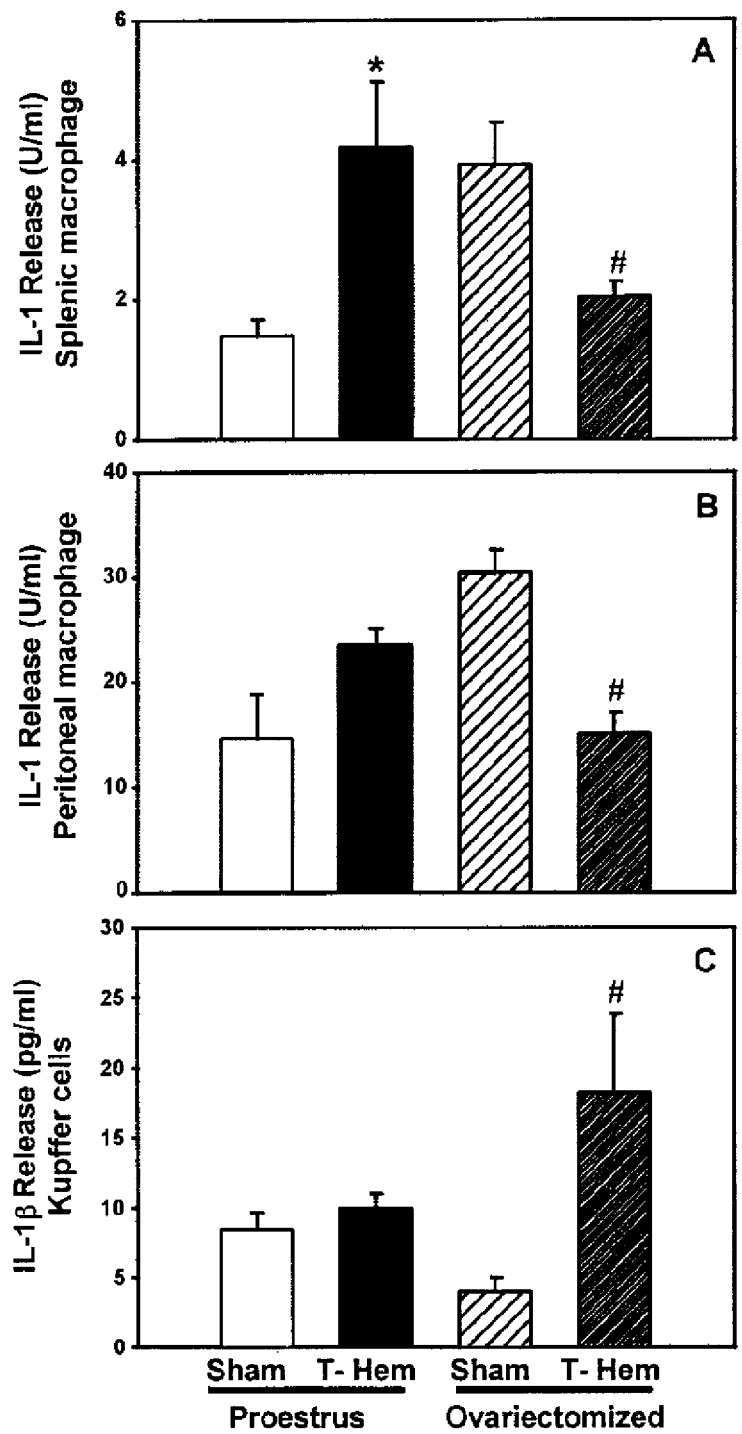
FIG. 1 shows the release of interleukin-1 (IL-1) by splenic macrophages (A) or peritoneal macrophages (B) and Kupffer cells (C) at 2 hours after sham operation or trauma-hemorrhage. Concentrations of IL-1 in supernatants from splenic and peritoneal macrophages were measured by a specific bioassay (D10.G4.1), whereas Kupffer cell IL-1 release was measured by enzyme-linked immunosorbent assay specific for murine IL-1. Values are means±SEM of seven or eight animals per group; analysis of variance, $*p<0.05$ vs. proestrus sham; $\#p<0.05$ vs. ovariectomy sham.

The present invention may be understood more readily by reference to the following detailed description of preferred embodiments of the invention and the Examples included therein and to the Figures and their previous and following description.

A. Definitions

As used in the specification and the appended claims, the singular forms "a," "an" and "the" include plural referents unless the context clearly dictates otherwise. Thus, for example, reference to "a small molecule" includes mixtures of one or more small molecules, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The terms "higher," "increases," "elevates," or "elevation" refer to increases above basal levels, e.g., as compared to a control. The terms "low," "lower," "reduces," or "reduction" refer to decreases below basal levels, e.g., as compared to a control. For example, basal levels are normal in vivo levels prior to, or in the absence of, the addition of estrogen.

As used herein, "hemostasis" is the arrest of bleeding, involving the physiological process of blood coagulation at ruptured or punctured blood vessels and possibly the contraction of damaged blood vessels.

"Inflammation" or "inflammatory" is defined as the reaction of living tissues to injury, infection, or irritation. Anything that stimulates an inflammatory response is said to be inflammatory.

"Transplant" is defined as the transplantation of an organ or body part from one organism to another.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

The term "cyclodextrin" is intended to mean a cyclodextrin or a derivative thereof as well as mixtures of various cyclodextrins, mixtures of various derivatives of cyclodextrins and mixtures of various cyclodextrins and their derivatives.

The term "cyclodextrin complex" is intended to mean a complex between an estrogen and a cyclodextrin, wherein a molecule of the estrogen is at least partially inserted into the cavity of one cyclodextrin molecule. Furthermore, the molecule of an estrogen may at least partially be inserted into the cavity of more cyclodextrin molecules, and two moieties of a single estrogen molecule can each be inserted into one cyclodextrin molecule to give 2:1 ratio between cyclodextrin and estrogen. Thus, the complex can be termed as an inclusion complex (clathrate) between an estrogen and a cyclodextrin. Similarly, the complex can comprise more than one molecule of estrogen at least partially inserted into one or more cyclodextrin molecules, wherein for example, two estrogen molecules are at least partially inserted into a single cyclodextrin molecule, to give a 1:2 ratio between cyclodextrin and estrogen. These are merely examples and not intended to be limiting, as one of skill in the art would be able to form additional estrogen-cyclodetxrin complexes.

An "estrogen compound" is defined here and in the claims as any of the structures described in the 11th edition of "Steroids" from Steraloids Inc., Wilton N.H., herein incorporated by reference in its entirety for its teaching concerning estrogen and derivatives thereof. Included in this definition are non-steroidal estrogens described in the aforementioned reference. Other estrogen compounds included in this definition are estrogen derivatives, estrogen metabolites and estrogen precursors as well as those molecules capable of binding cell associated estrogen receptor as well as other molecules where the result of binding specifically triggers a characterized estrogen effect. Unless the context clearly indicates otherwise, reference herein to "estrogen" is intended to refer both estrogen and estrogen compounds; and such reference is intended to refer to estrogen, estrogen compounds, or a combination.

B. Methods

Treatment with estrogen 17β-estradiol; also referred to herein as E2) is capable of dramatically promoting survival of subjects which have undergone massive (i.e., 60%) blood loss. The estrogen can administered prior to, or after major blood loss, and prior to or during resuscitation following trauma-hemorrhage, which makes it compatible with the needs of emergency or critical care treatment. It has been found that female mice fared far better than male counterparts in surviving experimental sepsis as well as trauma-hemorrhage. It was further found that this gender bias was most pronounced in proestrus females, which express greatly elevated estrogen systemically. Confirmatory studies showed that the administration of exogenous estrogen to both males and non-proestrus females produces the same beneficial effects on cardiac and immunological functions, and also on decreasing the susceptibility to and mortality from sepsis (infections) following traumatic injury and blood loss.

Figure 21:
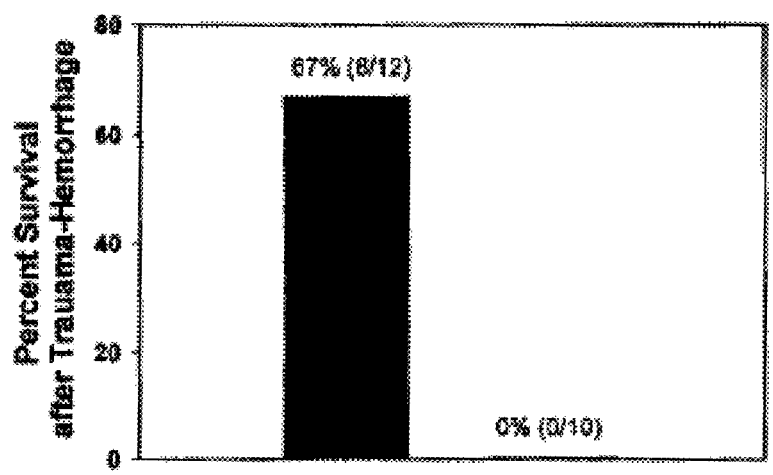
FIG. 21 shows the percentage of survival in estrogen-treated and non-treated rats. The survival rate is 68% for estrogen-treated rats, while all untreated control rats died within the initial 3-hour interval.

Furthermore, crystalloid fluid resuscitation was administered following an initial 3-hour interval after the trauma and major blood loss, and rats were followed for 7 days. It has been observed that rats which survive for the initial 3 hours uniformly go on to survive for prolonged period of time and were then sacrificed. The survival rate is 68% for estrogen-treated rats, while all untreated control rats have died within the initial 3-hour interval (see FIG. 21).

Estrogen can up-regulate E2 receptors, prevent harmful inflammatory signaling cascades, and most significantly lower vascular peripheral resistance. This allows for better perfusion of vital organs under these low-flow conditions. In addition the presence of estrogen receptors within the mitochondrion shows an intimate coupling of metabolism to the sensing of estrogen, which can account for the preservation (or compensation) of ATP levels in the liver. The beneficial effects of estrogen in injury extend to protection of brain tissue. In a mouse model, it was shown that soluble estrogen at a dose that approximates physiological levels was able to preserve brain tissue, which was attributed to improved microcirculation.

Disclosed herein are methods of ameliorating one or more effects of a traumatic injury in a subject comprising administering estrogen in a cyclodextrin complex to the subject. By "ameliorating the effects" is meant a reduction or prevention of those diseases, symptoms, and complications associated with trauma, injury, or blood loss. For example, administration of estrogen can prevent or decrease the occurrence and complications of sepsis and multiple organ failure as sequelae of traumatic injury. Hemorrhagic shock, in addition to directly resulting in early fatality, is a predictor of poor outcome in the injured patient. Early hypotension (systolic blood pressure=90 mmHg) with hemorrhage in the field or at initial hospital evaluation is associated with complications such as eventual organ failure and the development of infections, including sepsis. Furthermore, as a critically injured patient progresses through the phases of trauma care, death from causes unrelated to specific injuries becomes more common. Infections such as sepsis and pneumonia, systemic inflammatory response syndrome, and multiple organ failure become the primary etiologies of traumatic death in the trauma patient. Treatment with estrogen can reduce or prevent infection such as sepsis and pneumonia or other infections, inflammation, and organ failure, for example.

A severe infection, such as those accompanying traumatic injury, can be associated with sepsis. Sepsis, also known as systemic inflammatory response syndrome (SIRS), is a severe illness caused by overwheming infection of the bloodstream by toxin-producing bacteria. Sepsis can be caused by bacterial infection that can originate anywhere in the body. Common sites include, but are not limited to, the kidneys (upper urinary tract infection), the liver or the gall bladder, the bowel (usually seen with peritonitis), the skin (cellulitis), and the lungs (bacterial pneumonia). In sepsis, blood pressure drops, resulting in shock. Major organs and systems, including the kidneys, liver, lungs, and central nervous system, stop functioning normally. Sepsis is often life-threatening, especially in people with a weakened immune system or other medical illnesses.

Administration of estrogen after a traumatic injury can also help to maintain a state of permissive hypotension until definitive treatment of injury and/or blood loss can be provided. Induced, controlled, or permissive hypotension is defined as the deliberate acute reduction of arterial blood pressure to reduce blood loss. Furthermore, administration of estrogen after blunt or penetrating trauma, soft tissue injury and/or bone fracture with blood loss can block or ameliorate complications of cardiac arrest as sequelae of hemorrhage.

Estrogen can be administered near the time of traumatic injury, as with treatment by first responders. The estrogen can also be administered after the patient has reached a treatment facility, and before the proper treatment can be received. For example, during a terrorist or other large-scale incident where many are wounded and taken to medical facilities, estrogen can be administered to allow the waiting patients to have a higher chance of survival, minimize the inflammatory response, and minimize hemorrhage until the proper treatment can be received. The estrogen can also be administered after traumatic injury, but before fluid resuscitation–until hemorrhage can be controlled surgically, for example. In one example, the fluid resuscitation can be used to restore the circulating blood volume. This can allow the patient to live up to 30 minutes, or 1, 2, 3, 4, 5, 6, 7, 8, 9, 10, 11, 12, 18, or 24 hours longer than they would have without estrogen treatment or other medical attention.

Estrogen can be administered to the subject before, after, or during traumatic injury or surgery. When administered before, estrogen can be administered, for example, 48, 36, 24, 18, 12, 11, 10, 9, 8, 7, 6, 5, 4, 3, 2, or 1 hour prior to the trauma or surgery, or 50, 40, 30, 20, 10, 5, or 1 minute before the trauma or surgery, or any amount in between. Estrogen can also be administered after the traumatic injury, but before treatment (treatment in this context meaning surgery or other forms of professional healthcare). Resuscitation, such as fluid resuscitation, is a useful form of such treatment. For example, estrogen can be administered after tramatic injury and before resuscitation, such as fluid resuscitation. Estrogen can be administered, for example, 24, 18, 12, 11, 10, 9, 8, 7, 6, 5, 4, 3, 2, or 1 hours after the injury, or 50, 40, 30, 20, 10, 5, or 1 minute after the injury, or any amount in between these times. Estrogen can also be administered at various times prior to treatement, either particular treatments or combinations of treatments. For example, estrogen can be administered after tramatic injury and for various times before resuscitation, such as fluid resuscitation. Estrogen can be administered, for example, 48, 36, 24, 18, 12, 11, 10, 9, 8, 7, 6, 5, 4, 3, 2, or 1 hour prior to treatment or the start of treatment, or 50, 40, 30, 20, 10, 5, or 1 minute prior to treatment or the start of treatment, or any amount in between. The estrogen can also be administered after treatment has begun. It can be administered 24, 18, 12, 11, 10, 9, 8, 7, 6, 5, 4, 3, 2, or 1 hours after treatment has begun, or 50, 40, 30, 20, 10, 5, or 1 minute after treatment has begun, or any amount in between these times The estrogen can also be administered before, during, or after the use of an aortic cross clamp, as discussed herein.

Also disclosed herein is a method of prolonging viability of tissue, organ, cell, or an entire body for donation comprising contacting the tissue, organ, cell, or entire body with estrogen. When a cell, tissue, organ, or entire body is to be donated, it has been found that treatment with estrogen can prolong the viability of the cell, tissue, organ, or body. By exposing the transplantation material to estrogen, the viability of the cells, tissue, or organs can increase by 2, 3, 4, 5, 6, 7, 8, 9, 10, 20, 50, or 100-fold or more. This allows for a greater time to lapse between harvesting the cells, tissue, or organ for transplantation, and the time when it is transplanted into the recipient. The increased viability of the cells, tissue, or organ can extend the time from harvest to transplantation by 1, 2, 3, 4, 5, 6, 7, 8, 9, 10, 11, 12, 18, or 24 hours or more. This method can be used with a subject who has become brain-dead, thereby extending the viability of the cell, tissues, and organs for donation.

Also disclosed herein is a method of reducing rejection, or preventing deterioration of tissue, organs or cells for transplantation, by contacting the tissue, organ, or cell with estrogen. When a cell, tissue, or organ is transplanted, cell and organ dysfunction and failure can result due to lack of blood flow to that organ due to cellular swelling, for example. This can lead to further complications in the subject receiving the donated cell, tissue, or organ. One of the complications resulting from donation is ischemia. The methods of administering estrogen disclosed herein can also be used to reduce the effects of ischemia on a donor tissue, organ or cell comprising contacting the tissue, tissue, organ or cell with estrogen in a cyclodextrin complex. The contacting step can be performed in vivo by administering estrogen to the donor in a cyclodextrin complex, for example. The exposure step can also be performed in vitro, by contacting cells, tissues, or organs with estrogen. The exposure step can also be performed in the body prior to harvesting the organ, ex vivo, wherein cells, tissues, or organs are removed from the body and perfused with estrogen, and then transplanted into the body. Ischemia is defined as a total lack of blood flow to a bodily organ, tissue, or part caused by constriction or obstruction of the blood vessels. This is a frequent problem with transplants, often leading to transplant rejection in a transplant recipient. "Transplant rejection" is defined as an immune response triggered by the presence of foreign blood or tissue in the body of a subject. In one example of transplant rejection, antibodies are formed against foreign antigens on the transplanted material. The transplantation can be, for example, organ transplantation, such as liver, kidney, skin, eyes, heart, or any other transplantable organ of the body or part thereof.

The methods and compositions disclosed herein can also be used to treat wounds and bone fractures, as well as osteotomies, non unions or delayed unions, soft tissue injuries, or reconstructive surgery sites. Exposing the injured bone or tissue to estrogen can shorten the healing time, thereby ameliorating the effects of the damaged bone or tissue. "Healing" is defined as the time from injury until the subject's body has recovered to the full extent possible. Estrogen can also be used in conjunction with a heart-lung machine. Estrogen can also be used to treat malignant hypotension. Estrogen can also be used to treat spinal cord injury (SCI) (Sribnick et al. J Neurosci Res. 2006 October; 84(5):1064-75, herein incorporated by reference in its entirety for its teaching concerning treating spinal cord injury with estrogen).

Subjects can be maintained in a state of permissive hypotension with the use of the estrogen compositions disclosed herein. The standard approach to the trauma victim who is hypotensive from know or presumed hemorrhage has been to infuse large volumes of fluids as early and as rapidly as possible. The goals of this treatment strategy are rapid restoration of intravascular volume and vital signs towards normal, and maintenance of vital organ perfusion. However, it has been shown that in the setting of penetrating injury to a major or even a small blood vessel and severe hemorrhage, the practice of aggressive fluid resuscitation can be harmful, resulting in increased hemorrhage volume and subsequently greater mortality. This has been demonstrated in animal models representative of penetrating trauma as well as those representative of blunt trauma. The data show that limited or hypotensive resuscitation may be preferable for the trauma victim with the potential for ongoing uncontrolled hemorrhage. Limited resuscitation provides a mechanism of avoiding the detrimental effects associated with early aggressive resuscitation, while maintaining a level of tissue perfusion that although decreased from the normal physiologic range is adequate for short periods (Stern et al. Current Opinion in Critical Care. 2001 December; 7(6):422-30; Pepe et al. Prehospital Emergency Care 2002 Janauary-March; 6:81-91; both of which are incorporated in their entirety for their teaching concerning permissive hypotension). Delay of or limited resuscitation, however, can be harful to the subject and the subject's tissues due to all of the negative effects of low or stopped blood flow and/or hypotension. It has been discovered that the estrogen compositions disclosed herein can be given to a subject in order to allow the subject to stay in a state of permissive hypotension longer than without administration of estrogen. This can increase longevity and survival rates in the subject. In particular, hypotensive subjects to which estrogen has been administered can survive and suffer reduced negative effects in a hypotensive state for longer periods than subject to which estrogen is not administered. Thus, the disclosed methods and compositions can provide improved outcomes for subjects to which treatment is delayed during or following hypotensive conditions.

As discussed herein the estrogen compositions can be given in low volume solutions. For example, the estrogen composition can be given to a subject in, for example, less than 200, 175, 150, 125, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 ml of solution, or any amount in between.

The volume of solution comprising estrogen administered to a subject can be less than, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 ml/kg of body weight.

The methods and compositions disclosed herein can be used with a variety of subjects, including humans and animals. For example, the methods and compositions disclosed herein can be used for livestock that are injured until they can be properly transported. The methods are also useful with animals that are used for racing. These animals often receive serious injury while racing. Examples of race animals include, but are not limited to, horses and dogs.

Figure 22A:
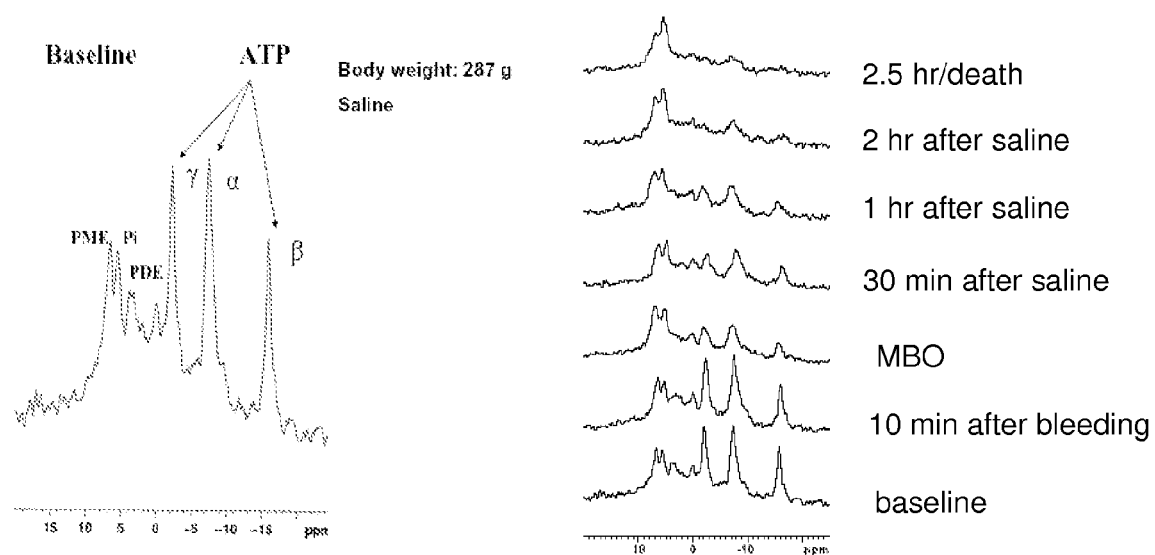
FIG. 22a shows non-surviving cyclodextrin control and 22b shows surviving estrogen-treated rats.
Figure 22B:
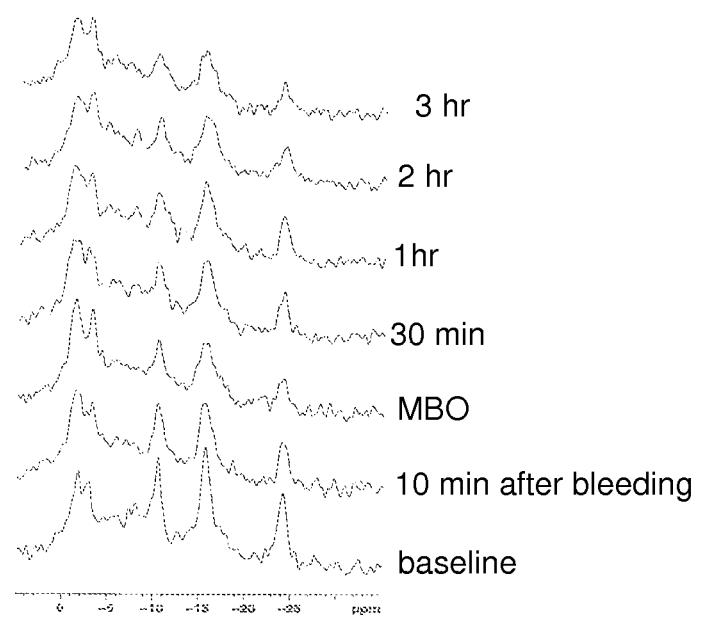
FIG. 22 shows NMR spectra for $^{31}$P/ATP in T-H rat liver (non-surviving). Imaging and nuclear magnetic resonance studies were conducted to evaluate the effects of E2 on preservation of adenosine triphosphate (ATP) and pH levels in the liver. These in vivo studies have shown that estrogen-treated rats' livers have preservation of intracellular ATP.
Figure 23:
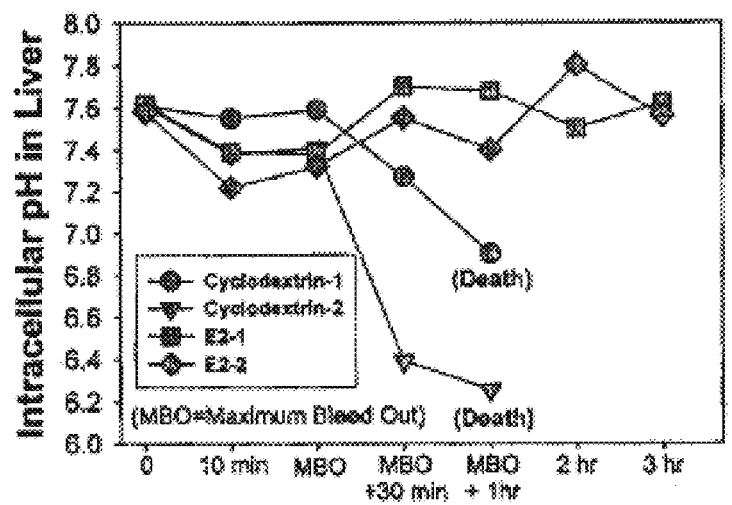
FIG. 23 shows intracellular pH in cyclodextrin control and E2 experimental rats. pH remains near neutral in treated rats, but falls to sub-physiological acidic levels in control animals.
Figure 24:
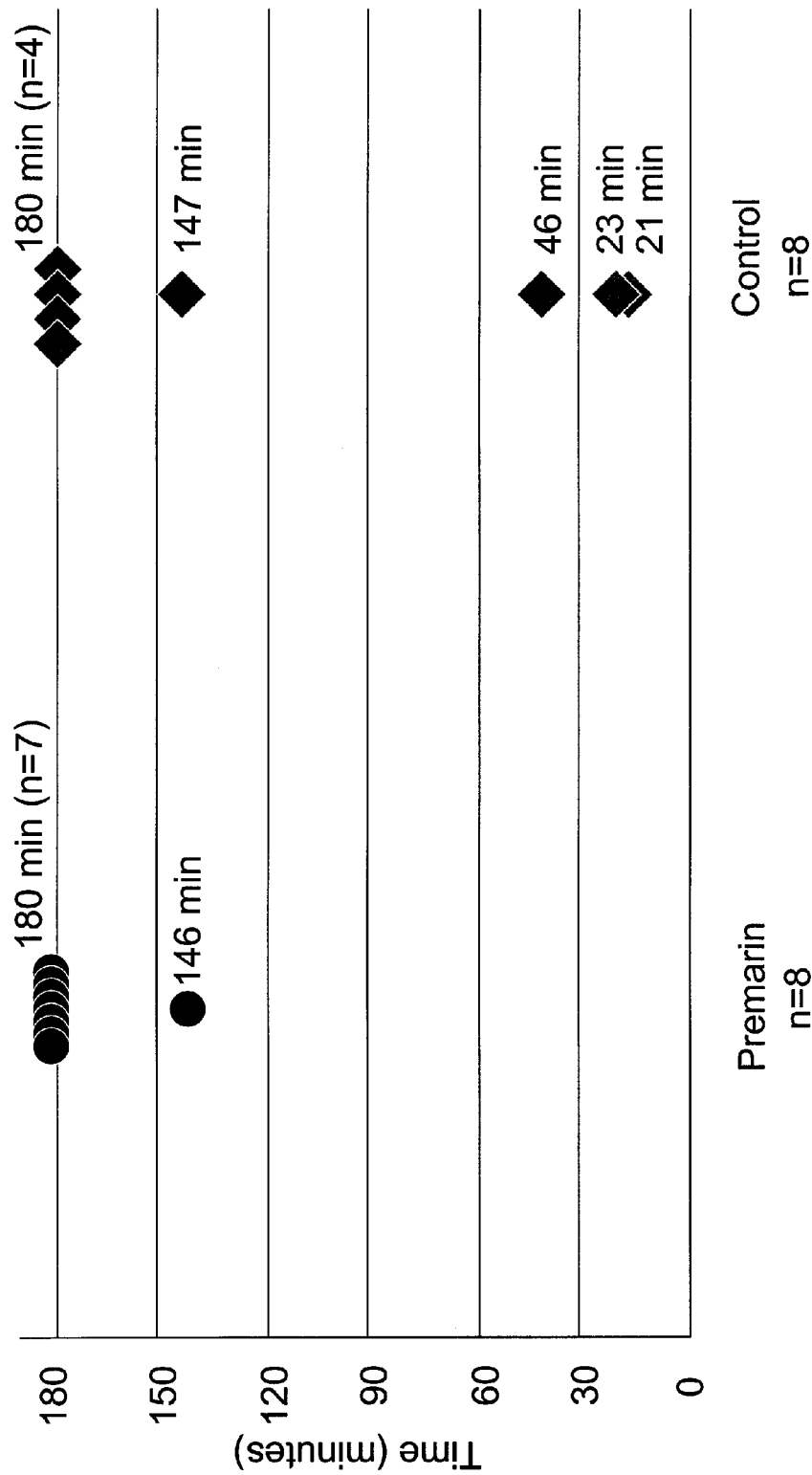
FIG. 24 shows a timeline of the longevity of rats treated with Premarin™ or a control. 16 rats were subjected to 60% removal of blood volume, using the same protocol found in Example 5. Seven out of eight rats exposed to Premarin™ survived 3 hours or more, while only four rats not exposed to Premarin™ lived to the 3-hour mark.
Figure 25:
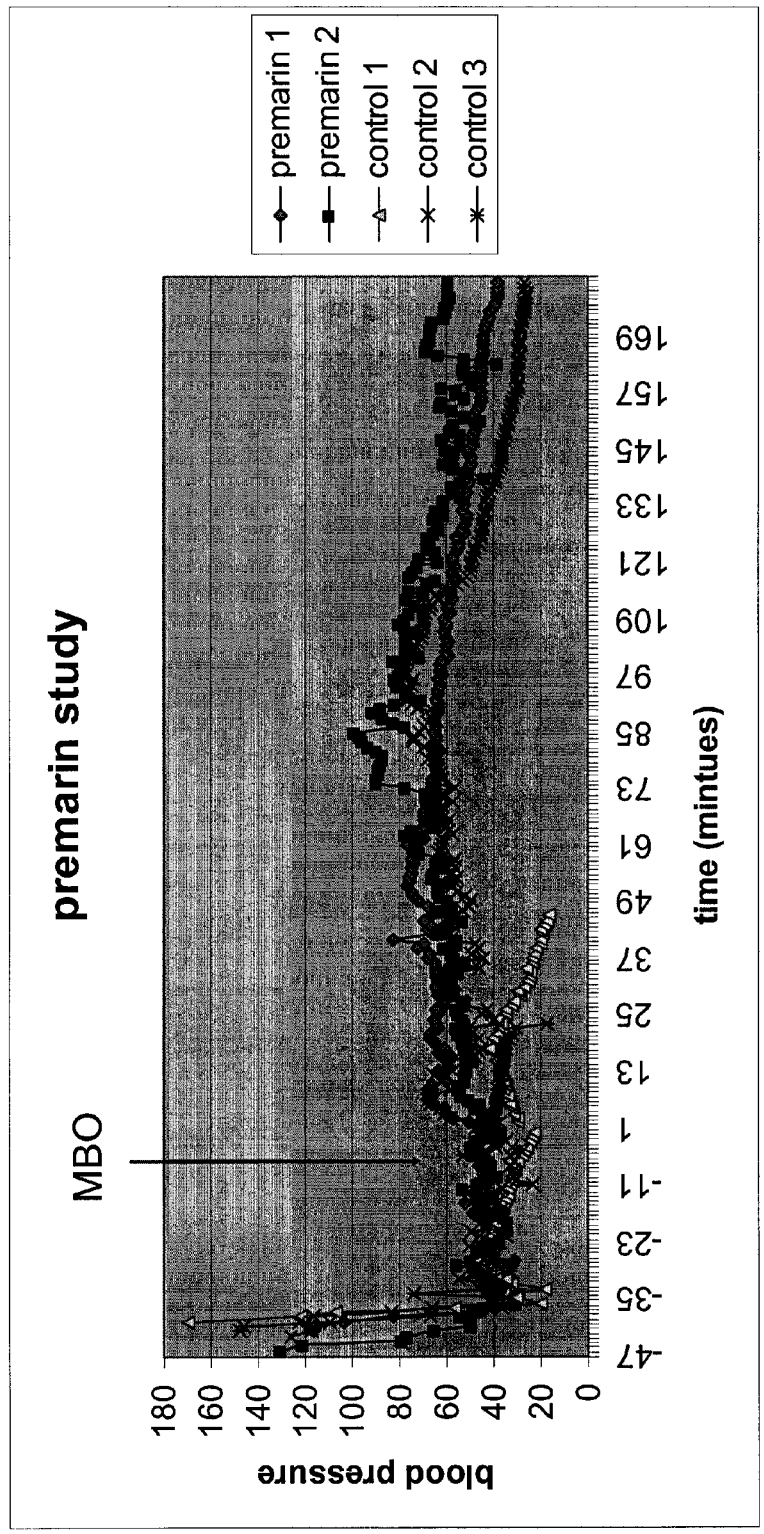
FIG. 25 shows the effect of Premarin™ on blood pressure over a time period of 3 hours. The mice exposed to estrogen had much higher blood pressure rates, indicating decreased morbidity and a reduction of other complications associated with trauma hemorrhage.
Figure 26:
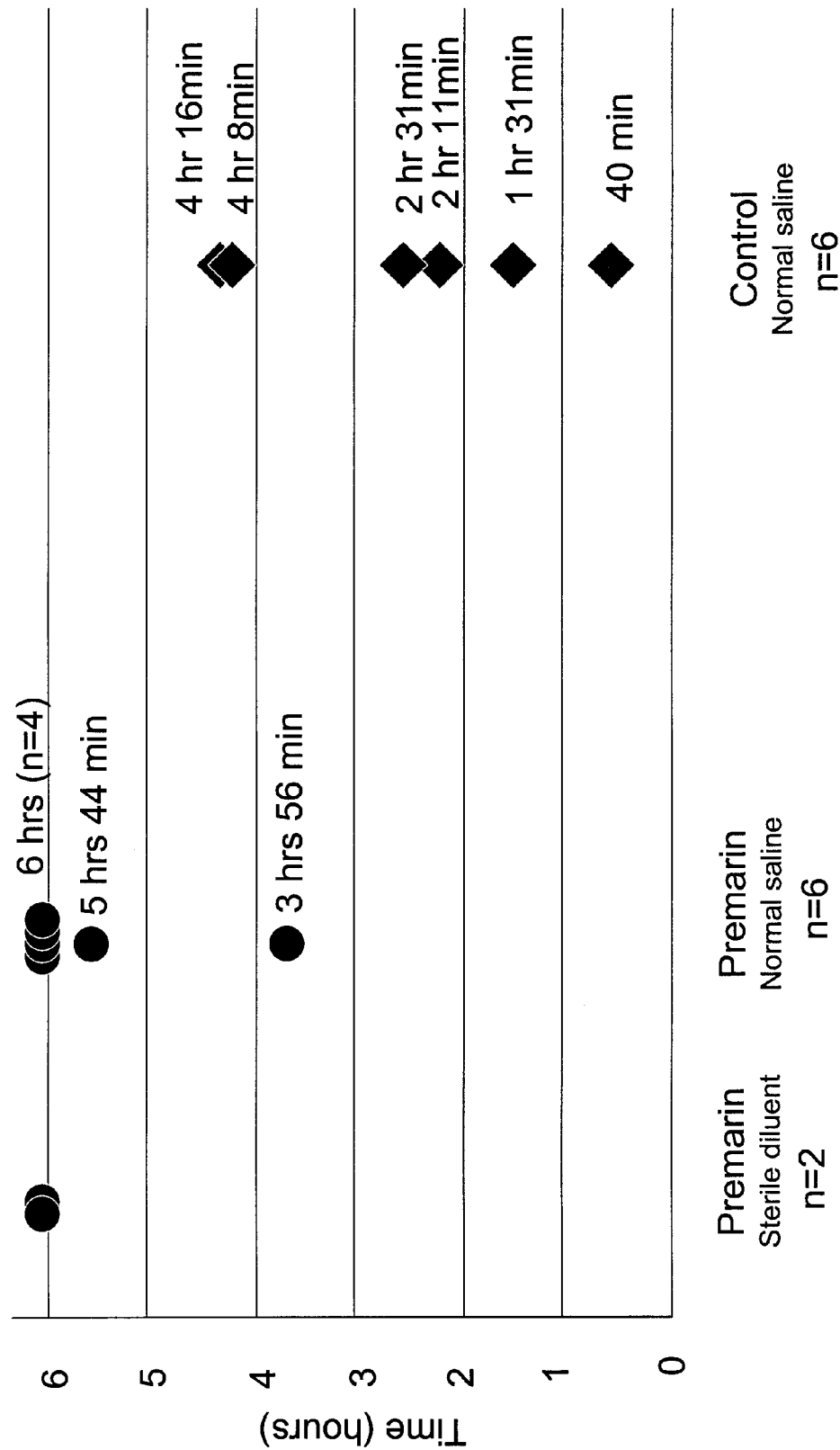
FIG. 26 shows a timeline of the longevity of mice exposed to Premarin™ or a control after three hours. The group of eight mice given Premarin™ includes two that were given Premarin™ in a sterile diluent, and six that were given Premarin™ in a normal saline solution. Six out of the eight given Premarin™ survived the entire six hours, with both of those mice given Premarin™ in a sterile diluent surviving the entire time. None of the control mice survived to the six hour mark.
Figure 27:
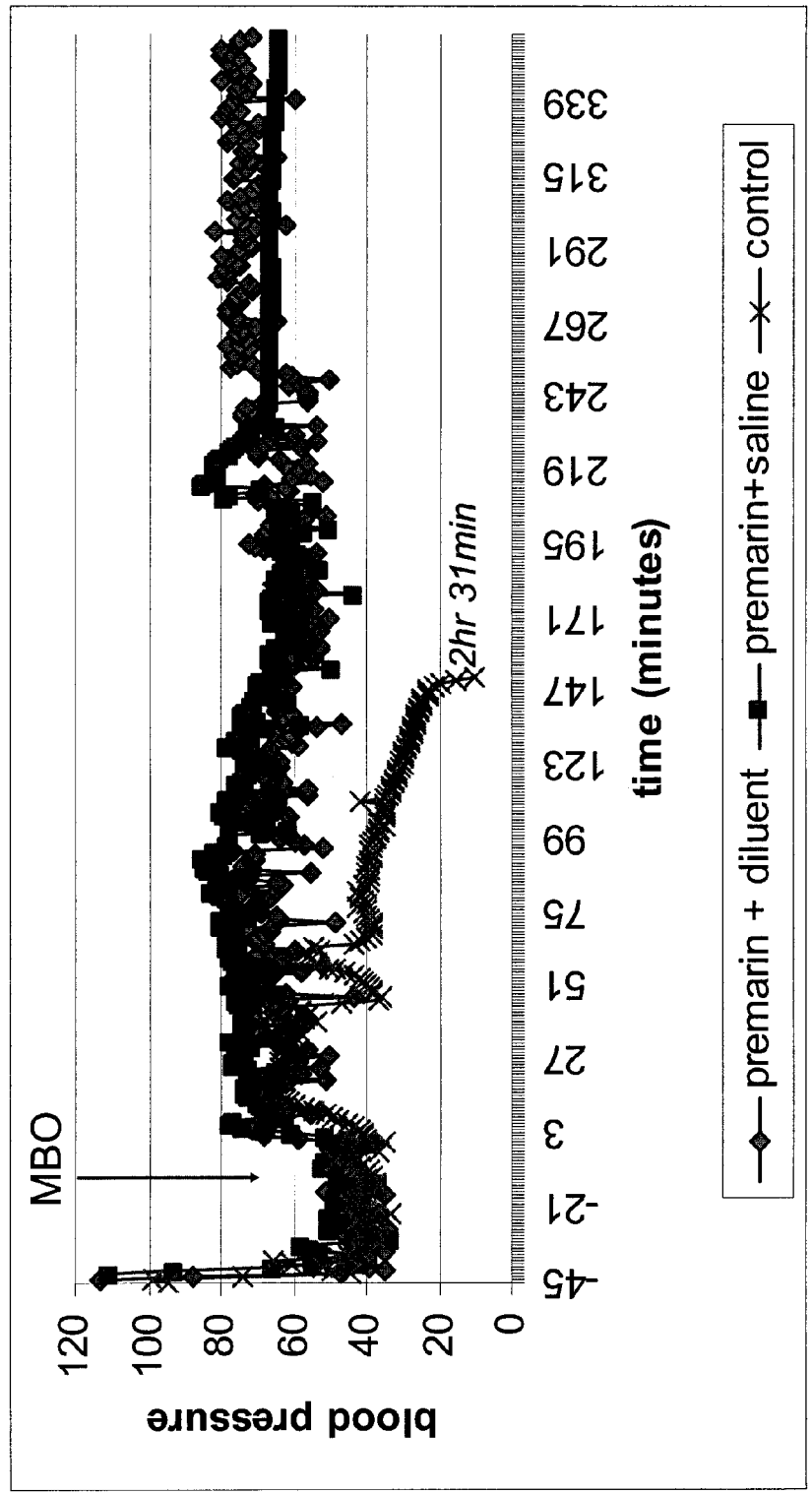
FIG. 27 shows the effect of Premarin™ on blood pressure over a time period of 6 hours. The mice exposed to estrogen had much higher blood pressure rates, indicating decreased morbidity and a reduction of other complications associated with trauma hemorrhage.
Figure 28:
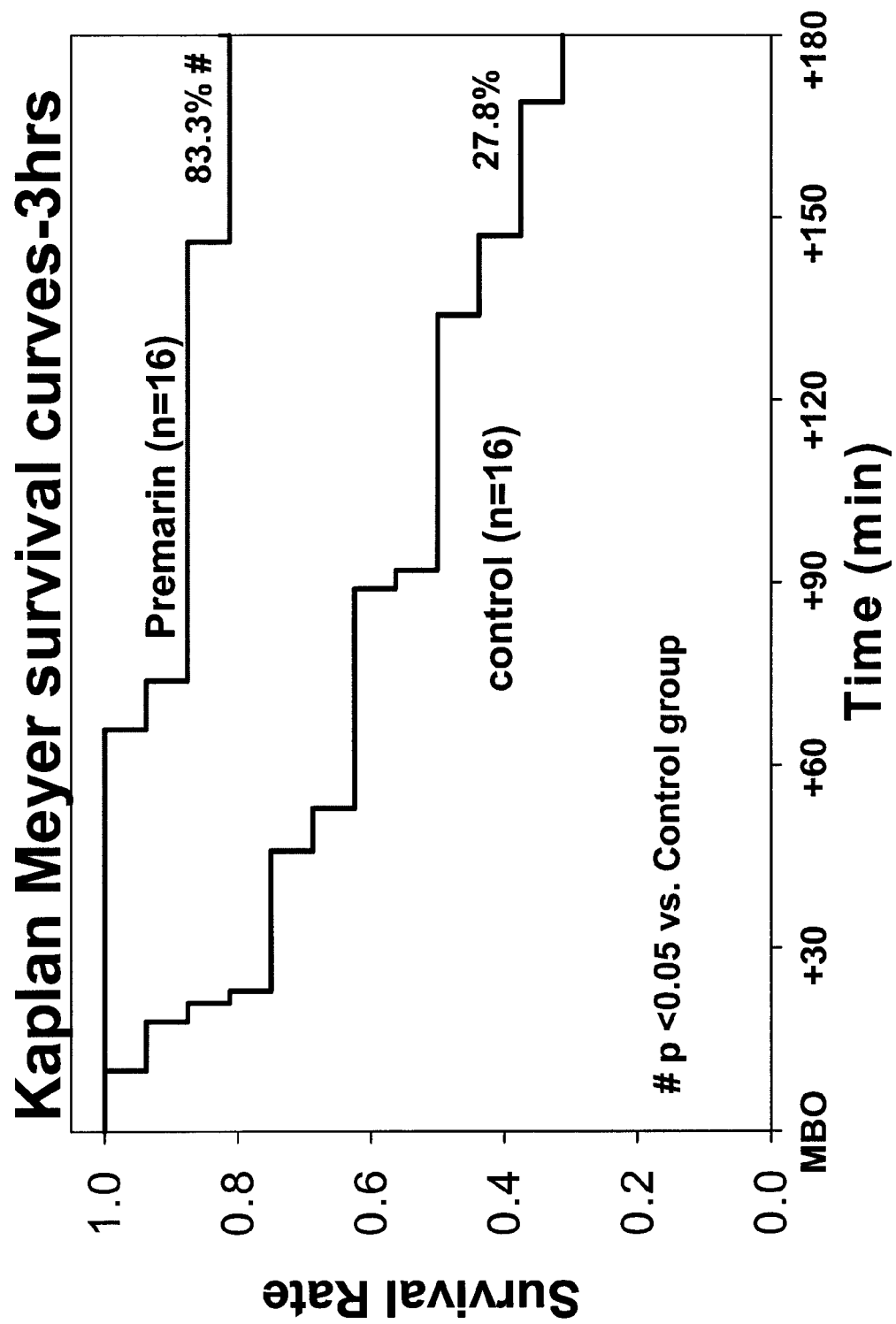
FIG. 28 shows Kaplan Meier curves for 3 hour survival. 83.3% of those mice exposed to Premarin™ survived to the 3 hour mark, while only 27.8% of the control mice survived.
Figure 29:
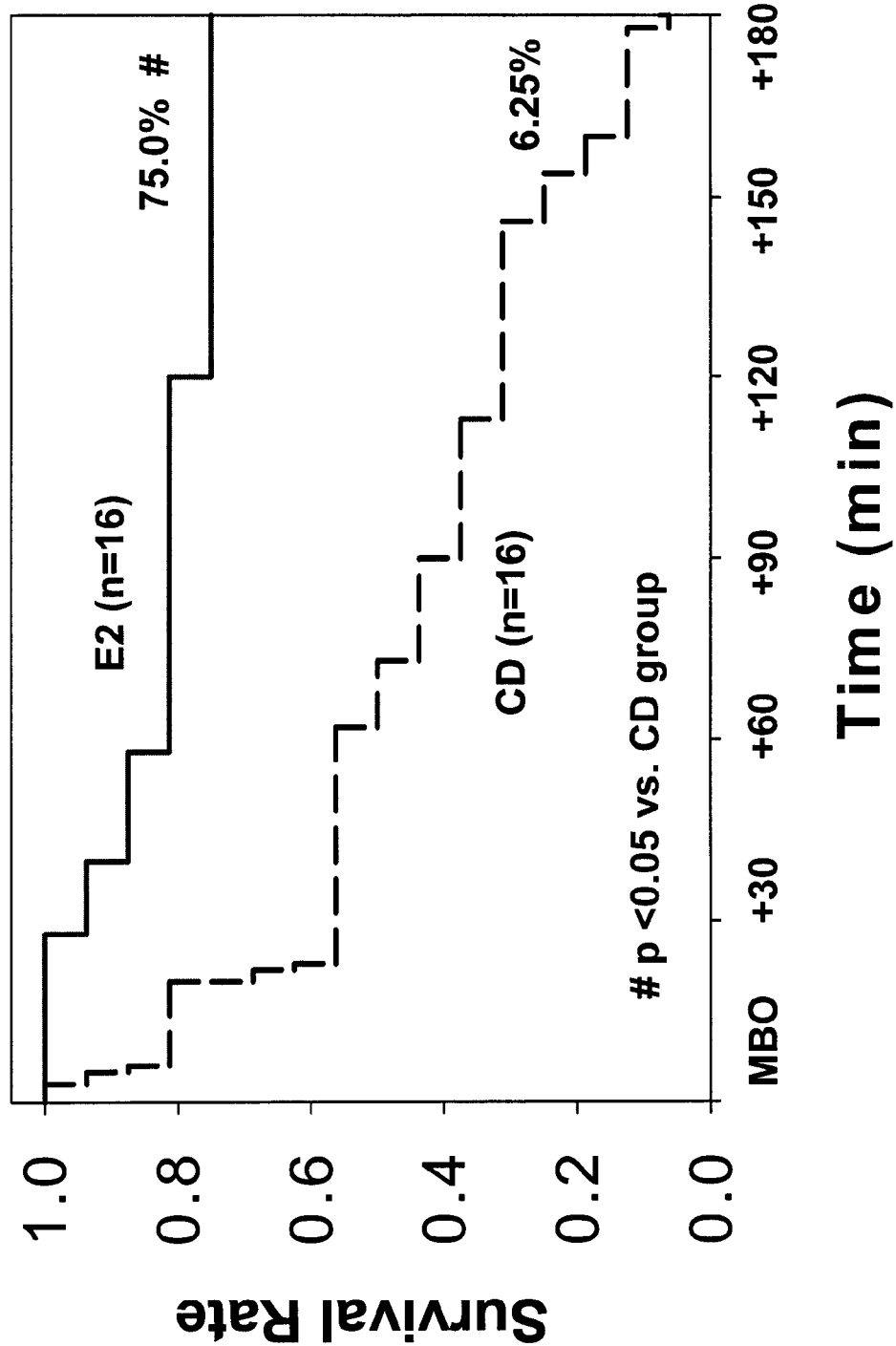
FIG. 29 shows Kaplan Meier curves for 3 hour survival. 75% of those mice exposed to cyclodextrin-microencapsulated 17β-estradiol survived to the 3 hour mark, while only 6.25% of the control mice survived.

The traumatic injury can involve a reduction in cellular ATP levels as compared to control ATP levels. By "control" is meant levels as measured before the traumatic injury, or levels that are considered in the "normal" range for the subject. Imaging and nuclear magnetic resonance studies have also been conducted to evaluate the effects of E2 on preservation of adenosine triphosphate (ATP) and pH levels in the liver. These in vivo studies have shown that estrogen-treated rats livers have preservation of intracellular ATP (see FIG. 22a, non-surviving cyclodextrin control and 22b, surviving estrogen-treated) as well as maintenance of pH near neutral (see FIG. 23). As can be seen in these figures, the converse is true for controls; ATP declines steadily until death, and pH likewise falls to sub-physiological acidic levels.

For example, using a variety of references, the best approximation of normal ATP levels is a range of ~2-10 fM/cell for ATP in eukaryotic cells, under "normal" conditions. Clearly, the intracellular ATP varies with the tissue per se and its state of metabolic activity, as well as with the actual system used for quantitative measurement. Intracellular pH varies in a similar fashion to blood pH, ranging from 7.2 under steady-state conditions, and down to 6.7 under pathological conditions of stress. ATP is exhausted in shock and severe stress due to the inability of the mitochondrion to produce sufficient ATP to cover demands. This failure can result from lowered oxygen supply, insufficient nutrient/substrate supply (i.e., glucose for oxidative phosporylation or lipid for β-oxidation), and tissue destruction, or a combination of the above. The cytokine milieu of the surrounding cells and tissues also has a profound effect on the production of ATP and the regulation of intracellular pH, and a highly proinflammatory cytokine microenvironment as exists with trauma and stress will greatly perturb ATP and pH levels.

The traumatic injury can also involve low blood pressure compared to a control blood pressure. By "control" is meant levels as measured before the traumatic injury, or levels that are considered in the "normal" range for the subject. For example, normal blood pressure is defined by the individual, and will vary with age, gender, overall health and fitness status, as well as emotional state. In general, it should be less than 120 mm Hg systolic and 80 mm Hg diastolic for adults. With trauma and blood loss, blood pressure falls from an average of 120/80 to dangerously low values. In shock there are three stages; stage I (compensated), stage II (progressive or decompensated) and stage III (irreversible). Our rat trials with estrogen are based on a loss of blood with a concomitant, documented loss of compensation, generally falling into the range of ~40 mm Hg mean arterial pressure. Because of the 3 hr duration of shock produced, rats may have entered a state which would result in stage III shock, which is supported by the fact that essentially all control animals die. However, the lowered vascular resistance afforded by estrogen, as well as the mitochondrial/energetic support which it provides, can moderate the tissue damage and risk of death from stage III shock.

The compositions disclosed herein can be used to treat very severe blood loss, also known as hemorrhagic shock. Hemorrhagic shock is a life-threatening condition brought on by severe blood loss. For example, hemorrhagic shock may originate from internal or external hemorrhage, gun shot wounds, severe trauma or any other condition associated with blood loss.

The initial phase of hemorrhagic shock, unless rapidly corrected, is followed by progressive tissue hypoxemia, end-organ dysfunction, and eventually producing refractory vascular failure and ischemia (total lack of oxygen). Hemorrhagic shock also is associated with early vasomotor paralysis and cardiovascular collapse. "Bleeding" or "hemorrhage" is defined as the loss of blood from the body. The complete loss of blood is referred to as exsanguination. The circulating blood volume is approximately 70 ml/kg of ideal body weight. Thus the average 70 kg (154 lbs) male has approximately 5000 ml (5.3 quarts) of circulating blood.

Hemorrhage generally becomes dangerous, or even fatal, when it causes hypovolemia (low blood volume) or hypotension (low blood pressure). In these scenarios various mechanisms come into play to maintain the body's homeostasis. These include the "retro-stress-relaxation" mechanism of cardiac muscle, the baroreceptor reflex and renal and endocrine responses such as the renin—angiotensin—aldosterone system (RAAS).

Certain diseases or medical conditions, such as hemophilia and low platelet count (thrombocytopenia) may increase the risk of bleeding or exacerbate minor bleeding. "Blood thinner" medications, such as warfarin can increase the risk of bleeding.

Hemorrhage is broken down into 4 classes by the American College of Surgeons' Advanced Trauma Life Support (ATLS). Class I Hemorrhage involves up to 15% of blood volume. There is typically no change in vital signs and fluid resuscitation is not usually necessary. Class II Hemorrhage involves 15-30% of total blood volume. Class III Hemorrhage involves loss of 30-40% of circulating blood volume. Class IV Hemorrhage involves loss of >40% of circulating blood volume. Disclosed herein is blood loss from a subject of 5, 10, 15, 20, 25, 30, 35, 40, 45, 50, 55, 60, 65, 70, 75, 80, 85, 90, or 95%, or any amount in between.

Traumatic bleeding, or "trauma," is defined as being caused by some type of injury. There are different types of wounds which may cause traumatic bleeding. These include, for example, laceration, incision, puncture wound, contusion, and gunshot wounds.

Medical bleeding is that associated with an increased risk of bleeding due to an underlying medical condition. It increases the risk of bleeding related to underlying anatomic deformities, such as weaknesses in blood vessels (aneurysm or dissection), arteriovenous malformation, ulcerations. Similarly, other conditions that disrupt the integrity of the body such as tissue death, cancer, or infection may lead to bleeding.

Certain medical conditions can also make patients susceptible to bleeding. These are conditions that affect the normal "hemostatic" functions of the body. Hemostasis involves several components. The main components of the hemostatic system include platelets and the coagulation system. Platelets are small blood components that form a plug in the blood vessel wall that stops bleeding. Platelets also produce a variety of substances that stimulate the production of a blood clot. One of the most common causes of increased bleeding risk is exposure to non-steroidal anti-inflammatory drugs (or "NSAIDs"). Deficiencies of coagulation factors can also be associated with clinical bleeding. For instance, deficiency of Factor VIII causes classic Hemophilia A while deficiencies of Factor IX cause "Christmas disease" (hemophilia B). Antibodies to Factor VIII can also inactivate the Factor VII and precipitate bleeding that is very difficult to control. This is a rare condition that is most likely to occur in older patients and in those with autoimmune diseases. von Willebrand disease is another common bleeding disorder. It is caused by a deficiency of or abnormal function of the "von Willebrand" factor, which is involved in platelet activation. The compositions disclosed herein can be used to treat bleeding accompanied by a medical condition, or bleeding that has been made more severe because of an underlying medical condition.

Ischemia is defined as an acute condition associated with an inadequate flow of oxygenated blood to a part of the body, caused by the constriction or blockage of the blood vessels supplying it. Ischemia occurs any time that blood flow to a tissue is reduced below a critical level. This reduction in blood flow can result from: (i) the blockage of a vessel by an embolus (blood clot); (ii) the blockage of a vessel due to atherosclerosis; (iii) the breakage of a blood vessel (a bleeding stroke); (iv) the blockage of a blood vessel due to vasoconstriction such as occurs during vasospasms and possibly, during transient ischemic attacks (TIA) and following subarachnoid hemorrhage. Conditions in which ischemia occurs, further include (i) myocardial infarction; and (ii) during cardiac, thoracic and neurosurgery (blood flow needs to be reduced or stopped to achieve the aims of surgery). During myocardial infarct, stoppage of the heart or damage occurs which reduces the flow of blood to organs, and ischemia results. Cardiac tissue itself is also subjected to ischemic damage. Disclosed herein is a method for treating severe blood loss or hemorrhaging, wherein the severe blood loss or hemorrhaging is not caused by ischemia.

Ischemia can also be defined as the total lack of blood flow, and hence oxygen availability. The term "hypoxemia" refers to a condition in which blood flow is markedly decreased but not entirely stopped, and thus some oxygen (although limited) is still available until blood flow completely stops. Thus, constriction of blood vessel will cause hypoxemia while blockage of blood vessel causes ischemia.

Also disclosed are methods of ameliorating the effects of an aortic cross clamp by administering estrogen as described herein. Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood. By administering estrogen as disclosed herein, the cell and organ viability is maintained, thereby increasing the patient's survival rate. For bypass surgery, the estrogen can be administered prior to, during, or after the surgery. Preferably, it will be administered just prior to the onset of cardiopulmonary bypass. It can also be given immediately after the removal of the cross clamp.

The traumatic injury can also involve an inflammatory response. Inflammation is a complex stereotypical reaction of the body expressing the response to damage of its cells and vascularized tissues. The main features of the inflammatory response are vasodilation, i.e. widening of the blood vessels to increase the blood flow to the infected area; increased vascular permeability, which allows diffusible components to enter the site; cellular infiltration by chemotaxis, or the directed movement of inflammatory cells through the walls of blood vessels into the site of injury; changes in biosynthetic, metabolic, and catabolic profiles of many organs; and activation of cells of the immune system as well as of complex enzymatic systems of blood plasma.

There are two forms of inflammation, acute and chronic. Acute inflammation can be divided into several phases. The earliest, gross event of an inflammatory response is temporary vasoconstriction, i.e. narrowing of blood vessels caused by contraction of smooth muscle in the vessel walls, which can be seen as blanching (whitening) of the skin. This is followed by several phases that occur over minutes, hours and days later. The first is the acute vascular response, which follows within seconds of the tissue injury and lasts for several minutes. This results from vasodilation and increased capillary permeability due to alterations in the vascular endothelium, which leads to increased blood flow (hyperemia) that causes redness (erythema) and the entry of fluid into the tissues (edema).

This can be followed by an acute cellular response, which takes place over the next few hours. The hallmark of this phase is the appearance of granulocytes, particularly neutrophils, in the tissues. These cells first attach themselves to the endothelial cells within the blood vessels (margination) and then cross into the surrounding tissue (diapedesis). During this phase erythrocytes may also leak into the tissues and a hemorrhage can occur. If the vessel is damaged, fibrinogen and fibronectin are deposited at the site of injury, platelets aggregate and become activated, and the red cells stack together in what are called "rouleau" to help stop bleeding and aid clot formation. The dead and dying cells contribute to pus formation. If the damage is sufficiently severe, a chronic cellular response may follow over the next few days. A characteristic of this phase of inflammation is the appearance of a mononuclear cell infiltrate composed of macrophages and lymphocytes. The macrophages are involved in microbial killing, in clearing up cellular and tissue debris, and in remodeling of tissues.

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that, while specific reference of each various individual and collective combinations and permutation of these compounds may not be explicitly disclosed, each is specifically contemplated and described herein. For example, if a particular vector is disclosed and discussed and a number of modifications that can be made to a number of places within the vector can be made, including the portion encoding the reporter or the promoter, as well as the portion encoding the secreted protein, are discussed, specifically contemplated is each and every combination and permutation of the promoter, the reporter and/or the secreted protein, and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

There are various types of estrogen that can be used with the methods disclosed herein. For example, the estrogen can be 17β-estradiol. The estrogen can be delivered in a cyclodextrin complex. It has been found that there is a grea improvement of the stability of estrogen by combining it with cyclodextrin (U.S. Pat. No. 7,163,931, herein incorporated by reference in its entirety for its teaching concerning estrogen). There are various types of cyclodextrin that can be used with the methods disclosed herein. For example, the cyclodextrin complex can comprise 2-hydroxypropyl-β-cyclodextrin. The size of the cyclized dextrin ring (i.e., number of glucose molecules in the ring) determines the suitability for a particular mass and shape of "guest molecule." In this instance, β-cyclodextrin, a 7 glucose polymer, can be used for maximum efficiency. Furthermore, the hydroxypropyl derivative of this molecule can also be used.

As the person skilled in the art will appreciate, the estrogen can be selected from the group consisting of, for example, ethinyl estradiol (EE), estradiol, estradiol sulfamates, estradiol valerate, estradiol benzoate, estrone, estriol, estriol succinate and conjugated estrogens, including conjugated equine estrogens such as estrone sulfate, 17β-estradiol sulfate, 17α-estradiol sulfate, equilin sulfate, 17β-dihydroequilin sulfate, 17α-dihydroequilin sulfate, equilenin sulfate, 17β-dihydroequilenin sulfate and 17α-dihydroequilenin sulfate or mixtures thereof. Particularly interesting estrogens are selected from the group consisting of ethinyl estradiol (EE), estradiol, estradiol sulfamates, estradiol valerate, estradiol benzoate, estrone, and estrone sulfate or mixtures thereof, notably ethinyl estradiol (EE), estradiol, estradiol valerate, estradiol benzoate and estradiol sulfamates. Also included are Premarin® and derivatives thereof. Furthermore, it should be noted that any of the above estrogens can be rendered water soluble as described herein.

The cyclodextrin can be selected from, for example, α-cyclodextrin, β-cyclodextrin, γ-cyclodextrin and derivatives thereof. Another example of cyclodextrin is sulfobutyl ether cyclodextrin. The cyclodextrin may be modified such that some or all of the primary or secondary hydroxyls of the macrocycle, or both, may be alkylated or acylated. Thus, some or all of the hydroxyls of cyclodextrin may modified cyclodextrins have be substituted with an O—R group or an O—C(O)—R, wherein R is an optionally substituted C (1-6) alkyl, an optionally substituted C (2-6) alkenyl, an optionally substituted C (2-6) alkynyl, an optionally substituted aryl or heteroaryl group. Thus, R may be methyl, ethyl, propyl, butyl, pentyl, or hexyl group. Consequently, O—C(O)—R may be an acetate. Furthermore, with the commonly employed 2-hydroxyethyl group, or 2-hydroxypropyl group R may be used to derivatize cyclodextrin. Moreover, the cyclodextrin alcohols may be per-benzylated, per-benzoylated, or benzylated or benzoylated on just one face of the macrocycle, or wherein only 1, 2, 3, 4, 5, or 6 hydroxyls are benzylated or benzoylated. Naturally, the cyclodextrin alcohols may be per-alkylated or per-acylated such as per-methylated or per-acetylated, or alkylated or acylated, such as methylated or acetylated, on just one face of the macrocycle, or wherein only 1, 2, 3, 4, 5, or 6 hydroxyls are alkylated or acylated, such as methylated or acetylated. Preferably, the complex comprises of beta-cyclodextrin or a derivative thereof, most preferably beta-cyclodextrin.

The estrogen-cyclodextrin complex can be obtained by methods known to the person skilled in the art (e.g. U.S. Pat. No. 5,798,338, herein incorporated by reference in its entirety for its teaching concerning estrogen-cyclodextrin complexes).

The estrogen-cyclodextrin complex can be delivered in a solvent, such as ethanol, methanol, or DMSO, for example. This can be used with hydrophobic forms of estrogen. For example, U.S. Pat. No. 720,035 (hereby incorporated by reference in its entirety) teaches DMSO and dimethylacetamide can be used to deliver hydrophobic drugs intravenously.

Disclosed herein is the use of valerate as the form of estrogen. Valerate is an ester of estradiol, having similar uses and more prolonged action than the estradiol. It can be used intramuscularly or intravenously, for example. Valerate can be rendered water soluble as well.

The major forms of estrogen in Premarin® are estrone (>50%), equilin (15-25%) and equilenin. The estrogens in Premarin® are often called "conjugated equine estrogens" (CEE) because the estrogen molecules are generally present with hydrophilic side-groups attached such as sulfate. Thus, estrone sulfate is the major molecule in Premarin®. Premarin is widely used for hormone replacement therapy in the treatment of menopausal symptoms (Nelson et al. JAMA. 291, 1610-1620, 2004). It is available in both oral and injectable forms. Regarding the composition of Premarin®, the package insert states: "Premarin® (conjugated estrogens tablets, USP) for oral administration contains a mixture of conjugated equine estrogens obtained exclusively from natural sources, occurring as the sodium salts of water-soluble estrogen sulfates blended to represent the average composition of material derived from pregnant mares' urine. It is a mixture of sodium estrone sulfate and sodium equilin sulfate. It contains as concomitant components, as sodium sulfate conjugates, 17-dihydroequilin, 17-estradiol, and 17β-dihydroequilin." Sulfation of estrogen(s) represents a form of metabolic processing of hormones which renders it soluble for excretion, and hence facilitates its presence in urine. However, sulfated estrogens can represent a reservoir form of the molecule which enables storage in the blood (Qian et al. Endocrinology. 142, 5342-5350, 2001). Although estrogen sulfate has somewhat lower receptor binding properties, it remains biologically active. Premarin® has been shown to be a viable substitute for 17β-estradiol (E2), and that it has activity comparable to E2. A structural diagram of equilin sulfate appears below.

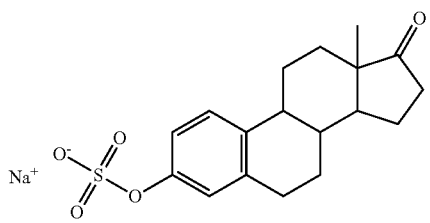 [SMILES: [Na+] ; CC12CCC3c4ccc(OS(=O)(=O)[O-])cc4CCC3C1CCC2=O]

a) Pharmaceutically Acceptable Carriers

Disclosed are compositions comprising estrogen and a pharmaceutical carrier. Pharmaceutical carriers are known to those skilled in the art. These most typically would be standard carriers for administration of drugs to humans, including solutions such as sterile water, saline, and buffered solutions at physiological pH. One example, discussed above, is cyclodextrin. The compositions can be administered intramuscularly or subcutaneously, but are preferably administered intravenously. The compounds can be administered according to standard procedures used by those skilled in the art.

Pharmaceutical compositions can also include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition can be administered in a number of ways depending on whether local or systemic treatment is desired, and on the area to be treated. Administration may be topically (including opthamalically, vaginally, rectally, intranasally), orally, sublingually, by inhalation, or parenterally, for example by intravenous drip, subcutaneous, intraosseous, intraperitoneal or intramuscular injection. As discussed above, a preferred mode of delivery is intravenous.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. As discussed above, one example of a solution to deliver the estrogen is cyclodextrin.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The dosage ranges for the administration of the compositions are those large enough to produce the desired effect of inflammation monitoring. The dosage should not be so large as to cause adverse side effects, such as unwanted cross-reactions, anaphylactic reactions, and the like. Generally, the dosage will vary with the age, condition, sex and extent of the injury in the patient and can be determined by one of skill in the art. Dosage can vary, and can be administered in one or more dose administrations daily, for one or several days However, this level of diagnosis is not needed if the patient is in need of immediate care. In one example, the estrogen can be administered in less than 10, 20, 25, 30, 40, 50, 60, 70, 75, 80, 90, 100, 110, 120, 130, 140, 150, 160, 170, 180, 190, 200, 210, 220, 230, 240, 250, 500, or 1000 mL of solution.

Estrogen levels vary within the menstrual cycle, and are diminished greatly after menopause. In premenopausal women, the range in blood is from 50-400 pg/ml. After menopause, the range is from 20-40 pg/ml. The level of estrogen in males is 12-34 pg/ml. E2 can be administered at a dose of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, or 5.0 or greater mg/kg. For example, in the treatment of acute uterine bleeding, 25 mg is given every 4 hr for 3 injections for a total of 75 mg, which would approximate an average of 70 mg of estrogen given to a 70 kg human male).

2. Kits

Disclosed herein are kits. Specifically disclosed is a kit comprising microencapsulated estrogen in a cyclodextrin complex. The estrogen can be presented as a reconstitutable dry powder or sterile solution, and can be in less than 10, 20, 30, 40, 50, 60, 70, 80, 90, 100, 110, 120, 130, 140, 150, 160, 170, 180, 190, 200, 210, 220, 230, 240, or 250 mL of vehicle. In one example, the estrogen can be in cyclodextrin. The estrogen in the kit can be in a syringe, for example. The kit can be in a bulletproof container. In one example, the kit can comprise a package comrpising at least two separate compartments, one of which contains sterile dried estrogen and the other contains diluent, such as cyclodextrin, for example. The contents of the compartments can then be combined by breaking a barrier or septum between the chambers and mixing the contents prior to injection.

3. Compositions with Similar Functions

It is understood that the compositions disclosed herein have certain functions, for example, the estrogen allows for increased chance of survival in response to trauma injury. Disclosed herein are certain structural requirements for estrogen and the carriers thereof, and it is understood that there are a variety of structures which can perform the same function which are related to the disclosed structures, and that these structures will ultimately achieve the same result, for example, treating traumatic injury as previously described.

D. EXAMPLES

1. Example 1

Female Sex Hormones Regulate Macrophage Function After Trauma-Hemorrhage and Prevent Increased Death Rate from Subsequent Sepsis Circulating female sex hormones were reduced by ovariectomy of 8-week-old female CBA/J mice. Two weeks afterward, ovariectomy and proestrus sham-ovariectomy mice were subjected to laparotomy (i.e., soft tissue trauma) and hemorrhagic shock (35±5 mm Hg for 90 minutes, then resuscitated) or sham operation. Two hours afterward, splenic and peritoneal MΦ and Kupffer cells were isolated and cytokine production was assessed. In a second series of experiments, animals were subjected to sepsis by cecal ligation and puncture at 24 hours after trauma-hemorrhage or sham operation, and survival was assessed.

Release of interleukin-1 and interleukin-6 by splenic and peritoneal MΦ from proestrus mice was maintained after trauma-hemorrhage, whereas release of interleukin-1 and interleukin-6 by M from ovariectomized mice was depressed by approximately 50%. In contrast, trauma-hemorrhage resulted in a fourfold increase of Kupffer cell release of tumor necrosis factor-alpha in ovariectomized females and a fivefold increase in plasma concentrations of tumor necrosis factor-alpha. Release of tumor necrosis factor-alpha and plasma concentrations were unchanged in proestrus mice under such conditions. When proestrus and ovariectomized animals were subjected to sepsis by cecal ligation and puncture at 24 hours after trauma-hemorrhage or sham operation, ovariectomized mice had a significantly higher death rate than proestrus mice.

These findings show that female sex hormones play a critical role in maintaining immune responses after trauma-hemorrhage by suppressing the elaboration of tumor necrosis factor-alpha and prevent the increased lethality from subsequent sepsis. Thus, female sex hormones may be a useful adjunct in preventing trauma-induced immunodepression and increased susceptibility to subsequent sepsis.

Methods

Animals

Inbred female CBA/J mice (Jackson Laboratories, Bar Harbor, Me.), 8 to 9 weeks old (24-26 g), were used in this study.

Experimental Groups

To determine the role of female sex hormones in the regulation of immune responses, ovariectomy or sham-ovariectomy was performed in female CBA/J mice 2 weeks before trauma-hemorrhage. Two weeks after ovariectomy or sham-ovariectomy, the animals were divided into four groups. Groups 1 and 2 consisted of sham-ovariectomy females in the proestrus state of the estrus cycle; this was determined by microscopic examination of vaginal cytology. Animals in groups 3 and 4 consisted of ovariectomized females. The animals in groups 1 and 3 served as sham-operated animals (neither hemorrhaged nor resuscitated). Animals in groups 2 and 4 were subjected to the trauma-hemorrhage procedure. Each group consisted of seven or eight animals. In additional studies, ovariectomy and sham-ovariectomy females were subjected to sepsis at 24 hours after trauma-hemorrhage and resuscitation or sham operation. In all experimental groups, polymicrobial sepsis was induced by cecal ligation and puncture (CLP), and survival was assessed for up to 10 days after the induction of sepsis. Each group consisted of 20 animals.

Trauma-Hemorrhage Procedure

Mice in the trauma-hemorrhage groups were lightly anesthetized with methoxyflurane (Metofane, Pitman Moore, Mundelein, Ill.) and restrained in a supine position, and a 2.5-cm midline laparotomy (i.e., soft tissue trauma induced) was performed. It was then closed aseptically in two layers using 6-0 Ethilon sutures (Ethicon, Inc., Somerville, N.J.). Both femoral arteries were then aseptically cannulated with polyethylene 10 tubing (Clay-Adams, Parsippany, N.J.) using a minimal dissection technique, and the animals were allowed to awaken. Blood pressure was constantly monitored by attaching one of the catheters to a blood pressure analyzer (Micro-Med, Inc., Louisville, Ky.). Lidocaine was applied to the incision sites to provide analgesia during the study period. On awakening, the animals were bled rapidly through the other catheter to a mean arterial blood pressure of 35±5 mm Hg (mean arterial blood pressure before hemorrhage was 95±5 mm Hg); this was maintained for 90 minutes. At the end of that procedure, the animals were resuscitated with four times the shed blood volume in the form of lactated Ringer's solution. The catheters were then removed, the vessels ligated, and the groin incisions closed. Sham-operated animals in groups 1 and 3 underwent the same surgical procedure, which included ligation of both femoral arteries, but neither hemorrhage nor fluid resuscitation was carried out. There were no deaths observed in this model of trauma-hemorrhage. The animals were killed by methoxyflurane overdose at 2 hours after trauma-hemorrhage and resuscitation to obtain the spleen, liver, peritoneal MΦ, uterus, and whole blood.

Cecal Ligation and Puncture Procedure

Polymicrobial sepsis was induced at 24 hours after trauma-hemorrhage and resuscitation using the CLP method described by Baker et al.19 Briefly, mice were anesthetized with methoxyflurane and a 2-cm midline laparotomy was performed. The cecum was isolated and ligated just below the ileocecal valve. The cecum was then punctured twice with a 22-gauge needle, a small amount of bowel contents was extruded through the puncture holes, and the cecum was returned to the peritoneal cavity. The abdominal incision was closed in two layers using 6-0 Ethilon sutures. Normal saline solution (20 mL/kg) was administered subcutaneously at that time. Previous studies have shown that blood cultures taken from mice after CLP are positive for gram-positive (e.g., *Streptococcus bovis*) as well as gram-negative (e.g., *Bacteroides fragilis*). (Watanakunakorn 1994).

Plasma Collection and Storage

Whole blood was obtained by cardiac puncture. Plasma was separated by centrifugation in pyrogen-free microcentrifuge tubes and samples were immediately frozen and stored (−80° C.) until assayed.

Preparation of Splenic and Peritoneal Macrophage Cultures

Spleens were harvested 2 hours after sham operation or trauma-hemorrhage aseptically, and splenic MΦ cultures were established as previously described (Zellweger 1996). Resident peritoneal MΦ were harvested at the same time and monolayers were established as previously described (Ayala 1990). These protocols provided peritoneal and splenic MΦ populations that were at least 95% positive for nonspecific esterase staining and exhibited typical MΦ morphology. Splenic and peritoneal MΦ monolayers (1×106 cells/mL) were stimulated with 10 μg lipopolysaccharide (from *E. coli* 055:B5, Difco Laboratories, Detroit, Mich.)/mL Click's medium containing 10% heat-inactivated fetal bovine serum (Gibco BRL, Grand Island, N.Y.) for 48 hours (at 37° C., 5% $CO_2$, and 90% humidity) to assess the cells' ability to release cytokines. The same lot of fetal bovine serum was used for all experiments to control for steroid content of the culture media. Culture supernatants were collected and stored at 80° C. until assayed for IL-1, IL-6, and IL-10.

Preparation of Kupffer Cell Cultures

Kupffer cells were harvested as previously described (Ayala 1992). In brief, retrograde perfusion of the liver was performed with 35 mL ice-cold Hank's balanced salt solution (HBSS, Ca2+/Mg2+free, 37° C., Gibco BRL) through the portal vein. This was immediately followed by perfusion with 10 mL 0.075% collagenase type IV (162 U/mg, Sigma Chemical Co., St. Louis, Mo.) in HBSS at 37° C. The liver was transferred to a petri dish containing warm 0.075% collagenase, minced finely, incubated at 37° C. for 10 minutes, and passed through a sterile 150-mesh stainless-steel screen into a beaker containing 10 mL cold HBSS and 10% fetal bovine serum. The cell suspension was then layered over 16% metrizamide (Accurate Chemical & Scientific Corp., Westbury, Ny.) in HBSS and centrifuged at 3,000 g, 4° C., for 45 minutes to separate the Kupffer cells from the remaining parenchymal cells in the pellet. After removal of the non-parenchymal cells from the interface with a Pasteur pipette, the cells were washed twice by centrifugation (800g, 15 minutes, 4° C.) with HBSS, and resuspended in Click's medium containing 10% fetal bovine serum. The cells were transferred to a 24-well plate that was precoated with 0.5 mL of 6-μg vitrogen 100 (Collagen Biomaterials, Collagen Corporation, Palo Alto, Calif.)/mL (plates were washed with phosphate-buffered saline three times before cell transfer) and incubated for 3 hours at 37° C. (5% $CO_2$, 90% humidity).

Nonadherent cells were then removed by washing three times with Click's medium. This protocol provides adherent cells that are more than 95% positive by nonspecific esterase staining and that exhibit typical MΦ morphology (Ayala 1992). The Kupffer cells (1.5×106 Kupffer cells mL-1 per well) were incubated for 24 hours (37° C., 5% CO2) with 10 μg lipopolysaccharide/mL Click's medium with 10% fetal bovine serum. Culture supernatants were collected and stored at 80° C. until assayed for tumor necrosis factor (TNF)-α, IL-1β, IL-6, and IL-10.

Assessment of 17β-Estradiol and Cytokine Concentrations

17β-estradiol plasma concentrations were determined using a commercially available radioimmunoassay (ICN Biomedicals, Costa Mesa, Calif.) as described by the manufacturer. Activity of IL-1β was determined by adding serial dilutions of plasma or supernatants to D10.G4.1 cells in the presence of Concanavalin A, as previously described (Ayala 1992). In certain experiments IL-1β was determined by enzyme-linked immunosorbent assay according to the manufacturer's recommendations (Genzyme Diagnostics, Cambridge, Mass.). Activity of IL-6 was determined by assessing the 72-hour proliferation of the IL-6-dependent murine hybridoma 7TD1 stimulated by serial dilutions of plasma or supernatant, as described previously (Ayala 1992). Activity of TNF-α was determined by the 24-hour cytotoxicity induced in WEHI-164 clone 13 cells in the presence of serial dilutions of plasma or supernatant, as described elsewhere. Concentrations of IL-10 were determined by enzyme-linked immunosorbent assay according to the manufacturer's recommendations (Pharmingen, San Diego, Calif.).

Statistical Analysis

Data are presented as mean standard error. One-way analysis of variance followed by the Student-Newman-Keuls test as a post hoc test for multiple comparisons was used to determine the significance of the differences between experimental means. A t test was used to determine the significance of differences in 17β-estradiol plasma concentrations and uterine wet weight between proestrus and ovariectomized mice. To determine the significance of the differences between death rates in the survival study, a z test was used. $P<0.05$ was considered significant.

Results

Biologic Effect of Ovariectomy

At 2 weeks after ovariectomy, plasma concentrations of 17β-estradiol were significantly lower in ovariectomized females compared with sham-ovariectomy females in the proestrus state of the estrus cycle (22.5±2.9 vs. 10.0±1.9 pg/mL; mean±SEM of seven or eight mice per group). Uterine wet weight was also significantly lower in ovariectomized females compared with sham-ovariectomy females (63.9±12.6 vs. 19.5±3.4 mg).

Macrophage Interleukin-1 Release

Splenic MΦ IL-1 release was significantly increased in proestrus sham-ovariectomy females after trauma-hemorrhage ($P<0.05$ vs. sham-operated proestrus females; FIG. 1). In ovariectomized females, splenic MΦ IL-1 release was significantly depressed after trauma-hemorrhage ($P<0.05$ vs. sham-operated ovariectomized females). Similar changes in peritoneal MΦ IL-1 release were observed. In contrast to splenic and peritoneal MΦ, hepatic MΦ (Kupffer cell) IL-1 release was not significantly increased in proestrus females after trauma-hemorrhage. In ovariectomized females, however, Kupffer cell IL-1 release was significantly increased ($P<0.05$) approximately 2.5-fold in animals that underwent trauma-hemorrhage compared with ovariectomy shams.

Macrophage Interleukin-6 Release

Figure 2:
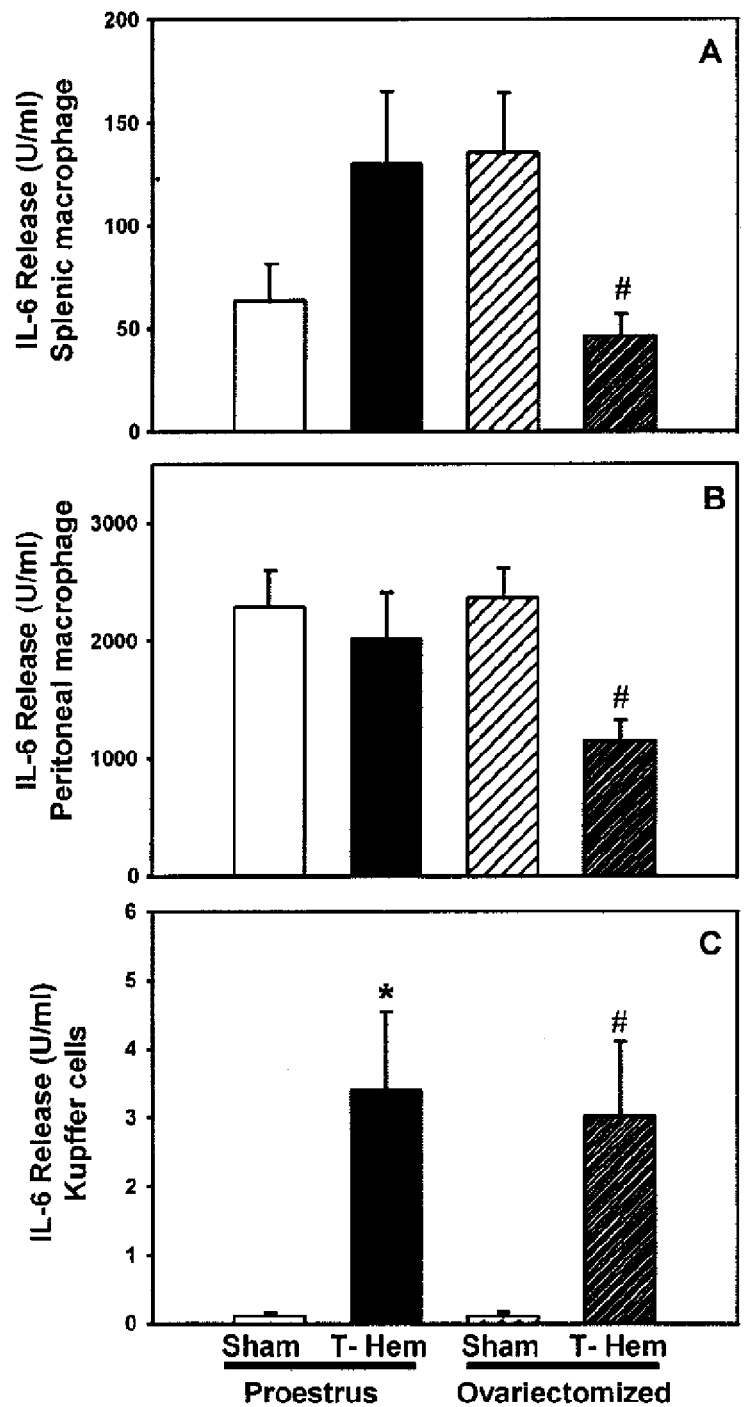
FIG. 2 shows the release of interleukin-6 (IL-6) by splenic macrophages (A) or peritoneal macrophages (B) and Kupffer cells (C) at 2 hours after sham operation or trauma-hemorrhage. Values are means±SEM of seven or eight animals per group; analysis of variance, $*p<0.05$ vs. proestrus sham; $\#p<0.05$ vs. ovariectomy sham.

Splenic MΦ IL-6 release was significantly increased (P<0.05) in proestrus females after trauma-hemorrhage compared with their corresponding shams, whereas in ovariectomized females IL-6 production was significantly depressed (P<0.05) under such conditions (FIG. 2). Peritoneal MΦ IL-6 release after trauma-hemorrhage was unchanged in proestrus females compared with their corresponding shams. In ovariectomized females, however, peritoneal MΦ IL-6 release was significantly depressed in hemorrhaged animals versus sham-operated animals (P<0.05). Kupffer cell IL-6 release significantly increased after trauma-hemorrhage in proestrus and ovariectomized females (P<0.05). No differences were observed in post-trauma-hemorrhage Kupffer cell IL-6 release between proestrus and ovariectomized females.

Macrophage Interleukin-10 Release

Figure 3:
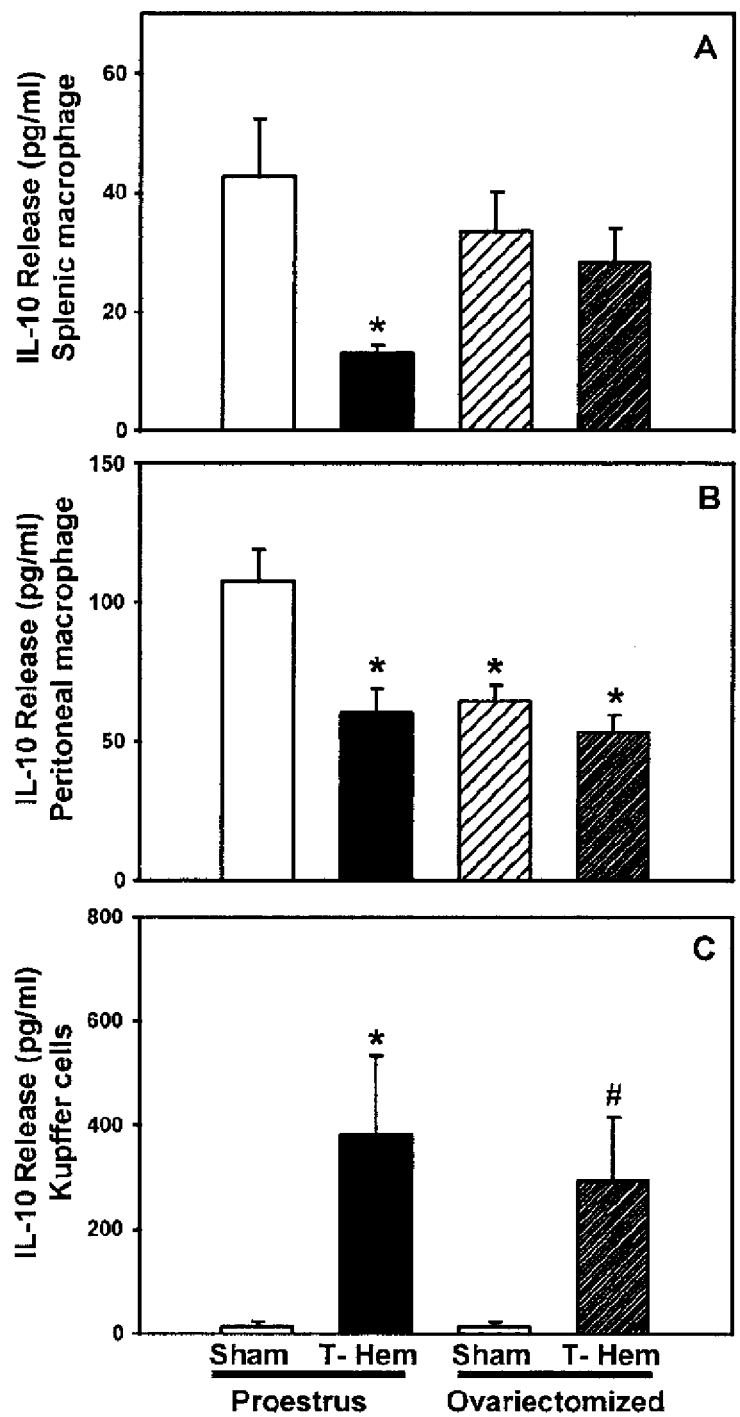
FIG. 3 shows the release of interleukin-10 (IL-10) by splenic macrophages (A) or peritoneal macrophages (B) and Kupffer cells (C) at 2 hours after sham operation or trauma-hemorrhage. Values are means±SEM of seven or eight animals per group; analysis of variance, $*p<0.05$ vs. proestrus sham; $\#p<0.05$ vs. ovariectomy sham.

Production of IL-10 by splenic MΦ was significantly reduced in proestrus females at 2 hours after trauma-hemorrhage (FIG. 3; P<0.05). In contrast, IL-10 release by splenic MΦ from ovariectomized females was not different from that in sham animals. Similar changes were observed in peritoneal MΦ, with the exception that ovariectomy significantly reduced IL-10 release independent of trauma-hemorrhage. After trauma-hemorrhage, Kupffer cell IL-10 release was significantly increased in proestrus and ovari ectomized females to a similar extent (P<0.05).

Kupffer Cell Tumor Necrosis Factor

Figure 4:
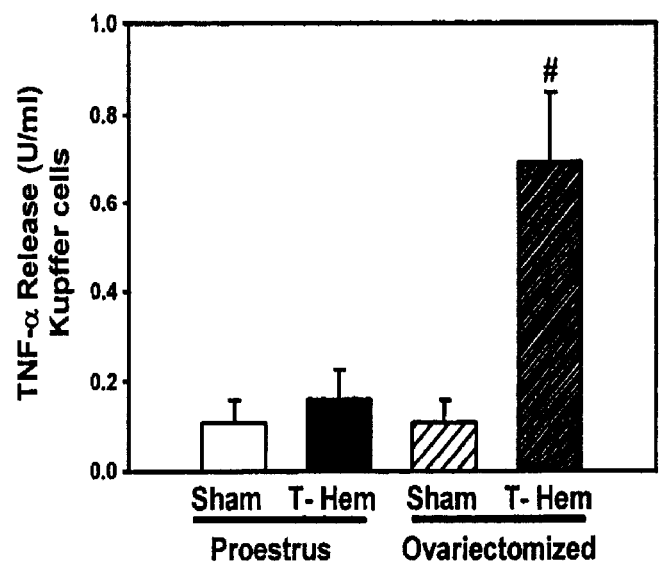
FIG. 4 shows the release of tumor necrosis factor (TNF-α) by Kupffer cells at 2 hours after sham operation or trauma-hemorrhage (T-Hem). Kupffer cells were cultured in the presence of 10 μg/mL lipopolysaccharide for 24 hours. Values are means±SEM of seven or eight animals per group; analysis of variance, $\#p<0.05$ versus ovariectomy sham.

In proestrus females, a slight but insignificant increase in Kupffer cell TNF-α release was observed after trauma-hemorrhage, whereas TNF-α release by Kupffer cells from ovariectomized females subjected to trauma-hemorrhage was increased approximately sevenfold compared with ovariectomy shams (FIG. 4; P<0.05).

Plasma Concentrations of Interleukin-6 and Tumor Necrosis Factor

Figure 5:
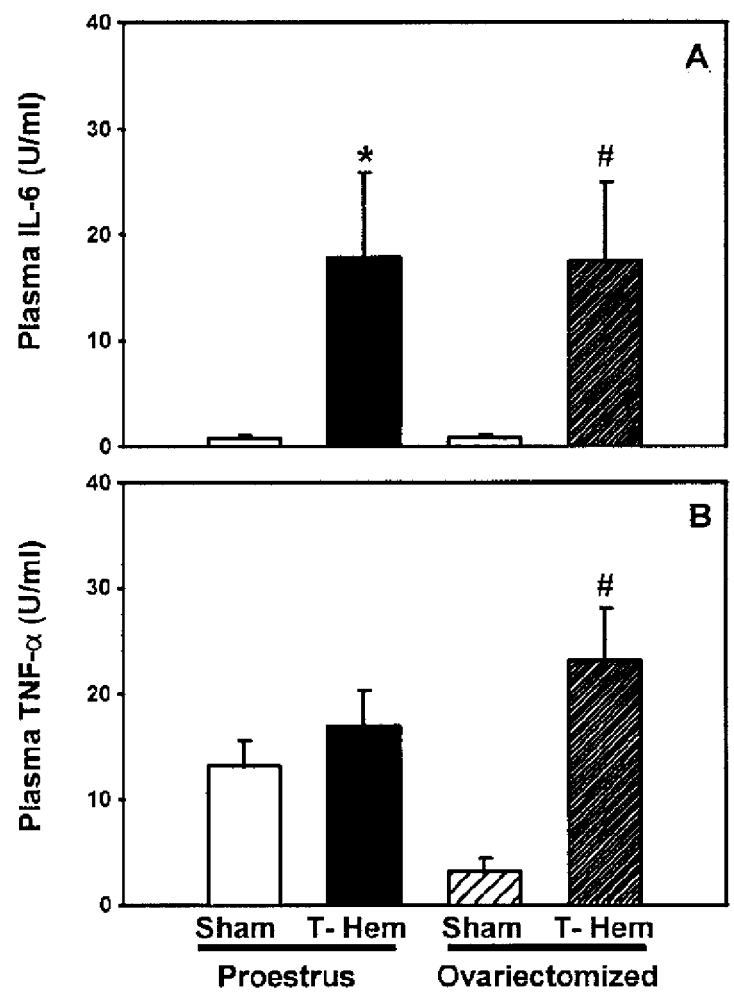
FIG. 5 shows plasma concentrations of (A) interleukin-6 (IL-6) and (B) tumor necrosis factor (TNF-α) at 2 hours after sham operation or trauma-hemorrhage. Values are means±SEM of seven or eight animals per group; analysis of variance, $*p<0.05$ vs. proestrus sham; $\#p<0.05$ vs. ovariectomy sham.

At 2 hours after trauma-hemorrhage, a significant increase in plasma concentrations of IL-6 in proestrus and ovariectomized females was observed (FIG. 5; P<0.05). There was no significant difference in plasma concentrations of IL-6 between proestrus females and ovariectomized females after trauma-hemorrhage. Trauma-hemorrhage did not increase plasma TNF-α concentrations in proestrus females, but in ovariectomized females TNF-α concentrations were significantly increased (P<0.05) approximately six-fold after trauma-hemorrhage.

Survival from Subsequent Sepsis

Figure 6:
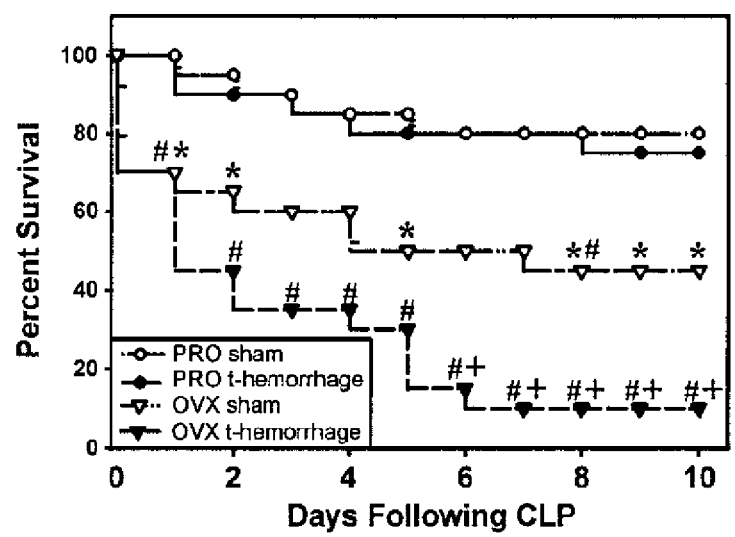
FIG. 6 shows ten-day survival of sham or trauma-hemorrhage mice after the induction of sepsis by cecal ligation and puncture (CLP). z test; $*p<0.05$ vs. proestrus sham; $\#p<0.05$ vs. proestrus trauma-hemorrhage; $p<0.05$ vs. ovariectomy sham; n=20 per group. PRO, proestrus; OVX, ovariectomy.

The results of the trauma-hemorrhage and subsequent sepsis experiment are shown in FIG. 6. No difference was observed in the death rates of proestrus females that underwent trauma-hemorrhage or sham operation 24 hours before the induction of sepsis. However, in ovariectomized females, the death rate of sham-operated animals subjected to sepsis was significantly higher than that of proestrus shams (P<0.05). Further, from postoperative day 6, the death rate of ovariectomized females that underwent trauma-hemorrhage before sepsis induction was significantly higher than that of the sham-operated ovariectomized females (P<0.05).

Discussion

The differences in systemic sex hormone levels between proestrus and ovariectomized females are associated with profound alterations in the immunologic response to trauma-hemorrhage. These results indicate that females in the proestrus state had increased splenic and peritoneal MΦ proinflammatory cytokine production after trauma-hemorrhage. However, in ovariectomized females, trauma-hemorrhage resulted in depressed splenic and peritoneal MΦ proinflammatory cytokine production under such conditions.

Because ovariectomy led to a depression of MΦ IL-1 and IL-6 production after trauma-hemorrhage, it appears that physiologic levels of female sex steroids are involved in the regulation of MΦ proinflammatory cytokine production. The depression of splenic and peritoneal MΦ function seen in ovariectomized females after trauma-hemorrhage is comparable to the depression observed in males under such conditions, indicating that the presence of male sex steroids (i.e., testosterone) and the reduction of female sex steroids produce comparable immunodepressive effects on MΦ under such conditions.

Ovariectomy, independent of trauma-hemorrhage, altered splenic and peritoneal MΦ cytokine production, consistent with studies by Deshpande et al. showing the suppressive effects of 17β-estradiol on splenic MΦ IL-1 and IL-6 production. The observed increase in proinflammatory cytokine production by splenic MΦ from ovariectomized females is most likely due to the decrease in systemic 17β-estradiol levels. The divergent responses observed between sham and trauma-hemorrhage animals support the concept that hormonal regulation of immune function in a traumatized host differs substantially from the regulation under normal conditions. The anti-inflammatory cytokine IL-10 has previously been identified as an important immunosuppressant of cell-mediated immune functions (Howard et al. 1992) and has been implicated in the suppression of splenocyte immune functions after trauma-hemorrhage (Ayala 1992). Female sex hormones suppress IL-10 production by splenic and peritoneal MΦ after trauma-hemorrhage, thereby allowing maintained production of proinflammatory mediators.

These results also indicate that Kupffer cell IL-1β and TNF-α release increased in ovariectomized females after trauma-hemorrhage, whereas no difference was seen in proestrus females. The activation of Kupffer cell TNF-α production in ovariectomized females was associ-ated with significantly increased circulating concentrations of TNF-α after trauma-hemorrhage, whereas plasma TNF-α remained at sham concentrations in proestrus females. Pre-vious studies have implicated TNF-α as an important me-diator in the immune depression after trauma-hemorrhage.30

The absence of a systemic TNF-α response in proestrus females after trauma-hemorrhage can in part explain the lack of immune depression and increased susceptibility to subsequent sepsis. There was no difference in Kupffer cell IL-6 production and plasma IL-6 concentrations between proestrus and ovariectomized females after trauma-hemorrhage; this can be related to the early time point used in this study. The elevation in plasma IL-6 concentrations after trauma-hemorrhage is more protracted than that of TNF-α (Schwacha 1992).

There was no difference in the death rates of proestrus females that underwent trauma-hemorrhage or sham operation before the induction of sepsis. In contrast, the death rate of ovariectomized females that underwent trauma-hemorrhage before induction of sepsis was higher than that of sham-operated ovariectomized females. Thus, physiologic levels of female sex steroids appear to prevent an increased death rate from sepsis in females after trauma-hemorrhage. The death rate of ovariectomized sham-operated animals was significantly higher than that of proestrus shams, further supporting a protective role for female sex hormones after sepsis.

2. Example 2

The Female Reproductive Cycle is an Iimportant Variable in the Response to Trauma-Hemorrhage Although immune functions in proestrus females are maintained after hemorrhage as opposed to decreased responses in males, it has previously been unknown whether such a sexual dimorphism also exists with regard to cardiovascular and hepatocellular functions under those conditions. To study this, male and female (estrus and proestrus) rats underwent a 5-cm midline laparotomy and were bled to and maintained at a mean blood pressure of 40 mmHg until 40% of the maximal bleed-out volume was returned in the form of Ringer lactate (RL). Rats were then resuscitated with four times the shed blood volume with RL. At 24 h thereafter, cardiac index; heart performance; hepatocellular function; and plasma estradiol, testosterone, and prolactin levels were measured. Cardiovascular and hepatocellular functions were depressed in males and estrus females (p<0.05) but were not depressed in proestrus females after resuscitation. Plasma estradiol and prolactin levels were highest in proestrus females (p<0.05), whereas males had high testosterone and the lowest estradiol levels (p<0.05). Thus the female reproductive cycle is an important variable in the response to hemorrhage.

Materials and Methods

Experimental procedures. The previously described non-heparinized model of trauma-hemorrhage in the rat (Chaudry 1996; Wang 1999) was used with minor modifications. Briefly, age-matched adult male and female Sprague-Dawley rats (males, 275-325 g; females, 200-250 g; Charles River Laboratories, Wilmington, Mass.) were fasted overnight before the experiment but were allowed water ad libitum. The stage of the female reproductive cycle was determined by regular examination of the vaginal smears by the same examiner. Proestrus was defined when both leukocytes and nucleated epithelial cells in approximately equal numbers were present on the vaginal smears. Estrus was characterized by large, squamous-type epithelial cells without nuclei. In female rats, experiments were performed only after at least one complete estrus cycle had been documented. The cycle phase was determined from the cytology of vaginal smears obtained daily at 0700-0830. The hemorrhage procedure began between 0900 and 1000. The rats were anesthetized by methoxyflurane (Mallinckrodt Veterinary, Mundelein, Ill.) inhalation, and catheters were placed in both femoral arteries and the right femoral vein [polyethylene (PE-50) tubing; Becton-Dickinson, Sparks, Md.]. After catheterization of the first femoral artery, ~600 ml of blood were withdrawn as described below (see Plasma collection and storage). After this, a 5-cm midline laparotomy representing soft-tissue trauma was performed. The abdomen was then closed in layers, and the wounds were bathed with 1% lidocaine (Elkins-Sinn, Cherry Hill, N.J.) throughout the surgical procedure to reduce postoperative pain. Rats were then bled to and maintained at a mean arterial pressure (MAP) of 40 mmHg until the animals could not maintain a MAP of 40 mmHg unless extra fluid in the form of Ringer lactate was given. This time was defined as maximum bleed out, and the amount of withdrawn blood was noted. After this, the rats were maintained at a MAP of 40 mmHg until 40% of the maximum bleed-out volume was returned in the form of Ringer lactate. The animals were then resuscitated with four times the volume of the withdrawn blood over 60 min with Ringer lactate. The shed blood was not used for resuscitation. The catheters were then removed, the vessels were ligated, and the skin incisions were closed with sutures. Sham-operated animals underwent the same groin dissection, which included the ligation of both femoral arteries and the right vein; however, neither hemorrhage nor resuscitation was carried out.

After the rats were returned to their cages, they were allowed food and water ad libitum. At 24 h after the completion of fluid resuscitation or sham operation, the animals were anesthetized with methoxyflurane and then catheterized via the right jugular vein. During the monitoring of MAP and heart rate, pentobarbital sodium (25-30 mg/kg body wt) administration was carefully carried out to keep animals in a state of depressed sensibility. After each bolus injection of pentobarbital, several minutes passed before heart rate and MAP reached steady-state levels.

Measurement of cardiac output. A 2.4-French fiberoptic catheter was placed into the right carotid artery, which was connected to an in vivo hemoreflectometer (Hospex Fiberoptics, Chestnut Hill, Mass.) as described previously (Wang 1991). Indo-cyanine green (ICG; Cardio Green, Becton-Dickinson) solution was injected via the catheter in the jugular vein (1 mg/ml aqueous solution as a 50-ml bolus). Twenty ICG concentra-tions per second were recorded for ~30 s with the aid of a data-acquisition program (Asystant1; Asyst Software, Rochester, N.Y.). The area under the ICG dilution curve was then determined to calculate cardiac output (CO). CO was then divided by the body weight to determine cardiac index.

Measurement of hepatocellular function. Hepatocellular function was measured by the in vivo ICG clearance technique. ICG was administered by bolus injection (50 ml) of 1, 2, and 5 mg/ml ICG in aqueous solvent. The arterial concentration of ICG was recorded each second for 5 min. After this, the initial velocity of ICG clearance for each dose was calculated after performance of a nonlinear regression of the ICG clearance curves according to an e-raised second-order polynomial function (Wang 1990). The initial velocities of ICG clearance were then plotted against the ICG doses according to the methods of Lineweaver-Burk (Hauptmann 1991). This results in a straight line, allowing for the determination of a maximum of ICG clearance (maximal velocity; Vmax) and the Michaelis-Menten constant (Km). In this active hepatocellular membrane transport system, Vmax represents the functional hepatocyte ICG receptors, and Km represents the efficiency of the active transport process (Wang 1990).

Measurement of in vivo heart performance. After the determination of CO and hepatocellular function, the fiberoptic catheter in the right carotid artery was replaced with PE-50 tubing, which was manually stretched to reduce the outer diameter by ~50%. Under pressure control, this catheter was carefully advanced into the left ventricle. The position of the catheter was confirmed by recording of the characteristic left ventricle pressure curve. Data were analyzed from an in vivo heart performance analyzer (Micro-Med, Louisville, Ky.). Left ventricular performance parameters such as the maximal rate of pres-sure increase (1 dP/dtmax) and decrease (2 dP/dtmax) were documented with a data acquisition system (DMSI 200-8, Micro-Med).

Determination of circulating blood volume. Circulating blood volume (CBV) was determined by use of an in vivo ICG clearance technique as described previously (27). CBV in milliliters was calculated according to CBV 5 ICG dose (0.1 mg)/[ICG]0 3 1.000 where [ICG]0 is the ICG concentration at baseline, and CBV in milliliters per 100 g body wt was then calculated.

Plasma collection and storage. At the start of the experiments, 600 ml of heparinized whole blood for the determination of baseline hormone levels were withdrawn and replaced with 2.4 ml of Ringer lactate. At the end of all measurements (i.e., 25 h after the end of trauma-hemorrhage and resuscitation), heparinized whole blood was obtained. Blood was placed in microcentrifuge tubes and then centrifuged at 16,000 rpm for 15 min at 4° C. Plasma and serum were separated, placed in pyrogen-free microcentrifuge tubes, immediately frozen, and stored until assay.

Determination of plasma sex steroids. Plasma testosterone was determined with the use of a commercially available coated-tube RIA kit (Diagnostic Systems, Webster, Tex.) according to the manufacturer's instructions. Cross-reactivity of the RIA was as follows: 100% for testosterone; 3.4% for 5α-dihydrotestosterone; 2.2% for 5α-androstane-3α,17β-dio 2% for 11-oxotestosterone; and ~1% for all other steroids. Plasma 17β-estradiol concentration was determined with the use of a commercially available RIA kit specifically designed for rats and mice (ICN Biomedicals, Costa Mesa, Calif.). Cross-reactivity of the RIA was 100% for 17β-estradiol and 20% or 1.51% for estrone or estriol, respectively. For all other steroids, the cross-reactivity was ~0.01%.

Determination of plasma prolactin levels. Prolactin levels were measured by use of an enzyme immunosorbent assay kit (SPI Bio, Massy Cedex, France) according to the manufacturer's instructions. Cross-reactivity with rat luteinizing hormone, growth hormone, and thyroid-stimulating hormone is below 1%. The sensitivity of the assay is 0.5 ng/ml, and the mean interassay variation is 14%. The intra-assay coefficient of variation is 9.4 and 8.6% in the lower and higher range, respectively.

Statistical analysis. Results are presented as means 6 SE. One-way ANOVA and Student-Newman-Keuls test for multiple comparisons were used, and the differences were considered significant at $p<0.05$. There were 8, 6, and 6 animals in the sham-operated male, estrus, and proestrus groups, respectively, and 7, 8, and 8 animals in the male, estrus, and proestrus hemorrhaged groups, respectively.

Results

Figure 7:
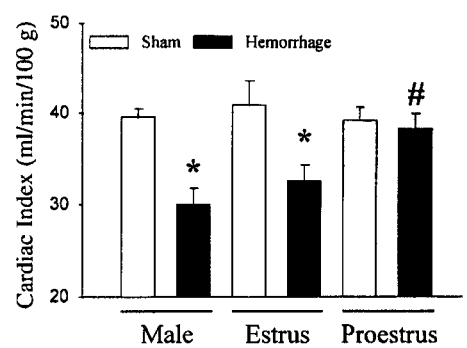
FIG. 7 shows effects of trauma-hemorrhage on cardiac index in rats at 24 h after resuscitation, as measured by an indocyanine green (ICG) dilution technique: comparison of sham-operated and hemorrhaged male and female (estrus and proestrus) rats (n 5 6-8/group). $*p<0.05$ vs. respective sham and $\#p<0.05$ vs. male trauma-hemorrage.

Effects of trauma-hemorrhage on cardiac index. The results in FIG. 7 indicate that cardiac index was similar in the three groups of sham-operated animals (male, 39.5±0.9; estrus, 40.9±2.7; and proestrus, 39.2±1.5 ml z min-1·100 g-1). In male and estrus female hemorrhaged animals, cardiac index decreased by 24.1 and 20.5% (30.0±1.8 and 32.6±1.7 ml·min-1·100 g-1; $p<0.05$ compared with the corresponding shams), respectively. However, cardiac index in hemorrhaged proestrus female rats was similar to the respective sham group at 24 h after the completion of fluid resuscitation (38.3±1.7 ml·min-1·100 g-1).

Figure 8:
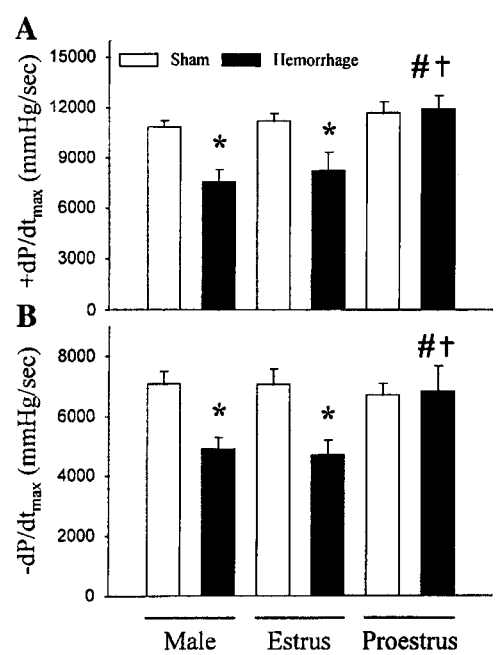
FIG. 8 shows the effects of trauma-hemorrhage on the maximal rate of pressure increase (1 dP/dtmax; A) and decrease (2 dP/dtmax; B) in the left ventricle at 24 h after resuscitation: comparison of sham-operated and hemorrhaged male and female (estrus and proestrus) rats (n=6-8/group). $*p<0.05$ vs. respective sham, $\#p<0.05$ vs. male trauma-hemorrhage, and † $p<0.05$ vs. estrus female trauma-hemorrhage.

Effects of trauma-hemorrhage on heart performance. The 1 dP/dtmax (male, 10,858±357; estrus, 11,224±428; and proestrus, 11,713±691 mmHg/s) and 2 dP/dtmax (male, 7,085±429; estrus, 7,067±511; and proestrus, 6,728±380 mmHg/s) in the left ventricle were similar in the three groups of sham animals (FIGS. 8, A and B). At 24 h after trauma-hemorrhage and crystalloid resuscitation, the 1 dP/dtmax in the left ventricle was decreased by 30.2 and 26.7% (7,585±732 and 8,235±1,131 mmHg/s; $p<0.05$ compared with the corresponding shams) in male and female estrus rats, respectively (FIG. 8A). In contrast, the values for 1 dP/dtmax in posthemorrhaged female proestrus rats were similar to the respective sham animals (11,971±812 mmHg/s) and were significantly higher than in hemorrhaged males and estrus females. In a similar fashion, the 2 dP/dtmax in the left ventricle was also diminished in male and female estrus rats after trauma-hemorrhage (4,915±377 and 4,711±492 mmHg/s, respectively; $p<0.05$ compared with the corresponding shams). In female proestrus animals, however, 2 dP/dtmax was maintained at the level of sham-operated animals (6,852±6 846 mmHg/s) and was significantly higher than in male and female estrus animals after trauma-hemorrhage.

Figure 9:
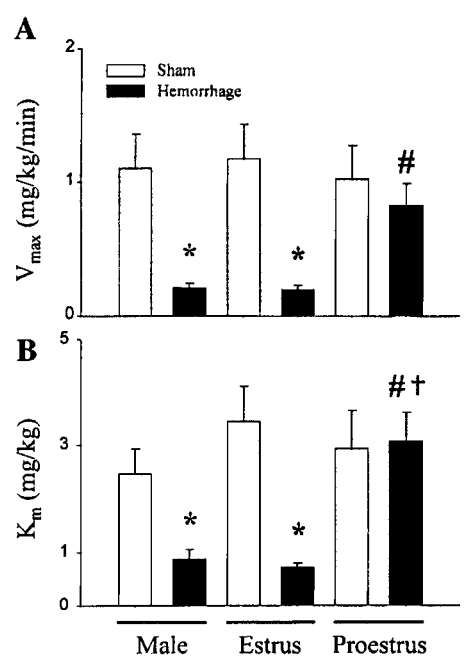
FIG. 9 shows the effects of trauma-hemorrhage on the active hepatocellular function at 24 h after resuscitation as measured by the in vivo ICG clearance technique: comparison of sham-operated and hemorrhaged male and female (estrus and proestrus) rats (n=6-8/group). A: Vmax represents the maximum velocity of ICG clearance. B: Michaelis-Menton constant (Km) represents the overall efficiency of the ICG transport. $*p<0.05$ vs. respective sham, $\#p<0.05$ vs. male trauma-hemorrhage, and † $p<0.05$ vs. estrus female trauma-hemorrhage.

Effects of trauma-hemorrhage on hepatocellular function. No significant difference in the Vmax of ICG clearance was evident between the sham animals (male, 1.1±0.2; estrus, 1.2±0.3; and proestrus, 1.0±21·min-1; FIG. 9A). In male and estrus fe-0.2 mg·kg male rats subjected to trauma-hemorrhage and resuscitation, Vmax decreased by 80.1 and 83.2% (0.21±0.03 and 0.19±0.03 mg·kg-1·min-1), respectively, compared with the corresponding sham groups ($p<0.05$). In contrast, proestrus female rats had significantly higher values for Vmax (0.83±0.16 mg·kg-1·min-1 24 h after crystalloid resuscitation. As indicated in FIG. 9B, Km was similar in the three groups of sham-operated animals (male, 2.5±0.5; estrus, 3.4±0.7; and proestrus, 2.9±0.7 mg/kg) and decreased by 64.9 and 79.8% (0.8±0.2 and 0.7±0.08 mg/kg) in male and estrus female rats, respectively, compared with the corresponding sham groups at 24 h after trauma-hemorrhage and resuscitation ($p<0.05$). In contrast, Km was significantly higher in hemorrhaged proestrus female animals (3.0±0.5 mg/kg) compared with male and estrus female rats ($p<0.05$).

Effects of trauma-hemorrhage on CBV. CBV was found to be 6.51±0.18, 6.56±0.38, and 6.81±0.29 ml/100 g in male and female prosetrus animals, respectively. At 24 hours after trauma-hemorrhage and crystalloid resuscitation, CBV was significantly decreased in all three groups (4.61±0.19, 4.8±0.29, and 4.9±0.39 ml/100 g in male and estrus and proestrus female rats, respectively; $p<0.05$) compared with the respective sham animals, with no significant difference between the hemorrhaged groups.

Figure 11:
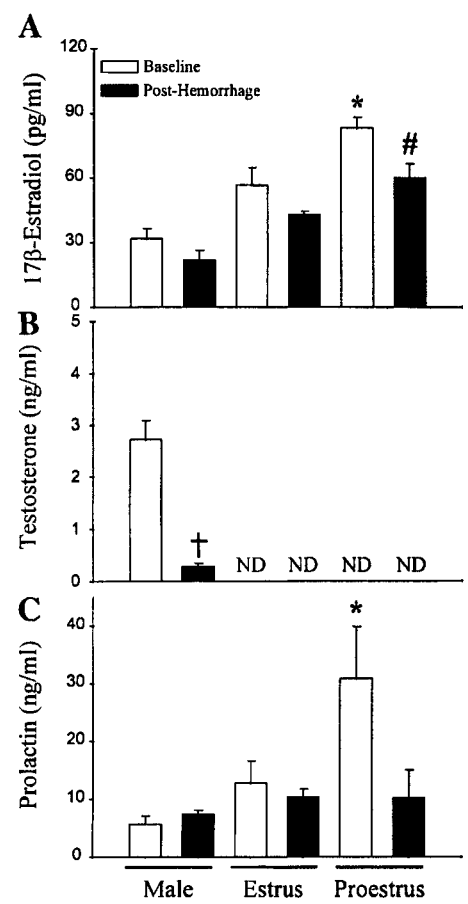
FIG. 11 shows circulating plasma levels of 17β-estradiol (A), testosterone (B), and prolactin (C) in male and female rats during different stages of the reproductive cycle at the start of the experiment and at 24 h after trauma-hemorrhage and crystalloid resuscitation (n=6-8/group). ND, not detectable. $*p<0.05$ vs. baseline male/estrus female, $\#p<0.05$ vs. male/estrus female trauma-hemorrhage, and † $p<0.05$ vs. baseline male.

Plasma estradiol levels. Plasma levels of estradiol were found to be the highest in proestrus female animals (83±5 pg/ml; FIG. 11A) and were significantly lower in male (32±5 µg/ml) and estrus female (56±8 pg/ml) rats at the start of the experiments ($p<0.05$).

At 24 h after trauma-hemorrhage and crystalloid resuscitation, plasma estradiol levels decreased by 31.2, 23.5, and 27.4% (21±5, 43±1.3, and 60±6 pg/ml) in male and estrus and proestrus female animals, respectively, with a higher plasma concentration in proestrus females compared with the other two hemorrhaged groups ($p<0.05$).

Plasma testosterone levels. Plasma levels of testosterone were found to be 2.7±0.36 ng/ml in male rats at the start of the experiments and decreased by 89.5% (0.28±0.06 ng/ml; $p<0.05$) at 24 h after the completion of crystalloid resuscitation (FIG. 11B).

Plasma prolactin levels. Plasma levels of prolactin were found to be the highest in proestrus female rats (30.8±9.0 ng/ml; FIG. 11C) and were lower in males (5.7±1.4 ng/ml; $p<0.05$) and estrus females (12.7±3.85 ng/ml; $p<0.05$) at the start of the experiment. There was no significant difference in plasma prolactin concentration at 24 h after trauma-hemorrhage and crystalloid resuscitation among the three groups.

Effects of gender on body weight, total CBV, hematocrit, maximal bleed-out volume, and hemorrhage time.

TABLE 1

Comparision between male and female estrus and proestrus rats:

| | Males | Female Estrus | Female Proestrus |
|---|---|---|---|
| Body wt, g | 318 ± 6.1*† | 223 ± 4.5 | 226 ± 4.9 |
| Total CBV, ml | 18.3 ± 0.5*† | 14.2 ± 0.7 | 15.4 ± 0.5 |
| Hct, % | 45.8 ± 1.1* | 40.6 ± 1.4 | 43.5 ± 1.1 |
| MBO, ml | 10.4 ± 0.37*† | 7.7 ± 0.23 | 7.5 ± 0.22 |
| Hemorrhage time, min | 90.5 ± 1.8 | 91.1 ± 0.5 | 90.8 ± 0.6 |

Figure 10:
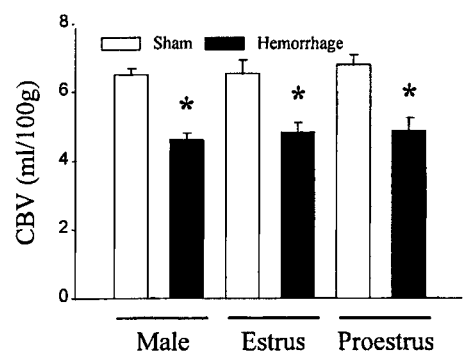
FIG. 10 shows the effects of trauma-hemorrhage on circulating blood volume (CBV) at 24 h after resuscitation: comparison of sham-operated and hemorrhaged male and female (estrus and proestrus) rats (n=6-8/group). CBV was determined by use of an in vivo ICG clearance technique, which does not require blood sampling. $*p<0.05$ vs. respective sham.

Data are means 6 SE. Total CBV, total circulating blood volume from FIG. 10; Hct, systemic hematocrit; MBO, maximal bleed-out volume; hemorrhage time, total time in shock until start of resuscitation. For further details, see materials and methods. Data were compared by 1-way ANOVA and Student-Newman-Keuls test. * p < 0.05 vs. female estrus and † p < 0.05 vs. female proestrus.

Data are means 6 SE. Total CBV, total circulating blood volume from FIG. 10; Hct, systemic hematocrit; MBO, maximal bleed-out volume; hemorrhage time, total time in shock until start of resuscitation. For further details, see materials and methods. Data were compared by 1-way ANOVA and Student-Newman-Keuls test.

As shown in Table 1, age-matched male rats had a significantly higher body weight than female animals. Similarly, total CBV was higher in males (p<0.05). Systemic hematocrit was 45.8±1.1% in the male group and was lower in female estrus (40.6±1.4%; p<0.05) and proestrus animals (43.5±1.1%). Maximal bleed-out volume (MBO) was also significantly higher in males compared with both female groups because of the higher body weight of male rats (Table 1). There was no significant difference in the time until 40% of the MBO volume was returned in the form of Ringer lactate in the three groups.

Discussion

It was found that cardiac output, heart performance parameters, and hepatocellular function, as determined by ICG clearance technique, are significantly depressed in male and female estrus rats at 24 h after trauma and severe hemorrhagic shock. In female proestrus animals, however, organ functions were not significantly different compared with their respective sham group, i.e., female rats undergoing sham operation on the morning of the proestrus phase of the reproductive cycle. Moreover, the data indicate that the normalized cardiac and hepatic functions in proestrus female animals were associated with peak levels of estradiol and prolactin at the start of the experiment, whereas male and female estrus rodents had significantly lower plasma levels of estradiol and prolactin. Although plasma levels of prolactin were similar in all three groups at 24 h after crystalloid resuscitation, it appears that the high levels of prolactin found in proestrus females before the onset of trauma-hemorrhage have salutary effects on organ functions under those conditions.

The data demonstrate that ovarian and gonadal sex steroids as well as the anterior pituitary hormone prolactin are associated with the gender-dimorphic response to trauma and severe blood loss. Although 17β-estradiol levels were higher in female estrus animals than in males at the start of the experiment, it appears that this was not sufficient to protect organ functions after trauma-hemorrhage. For the determination of plasma hormone levels, each animal served as its own control, because blood samples were obtained at baseline, i.e., before the midline laparotomy and onset of blood loss, and at 24 h after trauma-hemorrhage and crystalloid resuscitation. Although testosterone was undetectable in the plasma of females in the present study, the biologically more active form, 5α-dihydrotestosterone, has been found also in female rodents. However, because the measurement of 5α-dihydrotestosterone requires larger volumes of blood samples and an extraction procedure because of cross-reactivity of the antibody with other steroids, measurement of 5α-dihydrotestosterone was not performed.

It appears that not only low levels of estrogens but also high levels of male sex steroids are responsible for the depression of organ functions after hemorrhagic shock. In this regard, implantation of testosterone-releasing pellets in female mice caused a significant decrease in plasma levels of 17β-estradiol and a marked depression in immune functions as observed in male rodents, whereas vehicle-treated proestrus females maintained their immune responsiveness under those conditions (Chaudry 1992).

In the present experiments males were included for the following reasons. First, males, unlike females, have consistently low levels of estrogens with very little fluctuation over a period of time. Second, the surge in estradiol and prolactin in the morning of proestrus in female rats does explain only partially the sexual dimorphism in the response to trauma and severe blood loss. It appears that in males, not only the lack of such an increase in estradiol and prolactin but also the high levels of testosterone are responsible for the depression in organ functions after trauma-hemorrhage (Ayala 1991; Ertel 1991; Ertel 1994).

In summary, the results indicate that female proestrus rats have normalized organ functions at 24 h after trauma-hemorrhage, whereas male and female estrus animals show a marked depression in cardiovascular and hepatocellular functions. The maintenance of cardiac and hepatic functions after severe blood loss is associated with high levels of 17β-estradiol and prolactin.

3. Example 3

Estradiol Administration After Trauma-Hemorrhage Improves Cardiovascular and Hepatocellular Functions in Male Animals Studies indicate that gender difference exists in the immune and cardiovascular responses to trauma-hemorrhage, and that male sex steroids appear to be responsible for producing immune and organ dysfunction, but it was previously unknown if sex steroids produce any salutary effects on the depressed cellular and organ functions in males following trauma and hemorrhage.

Adult male Sprague-Dawley rats underwent a midline laparotomy (i.e., trauma induction), and were bled to and maintained at a mean arterial pressure of 40 mmHg until 40% of the maximum bleed-out volume was returned in the form of Ringer's lactate (RL). Animals were then resuscitated with RL at 4 times the shed blood over 60 minutes. 17β-Estradiol (50 mg/kg) or an equal volume of vehicle was injected subcutaneously 15 minutes before the end of resuscitation. The maximal rate of ventricular pressure increase or decrease (6 dP/dtmax), cardiac output, and hepatocellular function (i.e., maximal velocity and overall efficiency of in vivo indocyanine green clearance) were assessed at 24 hours after hemorrhage and resuscitation. Plasma levels of interleukin (IL)-6 were also measured.

Left ventricular performance, cardiac output, and hepatocellular function decreased significantly at 24 hours after trauma-hemorrhage and resuscitation. Plasma levels of IL-6 were elevated. Administration of 17β-estradiol significantly improved cardiac performance, cardiac output, and hepatocellular function, and attenuated the increase in plasma IL-6 levels.

Administration of estrogen appears to be a useful adjunct for restoring cardiovascular and hepatocellular functions after trauma-hemorrhage in male rats.

Severe hemorrhage, which often occurs with trauma, is known to produce many life-threatening sequelae. Patients who survive the initial traumatic insult remain susceptible to sepsis, septic shock, multiple organ failure, and death (Baue 1998). Cellular dysfunction occurs in many organ systems, including the cardiovascular, liver, gut, and adrenal, after hemorrhagic shock, and remain depressed for a prolonged period of time (Wang 1990; Wang 1997; Wang 1998). Moreover, a marked depression in both specific and nonspecific cell-mediated immunity, which can explain the enhanced susceptibility to sepsis after such events, has been reported (Chaudry 1990).

Sex hormones are known to modulate immune function in animals and in humans under normal and various stress conditions (Homo-Delarche 1991). Studies have shown that female mice maintain their immune responses after trauma-hemorrhage, but male mice have markedly depressed responses (Wichmann 1996). Studies have demonstrated that male sex steroids can be responsible for producing the depression in cell and organ functions after trauma-hemorrhage and resuscitation (Wichmann 1996; Slimmer 1996). Additional support for this notion comes from studies that showed that castration of male animals 14 days before hemorrhagic shock prevented the depression in myocardial functions and immune responses observed under those conditions in non-castrated animals (Wichmann 1996; Remmers 1998). Furthermore, administration of flutamide, a testosterone receptor antagonist, improved the depressed immune responses and cardiac and hepatic functions in male animals after trauma and severe hemorrhage (Remmers 1997). Male and female sex steroids such as testosterone and estradiol play an opposite role in the development of cell and organ dysfunction after injury.

Estradiol is the predominant circulating sex hormone in females, and has been shown to have protective effects after adverse circulatory conditions such as organ ischemia and reperfusion (Dubai 1999; Fraser 1999). Moreover, the estrogen receptor is expressed in several organs in male animals such as the cardiovascular system and the liver (Echeverria 1994).

Materials and Methods

Experimental Procedures

The nonheparinized model of trauma-hemorrhage in the rat was used (Wang 1990). Male Sprague-Dawley rats (275-325 g, Charles River Labs, Wilmington, Mass.) were fasted overnight before the experiment but were allowed water ad libitum. The rats were anesthetized by methoxyflurane (Mallinckrodt Veterinary Inc., Mundelein, Ill.) inhalation prior to the induction of soft tissue trauma via 5-cm midline laparotomy. The abdomen was closed in layers, and catheters were placed in both femoral arteries and the right femoral vein (polyethylene [PE-50] tubing; Becton Dickinson & Co., Sparks, Md.). The wounds were bathed with 1% lidocaine (Elkins-Sinn Inc., Cherry Hill, N.J.) throughout the surgical procedure to reduce postoperative pain. Rats were then allowed to awaken, and bled to and maintained at a mean arterial pressure (MAP) of 40 mmHg. This level of hypotension was continued until the animals could not maintain MAP of 40 mmHg unless extra fluid, in the form of Ringer's lactate, was given. This time was defined as maximum bleed-out, and the amount of withdrawn blood was noted. Following this, the rats were maintained at MAP of 40 mmHg until 40% of the maximum bleed-out volume was returned in the form of Ringer's lactate. The animals were then resuscitated with four times the volume of the withdrawn blood over 60 minutes (about 45 mL/rat) with Ringer's lactate. The shed blood was not used for resuscitation. Fifteen minutes before the end of the resuscitation period, the rats received 50 mg/kg body weight 17 β-estradiol (β-estradiol 3-benzoate; Sigma, St. Louis, Mo.) subcutaneously or an equal volume of the vehicle (0.5 mL; corn oil, Sigma). The catheters were then removed, the vessels ligated, and the skin incisions closed with sutures. Sham-operated animals underwent the same groin dissection, which included the ligation of the femoral artery and vein, but neither hemorrhage nor resuscitation was carried out.

After returning the rats to their cages, they were allowed food and water ad libitum. At 24 hours after the completion of fluid resuscitation or sham-operation, the animals were anesthetized with methoxyflurane and catheterized via the right jugular vein. Under continued general anesthesia with pentobarbital sodium (25-30 mg/kg BW), cardiac output and hepatocellular function were measured in each animal.

Measurement of Cardiac Output

A 2.4-French fiberoptic catheter was placed into the right carotid artery and connected to an in vivo hemoreflectometer (Hospex Fiberoptics, Chestnut Hill, Mass.), as described previously (Wang 1990). Indocyanine green (ICG; Cardio Green, Becton Dickinson) solution was injected via the catheter in the jugular vein (1 mg/mL aqueous solution as a 50-mL bolus). Twenty ICG concentrations per second were recorded for approximately 30 seconds with the aid of a data acquisition program (Asystant1; Asyst Software, Rochester, N.Y.). The area under the ICG dilution curve was determined to calculate cardiac output (CO), which was then divided by the body weight to determine cardiac index.

Stroke volume (SV) was calculated as:

$$SV=(CO/HR) \times 1,000$$

Total peripheral resistance (TPR) was calculated as:

$$TPR=(CO/HR)$$

Measurement of Hepatocellular Function

Hepatocellular function was measured by the in vivo ICG clearance technique (Hauptmann 1991); ICG was administered by bolus injection (50 mL) of 1, 2, and 5 mg/mL ICG in aqueous solvent. The arterial concentration of ICG was recorded each second for 5 minutes. The initial velocity of ICG clearance for each dose was then calculated after performing a nonlinear regression of the ICG clearance curves according to an e-raised second order polynomial function (Wang 1990). The initial velocities of ICG clearance were then plotted against the ICG doses according to the methods of Lineweaver-Burk (Hauptmann 1998). This resulted in a straight line, allowing the determination of a maximum of ICG clearance (Vmax) and the Michaelis-Menten constant (Km). In this active hepatocellular membrane transport system, Vmax represents the functional hepatocyte ICG receptors and Km represents the efficiency of the active transport process.

Measurement of In Vivo Heart Performance

A polyethylene (PE-50) catheter was placed in the right carotid artery and carefully advanced into the left ventricle. The position of the catheter tip was confirmed by recording the characteristic left ventricular pressure curves. Data were analyzed using an in vivo heart performance analyzer (Micro-Med, Louisville, Ky.), as described in a previously (Robinson 1996). Various left ventricular performance parameters, such as maximal rate of the pressure increase (1 dP/dtmax) and decrease (2 dP/dtmax), were determined.

Measurement of Plasma Interleukin-6

Blood samples were drawn from the carotid catheter into a heparinized syringe at the end of each experiment. Plasma was separated by centrifugation at 12,000 g for 15 minutes at 4° C. and stored at 270° C. until assayed. Plasma interleukin (IL)-6 was measured using an enzyme-linked immunosorbent assay (ELISA) kit specific for rat IL-6 (Biosource, Camarillo, Calif.).

Statistical Analysis

Results are presented as ±mean standard error of the mean (SEM). There were eight animals in both sham groups, and seven or eight animals in the vehicle- or estradiol-treated hemorrhaged group, respectively. One-way analysis of variance (ANOVA), Tukey test, and Fisher exact test were used, and the differences were considered significant at P<0.05.

Results

Effects of Estradiol on Hemodynamic Parameters

Figure 12:
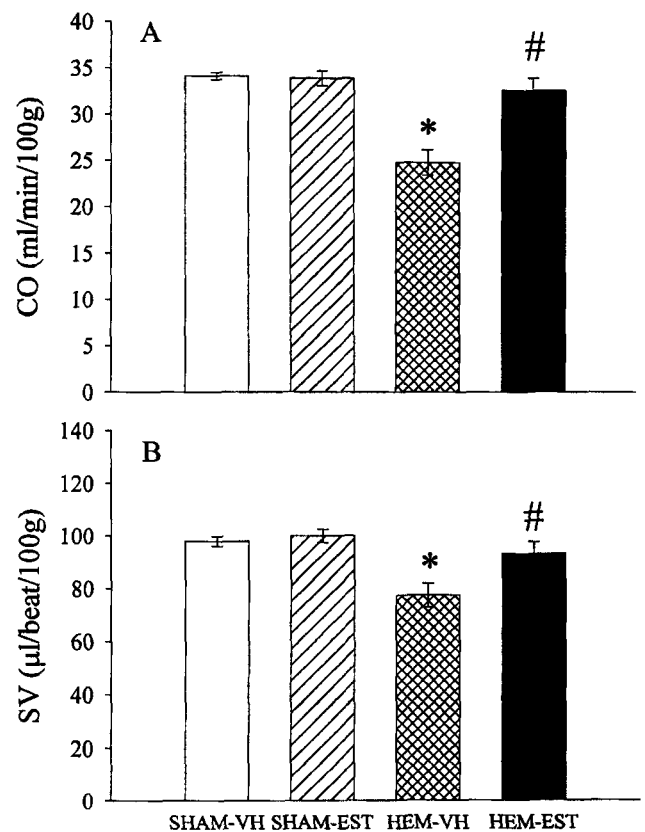
FIG. 12 shows the effects of estradiol administration on (A) cardiac output (CO) and (B) stroke volume (SV) at 24 hours after sham-operation or trauma-hemorrhage and resuscitation, showing the comparison of sham-operated rats treated with vehicle (SHAM-VH) or estradiol (SHAM-EST), as well as hemorrhaged animals treated with vehicle (HEM-VH) or estradiol (HEM-EST) (7 or 8 animals/group). Data presented as mean±SEM and compared by one-way ANOVA and Tukey test. $*P<0.05$ as compared to the respective shams; $\#P<0.05$ as compared to hemorrhaged and vehicle-treated animals.

The results in FIG. 12A indicate that cardiac index was 34.1±0.4 and 33.9±0.8 mL/min/100 g in sham-operated animals receiving vehicle or estradiol, respectively. Cardiac index decreased by 27.3% (P<0.05) in hemorrhaged and vehicle-treated animals at 24 hours after the completion of fluid resuscitation. Administration of estradiol after hemorrhage, however, restored the depressed cardiac index to sham levels. Similarly, SV decreased in hemorrhaged and vehicle-treated animals, whereas estradiol administration significantly improved SV as compared to vehicle-treated animals, and the values were similar to shams (FIG. 12B). Mean arterial pressure (MAP) decreased significantly at 24 hours after the completion of hemorrhage and resuscitation in both groups of hemorrhaged animals, in comparison to sham-operated animals (Table 2). However, animals treated with estradiol during resuscitation had a significantly higher MAP compared to vehicle-treated hemorrhaged rats. In contrast, heart rate did not differ significantly between the various groups. Total peripheral resistance was decreased in hemorrhaged animals in comparison to shams, irrespective of estradiol administration. Hematocrit decreased by more than half after trauma-hemorrhage and resuscitation in both hemorrhaged groups. Estradiol treatment in sham-operated animals had no effect on various hemodynamic parameters (FIG. 12, Table 2).

TABLE 2

Effects of 17β Estradiol on Hemodynamic Parameters at 24 Hours After the Completion of Trauma-Hemmorrhage and Resuscitation

|  | SHAM-VH | SHAM-EST | HEM-VH | HEM-EST |
|---|---|---|---|---|
| MAP (mmHg) | 105.5 ± 1.1 | 102.8 ± 3.1 | 70.2 ± 1.9* | 83.8 ± 2.1*† |
| HR (beats/min) | 347 ± 6 | 340 ± 4 | 327 ± 8 | 350 ± 7 |
| TPR (mmHg/mL/min/100 g) | 3.09 ± 0.04 | 3.03 ± 0.1 | 2.72 ± 0.09* | 2.67 ± 0.12* |
| Hct (%) | 44 ± 0.3 | 43 ± 0.3 | 19 ± 0.4* | 19 ± 0.5* |

Data presented as mean ± SEM and compared by one-way analysis of variance (ANOVA) and Tukey test. *P < .05 vs. the respective SHAM. †P < .05 vs. HEM-VH. MAP, mean arterial pressure; HR, heart rate; TPR, total peripheral resistance; Hct, hematocrit.

Effects of Estradiol on Heart Performance

Figure 13:
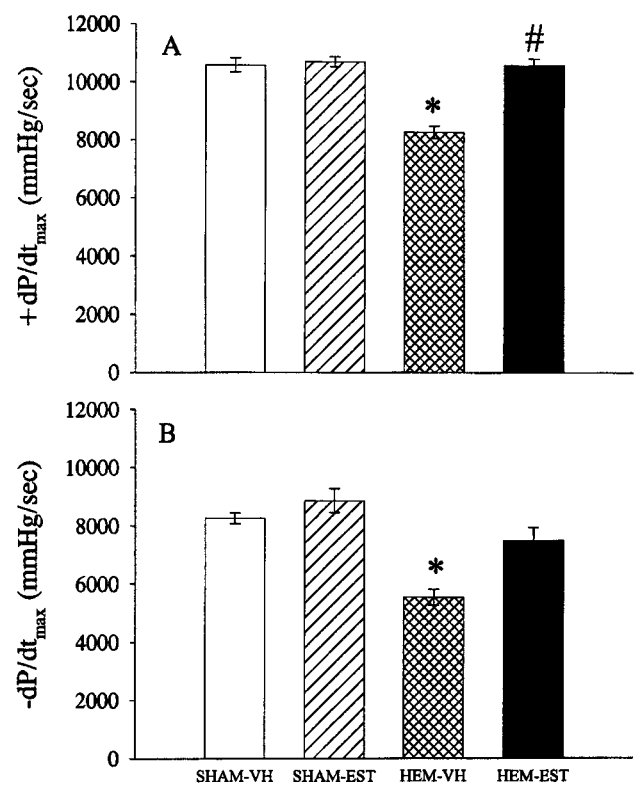
FIG. 13 shows the effects of estradiol administration on the maximal rate of pressure (A) increase (1 dP/dtmax) and (B) decrease (2 dP/dtmax) in the left ventricle at 24 hours after completion of fluid resuscitation. Data presented as mean±SEM and compared by one-way ANOVA and Tukey test. $*P<0.05$ as compared to the respective shams; $\#P<0.05$ as compared to hemorrhaged and vehicle-treated animals.

The maximal rate of left ventricle pressure increase (1 dP/dtmax) was significantly decreased after trauma-hemorrhage (FIG. 13A), but estradiol treatment increased 1 dP/dtmax after trauma-hemorrhage and resuscitation, showing no statistical difference from the sham-operated animals. The maximum rate of left ventricle pressure decrease (2 dP/dtmax) in the hemorrhaged group was also significantly decreased compared to the sham group, and 2 dP/dtmax in the estradiol-treated group increased significantly and was not different from sham values (FIG. 13B). Estradiol treatment in sham-operated animals affected neither 1 dP/dtmax nor 2 dP/dtmax.

Effects of Estradiol on Hepatocellular Function

Figure 14:
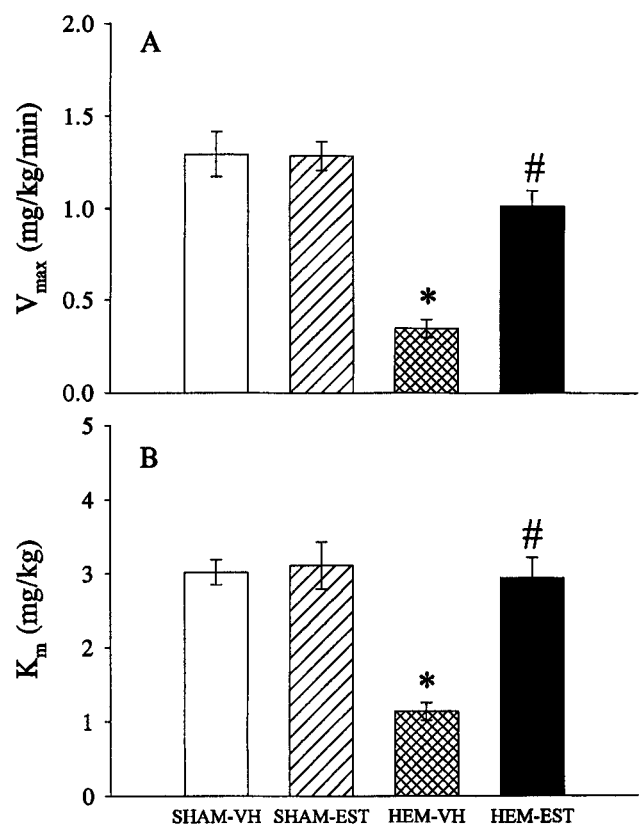
FIG. 14 shows the effects of estradiol administration on the active hepatocellular function at 24 hours after sham operation or trauma-hemorrhage and resuscitation as measured by indocyanine green (ICG) clearance technique. (A) Vmax represents the maximal velocity of ICG clearance and (B) Km represents the overall efficiency of the ICG transport. Data presented as mean±SEM and compared by one-way ANOVA and Tukey test. *P<0.05 as compared to the respective shams; #P<0.05 as compared to hemorrhaged and vehicle-treated animals.

The values of the maximal velocity of ICG clearance (Vmax) were 1.29±0.1 and 1.28±0.07 mg/kg/min in sham-operated animals receiving vehicle or estradiol, respectively (FIG. 14A). In hemorrhaged and vehicle-treated rats, Vmax decreased by 73% (P<0.05) at 24 hours after trauma- hemorrhage. In contrast, hemorrhaged and estradiol-treated animals had Vmax values similar to sham animals. As indicated in FIG. 14B, Km was 3.0±0.2 and 3.1±0.3 mg/kg in sham-operated animals receiving vehicle or estradiol, respectively, and it decreased by 62% (P<0.05) after trauma- hemorrhage and resuscitation in vehicle-treated rats. Estradiol administration significantly improved Km at 24 hours after the completion of resuscitation as compared to vehicle-treated animals, and the values were similar to shams (FIG. 14B). Estradiol administration in sham-operated animals had no effect on hepatocellular function.

Effects of Estradiol on Plasma Levels of IL-6

Figure 15:
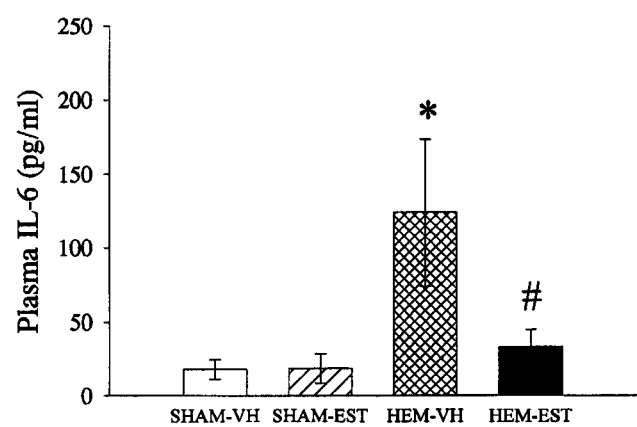
FIG. 15 shows alterations in plasma levels of interleukin (IL)-6 at 24 hours after sham operation or trauma-hemorrhage, measured by a specific ELISA. Data presented as mean±SEM and compared by one-way ANOVA and Tukey test. *P<0.05 as compared to the respective shams; #P<0.05 as compared to hemorrhaged and vehicle-treated animals.

Plasma levels of IL-6 increased by 691% (P<0.05) at 24 hours after resuscitation in hemorrhaged and vehicle-treated animals in comparison to the respective sham group (FIG. 15). In estradiol-treated animals, however, plasma levels of IL-6 did not differ significantly from the levels found in sham-operated rats at 24 after the completion of hemorrhage and resuscitation.

Effects of Trauma-Hemorrhage on Mortality

The mortality rate in the vehicle-treated hemorrhaged group was 30% (3 of 10 animals) and 11% (1 of 9) in the estradiol-treated group. However, due to the relatively small number of animals, this difference was not statistically significant (P=0.582).

Discussion

It has been shown that organ functions such as cardiac output, heart performance, adrenal responsiveness to exogenous corticotrophin, and hepatocellular clearance of ICG are significantly depressed in male animals after soft tissue trauma and severe hemorrhage (Robinson 1996; Wang 1990; Wang 1999).

The ovaries are the predominant source of estradiol production in females; the testes and peripheral aromatization of testosterone and androstenedione account for the low levels of estradiol in males. Significantly reduced cardiovascular morbidity and mortality has been reported in post-menopausal women receiving hormone replacement therapy (Stampfer 1991). Moreover, studies have indicated that 17β-estradiol is involved in various physiologic processes such as vascular response modulation.

The results of this study indicate that left entricular performance, as measured by 6 dP/dtmax, was significantly depressed after trauma-hemorrhage and resuscitation. 17β-estradiol-treated hemorrhaged animals displayed a restored 1 dP/dtmax, and an improved 2 dP/dtmax at 24 hours after the completion of fluid resuscitation. Moreover, the improved cardiac contractility was reflected by the restored cardiac index in treated rats. Because administration of estrogen after trauma-hemorrhage and resuscitation did not significantly alter heart rate, the improvement of the cardiac index under such conditions must be the result of an improvement in SV. Furthermore, hepatocellular function was also significantly improved, as evidenced by restoration of the Vmax and Km of ICG clearance after trauma-hemorrhage in estradiol-treated animals.

These improvements in organ functions also resulted in a better survival rate in estradiol-treated animals. The 24-hour mortality in this model of trauma and severe hemorrhagic shock was 30% in vehicle-treated animals, whereas it was 11% in the group receiving 17β-estradiol. Due to the small number of animals, however, this was not statistically significant. Moreover, it should be pointed out that we did not observe any adverse or beneficial effects of estradiol treatment in sham-operated animals.

Expression of the estrogen receptor has been reported in a number of cells and tissue in males (Diano 1999). Several studies have shown that the beneficial effects of estrogens on the cardiovascular system include both rapid non-genomic and long-term genomic mechanisms (Mendelsohn 1999; Chen 1999; Karas 1998).

The rapid effects of 17β-estradiol include endothelial nitric oxide (NO) production, presumably by increasing the expression or activity of the constitutive isoform of nitric oxide synthase (cNOS). The reduced release of endothelium-derived NO under various adverse circulation conditions is most likely due to the decreased activity of endothelial cNOS (Lefer 1994). In this regard, vascular endothelial cell function (i.e., the release of vascular endothelium-derived NO) is depressed early after the onset of hemorrhagic shock. Furthermore, it has been demonstrated that administration of L-arginine (the substrate for cNOS) restores the depressed cardiac output and organ blood flow after trauma-hemorrhage (Angele 1998). Thus, it is possible that the beneficial effects of estrogen on cardiovascular and hepatocellular functions after trauma-hemorrhage are due to the up-regulation of cNOS.

A single subcutaneous injection of 17β-estradiol-benzoate (50 mg/kg body weight) was used, and improved organ functions after trauma-hemorrhage were observed. Organ functions in the present study were measured at 24 hours after trauma- hemorrhage and resuscitation. Plasma levels of IL-6 were significantly elevated at 24 hours in vehicle-treated and hemorrhaged animals, whereas estradiol treatment during resuscitation down-regulated IL-6 to values that did not differ significantly from those in sham-operated animals. It has been shown that there is a significant correlation between IL-6 and Vmax of ICG clearance (Remmers 1998). Therefore, down-regulation of this inflam-matory cytokine may be responsible for restoring the de- pressed hepatocellular function under such conditions. The studies by Deshpande et al. (1999) have shown that estradiol attenuates cytokine production by inhibiting activation of the transcription factor NF-kB in murine macrophages. Kupffer cells (KC) appear to be the major source of inflammatory cytokine release after adverse circulatory conditions, (O'Neill 1994) because reduction of KC by administration of gadolinium chloride reduced IL-6 release after trauma-hemorrhage. Moreover, it has been shown that estradiol inhibits KC IL-6 release, whereas dihydrotestosterone enhances its production (Angele 1999). Therefore, KC IL-6 can release, and due to the close proximity of this cell population to hepatocytes, thereby improve hepatocellular function.

4. Example 4

17β-Estradiol Normalizes Immune Responses in Ovariectomized Females After Trauma-Hemorrhage It has been shown that immune responses in proestrus females are maintained after trauma-hemorrhage but markedly depressed in ovariectomized females under such conditions. Here, it is shown that decreased estrogen levels after ovariectomy are responsible for this immune depression. To test this, ovariectomized female CBA/J mice were subjected to laparotomy (i.e., soft tissue trauma) and hemorrhagic shock (35±5 mmHg for 90 min, then resuscitated) or sham operation. The mice received either 17β-estradiol (E2; 100 mg/25 g body wt) or vehicle subcutaneously during resuscitation. Immune cells were isolated 24 h thereafter. Splenocyte proliferation and interferon-γ, interleukin (IL)-2, and IL-3 release were significantly depressed after trauma-hemorrhage in vehicle-treated mice, whereas these functions were maintained in E2-treated mice. Peritoneal macrophage IL-1β and IL-6 release and splenic macrophage IL-6 and IL-12 release were also significantly depressed in vehicle-treated mice after trauma-hemorrhage, and release of these cytokines was restored by E2 treatment. In summary, it was found that the depressed splenic and peritoneal immune responses after trauma-hemorrhage can be normalized by a single dose of E2. Thus estrogen appears to be the causative factor in the maintenance of immunocompetence in females after trauma- hemorrhage, and its administration to ovariectomized or postmenopausal females is helpful in preventing immune depression under such conditions.

Materials and Methods

Animals. Inbred female CBA/J mice (Jackson Laboratories, Bar Harbor, Me.), 8-9 wk old (24-26 g body wt), were used.

Experimental groups. Ovariectomy was performed in female CBA/J mice 2 wk before trauma-hemorrhage using two dorsolateral incisions. In preliminary studies it was found that, during this period, plasma concentrations of E2 and uterine wet weight as a sensitive parameter of systemic estrogen exposure significantly decreased in ovariectomized females compared with females in the proestrus state. Two weeks after ovariectomy, the animals were divided into four groups. Groups 1 and 2 consisted of sham-operated ovariectomized females, which were neither hemorrhaged nor resuscitated. Animals in groups 3 and 4 consisted of ovariectomized females, which were subjected to the trauma-hemorrhage procedure. Immediately before initiation of fluid resuscitation, animals in groups 1 and 3 received a subcutaneous injection of vehicle (200 ml corn oil), and animals in groups 2 and 4 were treated with E2 (100 mg/25 g body wt dissolved in 200 ml corn oil). Each group consisted of 7-8 animals.

Trauma-hemorrhage procedure. Mice in the trauma-hemorrhage groups were lightly anesthetized with methoxyflurane (Metofane; Pitman Moore, Mundelein, Ill.) and restrained in a supine position, and a 2.5-cm midline laparotomy (i.e., soft tissue trauma induced) was performed, which was then closed aseptically in two layers using 6-0 Ethilon sutures (Ethicon, Somerville, N.J.). Both femoral arteries were then aseptically cannulated with polyethylene-10 tubing (Clay-Adams, Parsippany, N.J.) using a minimal dissection technique, and the animals were allowed to awaken. Blood pressure was constantly monitored by attaching one of the catheters to a blood pressure analyzer (Micro-Med, Louisville, Ky.). Lidocaine was applied to the incision sites to provide analgesia during the study period. Upon awakening, the animals were bled through the other catheter to a mean arterial blood pressure of 35±5 mmHg (mean arterial blood pressure prehemorrhage was 95±5 mmHg), which was maintained for 90 min. At the end of that procedure, the animals were resuscitated with four times the shed blood volume in the form of lactated Ringer solution. The catheters were then removed, the vessels were ligated, and the groin incisions were closed. Sham-operated animals underwent the same surgical procedure, which included ligation of both femoral arteries, but neither hemorrhage nor fluid resuscitation was carried out. There was no mortality observed in this model of trauma-hemorrhage.

Blood, tissue, and cell harvesting procedure. The animals were killed by methoxyflurane overdose at 24 h after trauma-hemorrhage and resuscitation to obtain the spleen, pMf, uteri, and whole blood. Plasma collection and storage. Whole blood was obtained by cardiac puncture and placed in microcentrifuge tubes (Microtainer; Becton Dickinson, Rutherford, N.J.). The tubes were then centrifuged at 16,000 g for 15 min at 4° C. Plasma was separated, placed in pyrogen-free microcentrifuge tubes, immediately frozen, and stored (280° C.) until assayed.

Cell line maintenance. The interleukin (IL)-2-dependent CTLL-2 cells were obtained from American Type Culture Collection and maintained according to their directions. The IL-3-dependent FDC-P1 cells were maintained as previously described (Ihle 1992). The IL-6-sensitive murine B cell hybridoma (7TD1) was maintained as previously described (Ihle 1992).

Preparation of splenocyte culture. At 24 h after sham operation or trauma-hemorrhage and resuscitation, the spleens were removed aseptically and placed in separate petri dishes containing 4° C. phosphate-buffered saline (PBS) solution. Splenocytes were isolated as previously described in detail (Zellweger 1995). Briefly, the organs were gently ground between frosted microscope slides to produce a single cell suspension. This suspension was centrifuged at 300 g for 15 min. After resuspension, the erythrocytes were lysed hypotonically, and the remaining cells were washed with PBS by centrifugation (300 g, 15 min). Viability was tested using trypan blue exclusion and found to be ~95% regardless of the group assessed. The splenocytes were then resuspended in RPMI 1640 (GIBCO-BRL, Grand Island, N.Y.) containing 10% heat-inactivated fetal bovine serum (FBS; GIBCO-BRL) to yield a final concentration of $1 \times 10^7$ cells/ml. The ability of the splenocyte cultures to produce cytokines in response to a mitogenic challenge was assessed by incubation for 48 h (at 37° C., 5% $CO_2$, and 90% humidity) in the presence of 2.5 mg/ml concanavalin A (Con A; Pharmacia/LKB Biotech, Piscataway, N.J.). After incubation, the cell suspension was centrifuged at 300 g for 15 min, and the supernatants were harvested and stored at 280° C. until assayed for interferon-g (IFN-γ), IL-2, IL-3, and IL-10.

Splenocyte proliferation. A second portion of the splenocyte suspension was placed into a 96-well microtiter plate (Corning Glass, Corning, N.Y.) in aliquots of 100 ml. The cells' ability to proliferate in response to mitogenic stimulation with 0 (negative control) or 2.5 mg/ml Con A was measured by [$^3$H]thymidine incorporation technique as previously described (Stephan 1987). Briefly, after incubation for 48 h at 37° C., 5% $CO_2$, and 90% humidity, 1 mCi of the radionucleotide (sp act 6.7 Ci/mmol; NEN, Wilmington, Del.) was added to each well, and the cultures were incubated for another 16 h. The cells were then harvested onto glass fiber filter mats, and the beta decay was detected by liquid scintillation counting, as previously described (Meldrum 1991).

Preparation of sMΦ and pMΦ culture. Spleens were harvested aseptically, and sMΦ cultures were established as previously described in detail (Zellweger 1996). Resident pMΦ were harvested by peritoneal lavage at 24 h after sham operation or trauma-hemorrhage and resuscitation, and monolayers were established as previously described (Ayala 1990). The monolayers of sMΦ and pMΦ ($1 \times 10^6$ cells/ml) were stimulated with 10 mg of lipopolysaccharide W/ml Click's medium containing 10% heat-inactivated FBS for 48 h at 37° C., 5% $CO_2$, and 90% humidity to assess the cells' ability to release cytokines. (Lipopolysaccharide W was from *Escherichia coli* 055:B5, Difco Laboratories, Detroit, Mich.) At the end of the incubation period, the culture supernatants were removed, centrifuged at 300 g for 15 min, divided into aliquots, and stored.

Assessment of cytokine release. The capacity of the mixed splenocyte culture to produce IL-2 or IL-3 was assessed by determining the amount of IL-2 or IL-3 in the collected culture supernatant. Serial dilutions of the supernatants and standards were added to CTLL-2 cells ($1 \times 10^5$ cells/ml) or to FDC-P1 cells ($2.5 \times 10^5$ cells/ml) and incubated for 24 h (FDC-P1) or 48 h (CTLL-2) at 37° C., 5% $CO_2$, and 90% humidity. At the end of this period, 1 mCi of [$^3$H]thymidine (sp act 6.7 Ci/mmol, NEN) was added to each well, and the cultures were incubated for an additional 16 h. The cells were then harvested onto glass-fiber mats, and the beta decay was detected by liquid scintillation radiography (Meldrum 1991).

IL-10 concentrations in macrophage and splenocyte supernatants and IFN-γ levels in the splenocyte supernatants were determined using sandwich-enzyme-linked immunosorbent assay technique (ELISA) according to the manufacturer's recommendations (BD OptEIA ELISA set; BD Pharmingen, San Diego, Calif.).

IL-6 activity was determined by assessing the 72-h proliferation of the IL-6-dependent murine B cell hybridoma 7TD1 stimulated by serial dilutions of sMΦ and pMΦ supernatants (Ayala 1992). For the last 3 h of incubation, 20 ml of a 3-(4,5-dimethylthiazol-2-yl)-2,5-diphenyltetrazolium bromide solution (5 mg/ml in RPMI 1640; Sigma Chemical, St. Louis, Mo.) was added to each well. The amount of dark blue formazan crystal formation was then measured spectro-photometrically. The units of IL-6 activity were determined by comparison of curves produced from dilutions of a recombinant mouse IL-6 standard (200 U/ml; Genzyme, Cambridge, Mass.) according to the methods of Mizel (Mizel 1981). IL-1β levels in pMΦ supernatants were determined by ELISA according to the manufacturer's recommendations (Genzyme). Determination of plasma E2 concentration. E2 concentration was determined using a commercially available radio-immunoassay (ICN Biomedicals, Costa Mesa, Calif.) as described by the manufacturer.

Statistical analysis. The results are presented as means±SE. One-way ANOVA followed by the Student-Newman-Keuls test as a post hoc test for multiple comparisons was used to determine the significance of the differences between experimental means. A P value <0.05 was considered significant.

Results

Figure 16:
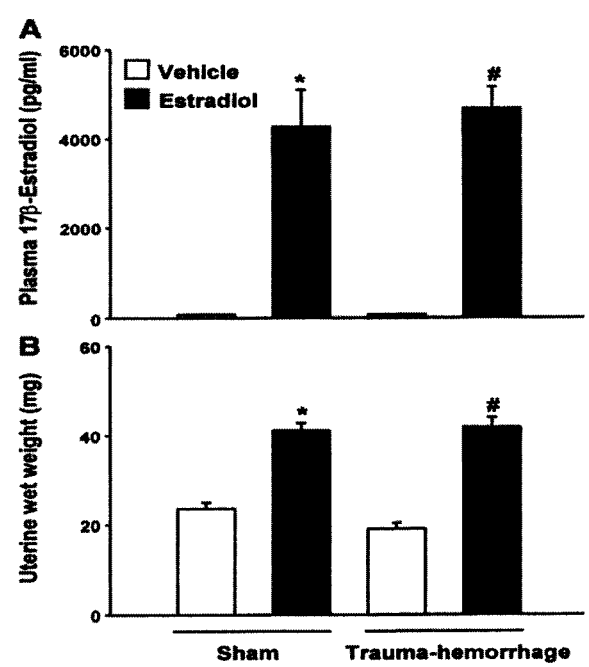
FIG. 16 shows 17β-estradiol concentrations (A) and uterine wet weight (B) of female CBA/J mice that were subjected to trauma-hemorrhage and resuscitation or to sham operation at 2 wk after ovariectomy. At the end of trauma-hemorrhage or sham operation, the ovariectomized females were either treated with corn oil vehicle or 100 mg 17β-estradiol/25 g body wt. Plasma 17β-estradiol concentrations were measured by radioimmunoassay. Values are means±SE of 7-8 animals in each group. ANOVA: *p<0.05 vs. sham vehicle, #p<0.05 vs. trauma-hemorrhage vehicle.

Biological effect of E2 treatment. At 24 h after vehicle administration, plasma concentrations of E2 were 16.6±5.3 pg/ml in ovariectomized females that were sham operated and 15.7±8.3 pg/ml in females that underwent trauma-hemorrhage. Administration of E2 in ovariectomized females resulted in significantly increased plasma concentrations of E2 in sham-operated as well as hemorrhaged animals (p<0.05; FIG. 16A) compared with corresponding vehicle-treated ovariectomized females. In addition, uterine wet weight, a sensitive parameter of systemic estrogen exposure, significantly increased in E2-treated ovariectomized females that were sham operated or hemorrhaged (p<0.05 vs. corresponding vehicle-treated ovariectomized females; FIG. 16B).

Figure 17:
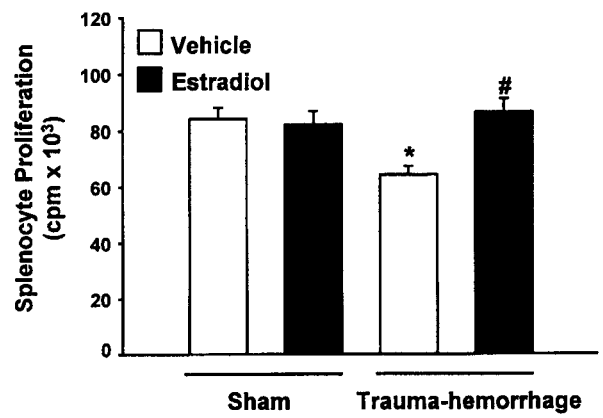
FIG. 17 shows proliferative capacity of splenocytes harvested from ovariectomized female CBA/J mice at 24 h after sham operation or trauma-hemorrhage and treatment with corn oil vehicle or 100 μg 17β-estradiol/25 g body wt. All female mice were ovariectomized 2 wk before the experiment. Splenocytes were stimulated with 2.5 mg/ml concanavalin A for 48 h, and proliferation was measured by [3H]thymidine incorporation technique. Values are means±SE of 7-8 animals in each group. ANOVA: *p<0.05 vs. sham vehicle, #p<0.05 vs. trauma-hemorrhage vehicle.

Splenocyte proliferation. At 24 h after trauma-hemorrhage, splenocyte proliferative capacity was significantly depressed in ovariectomized females that received vehicle at the beginning of resuscitation compared with sham-operated females receiving vehicle (p<0.05; FIG. 17). In ovariectomized females treated with E2 after trauma-hemorrhage, however, no depression of splenocyte proliferative capacity was observed.

Figure 18:
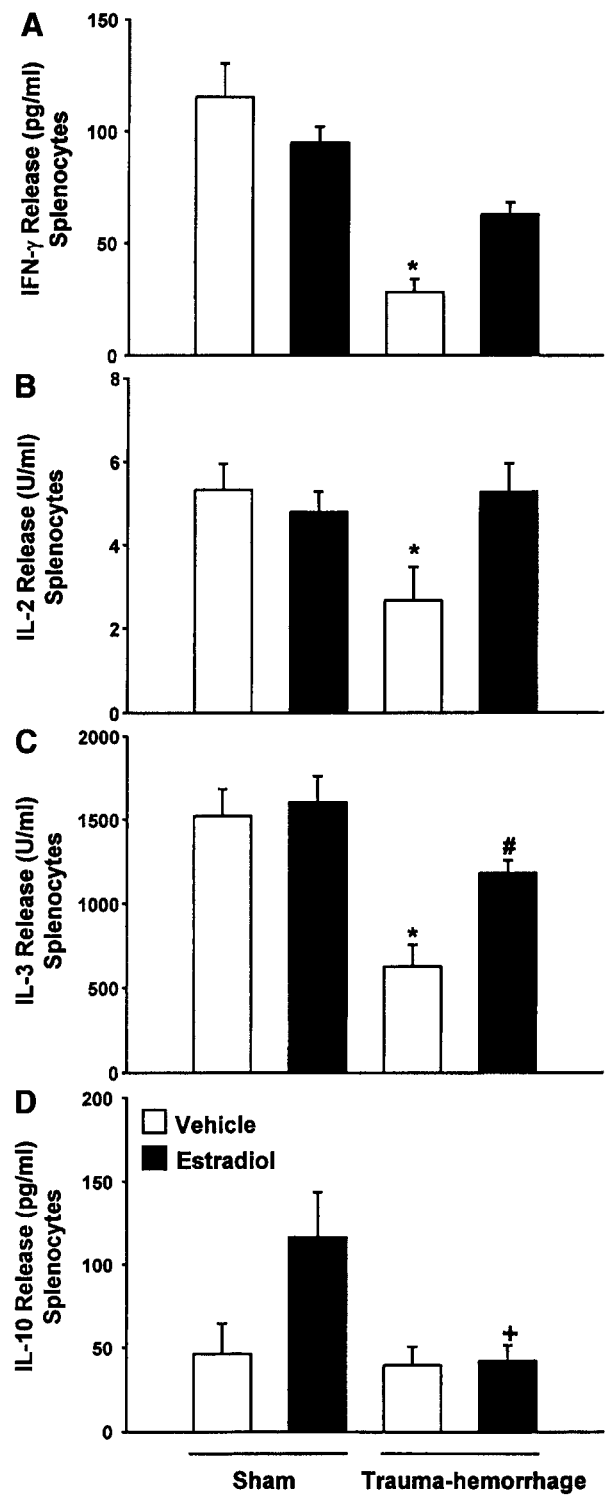
FIG. 18 shows interferon-±(IFN-γ; A), interleukin-2 (IL-2; B), IL-3 (C), and IL-10 (D) release of splenocytes harvested from ovariectomized female CBA/J mice at 24 h after sham operation or trauma-hemorrhage and treatment with corn oil vehicle or 100 μg 17β-estradiol/25 g body wt. All female mice were ovariectomized 2 wk before the experiment. Splenocytes were stimulated with 2.5 mg/ml concanavalin A for 48 h. IL-2 levels in splenocyte supernatants were measured using a bioassay specific for IL-2 (CTLL-2), IL-3 levels were determined by a specific bioassay for IL-3 (FDC-P1), and IFN-γ and IL-10 concentrations were measured by sandwich-enzyme-linked immunosorbent assay technique. Values are means±SE of 7-8 animals in each group. ANOVA: *p<0.05 vs. sham vehicle; #p<0.05 vs. trauma-hemorrhage vehicle, p<0.05 vs. sham estradiol.

Splenocyte cytokine production. After trauma-hemorrhage, splenocyte release was significantly depressed in vehicle-treated ovariectomized females compared with sham-operated animals (p<0.05; FIG. 3A). In contrast, no depression of IFN-γ production was observed in splenocytes harvested from ovariectomized females treated with E2 after trauma-hemorrhage. Trauma-hemorrhage resulted in a significantly depressed production of IL-2 by splenocytes harvested from vehicle-treated ovariectomized females (p<0.05; FIG. 3B). Treatment with E2 restored IL-2 productive capacity. IL-3 production was significantly suppressed after trauma-hemorrhage in splenocytes harvested from vehicle-treated ovariectomized females (p<0.05; FIG. 18C); however, treatment of ovariectomized females with E2 at the beginning of resuscitation significantly improved splenocyte IL-3 release capacity after trauma-hemorrhage toward sham levels (p<0.05; FIG. 18C). In contrast to the production of IFN-γ, IL-2, and IL-3, the release of IL-10 was maintained after trauma-hemorrhage in ovariectomized females receiving vehicle (FIG. 16D). However, treatment with E2 led to significantly reduced IL-10 production after trauma-hemorrhage compared with E2-treated sham-operated animals (p<0.05, FIG. 16D).

Figure 19:
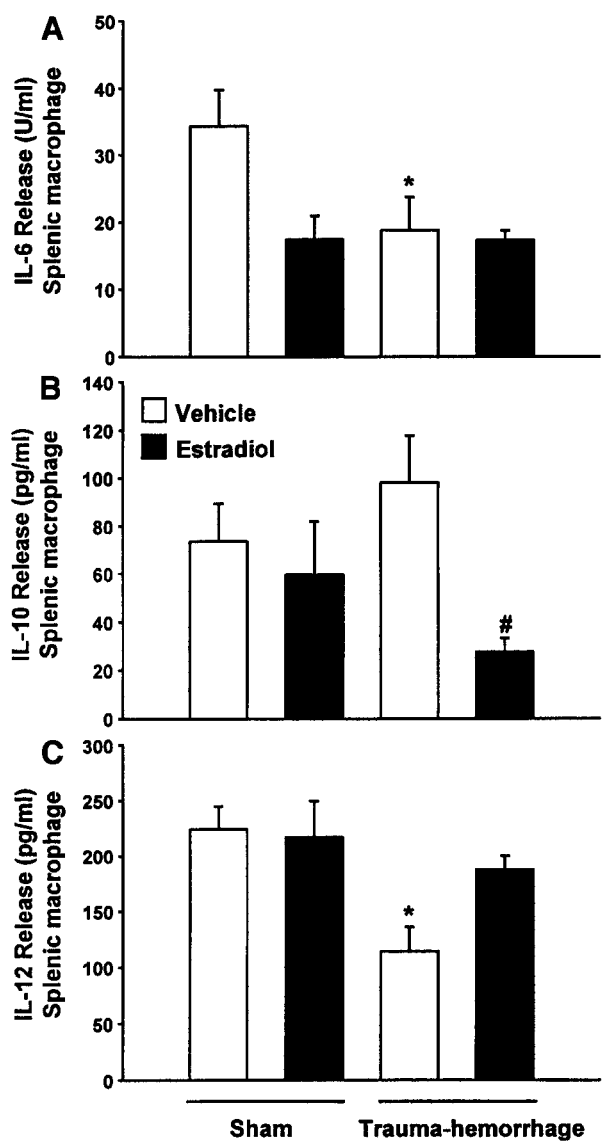
FIG. 19 shows the release of IL-6 (A), IL-10 (B), and IL-12 (C) by splenic macrophages (sMΦ) harvested from ovariectomized female CBA/J mice at 24 h after sham operation or trauma-hemorrhage and treatment with corn oil vehicle or 100 μg 17β-estradiol/25 g body wt. All female mice were ovariectomized 2 wk before the experiment. sMΦ were cultured in the presence of 10 mg/ml lipopolysaccharide W for 48 h. IL-6 levels in macrophage supernatants were measured using a specific bioassay (7TD1); IL-10 and IL-12 concentrations were determined by sandwich-enzyme-linked immunosorbent assay technique. Values are means±SE of 7-8 animals in each group. ANOVA: *p<0.05 vs. sham vehicle, #p<0.05 vs. trauma-hemorrhage vehicle.
Figure 20:
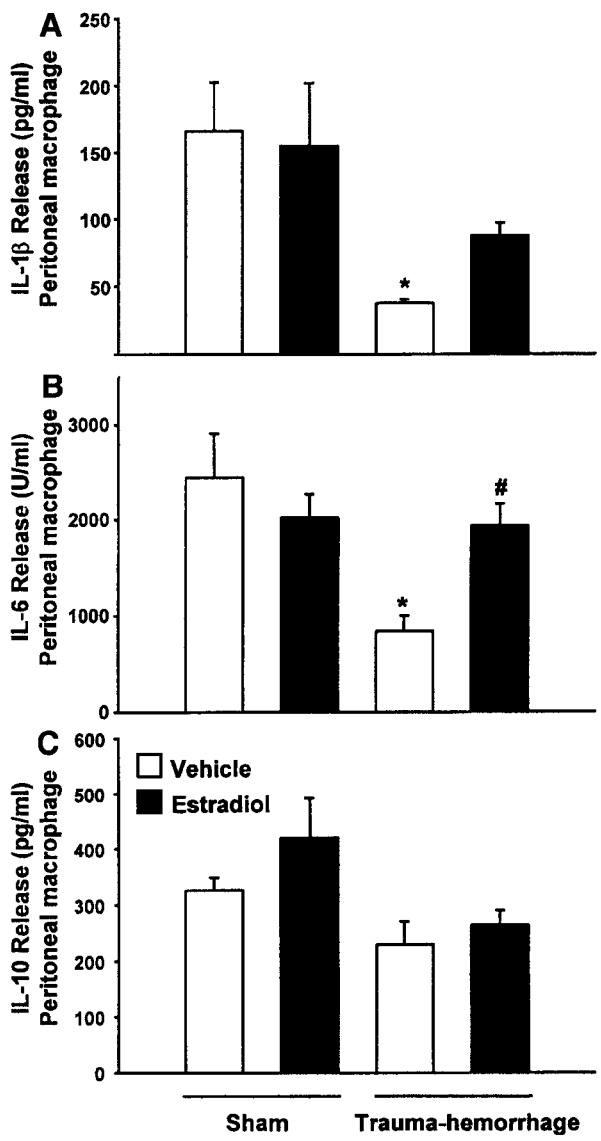
FIG. 20 shows the release of IL-1β (A), IL-6 (B), and IL-10 (C) by peritoneal macrophages (pMΦ) harvested from ovariectomized female CBA/J mice at 24 h after sham operation or trauma-hemorrhage and treat-ment with corn oil vehicle or 100 μg 17β-estradiol/25 g body wt. All female mice were ovariectomized 2 wk before the experiment. pMΦ were cultured in the presence of 10 mg/ml lipopolysaccharide W for 48 h. IL-6 levels in macrophage supernatants were measured by specific bioassay (7TD1); IL-1β and IL-10 were measured by sandwich-enzyme-linked immunosorbent assay technique. Values are means±SE of 7-8 animals in each group. ANOVA: *p<0.05 vs. sham vehicle, #p<0.05 vs. trauma-hemorrhage vehicle.

Macrophage cytokine production. sMΦ IL-6 release was significantly depressed in vehicle-treated ovariectomized females after trauma-hemorrhage (p<0.05; FIG. 19A). Administration of E2 in ovariectomized females during resuscitation did not influence IL-6 release under these conditions. IL-10 production by sMΦ was not affected by trauma-hemorrhage in vehicle-treated mice; however, E2 treatment of such animals significantly reduced IL-10 release (p<0.05; FIG. 19B). sMΦ IL-12 production was significantly depressed after trauma-hemorrhage in vehicle-treated ovariectomized females compared with their corresponding sham-op-erated animals p<0.05; FIG. 19C). Treatment with E2 prevented the depression in sMΦ IL-12 production after trauma-hemorrhage. At 24 h after trauma-hemorrhage, pMΦ IL-10 release was significantly depressed in ovariectomized females receiving vehicle compared with vehicle-treated sham-operated animals (p<0.05; FIG. 20A). Treatment with E2 led to a partial restoration of pMΦ IL-1j release. Similar to sMΦ pMΦ. IL-6 production was significantly depressed in ovariectomized females that underwent trauma-hemorrhage and received vehicle (p<0.05, FIG. 5B). In contrast to sMΦ, IL-6 production by pMΦ was maintained at sham levels in mice that were treated with E2 at the beginning of resuscitation. pMΦ IL-10 production was not affected by either trauma-hemorrhage or E2 treatment (FIG. 20C).

Discussion

The aim of the present study was to determine whether administration of E2 in ovariectomized females has any effect on splenocyte, sMΦ, or pMΦ immune functions after trauma-hemorrhage. The results presented here indicate that at 24 h after sham operation or trauma-hemorrhage and administration of 100 mg E2/25 g body wt, plasma concentrations of E2 were significantly increased compared with vehicle-treated ovariectomized females. Furthermore, uterine wet weight, a sensitive parameter of systemic estrogen exposure, significantly increased in ovariectomized females that received E2 compared with vehicle-treated ovariectomized females. In all experiments discussed here, ovariectomized females were used at 2 wk after ovariectomy. This time point was selected because it was shown that during this period, plasma concentrations of E2 and uterine wet weight significantly decreased in ovariectomized females com- pared with females in the proestrus state of the estrus cycle. Thus the findings that E2 administration significantly increased plasma levels of this hormone as well as uterine wet weight in ovariectomized females indicate the biological effectiveness of the hormone treatment used. Here, ovariectomized females were used at 2 wk after ovariectomy. This time point was selected because preliminary studies have shown that during this period, plasma concentrations of E2 and uterine wet weight significantly decreased in ovariectomized females compared with females in the proestrus state of the estrus cycle. Thus the findings that E2 administration significantly increased plasma levels of this hormone as well as uterine wet weight in ovariectomized females indicate the biological effectiveness of the hormone treatment used.

Administration of E2 in ovariectomized females after trauma-hemorrhage led to profound changes in immune functions compared with ovariectomized females receiving vehicle. Comparable with the findings from previous studies (Knöferl 1999), the results indicate that in ovariectomized females, sMΦ and pMΦ proinflammatory cytokine production (IL-1β, IL-6, and IL-12) was significantly depressed after trauma-hemorrhage. However, administration of a single dose of E2 in ovariectomized females at the beginning of fluid resuscitation resulted in partial normalization of sMΦ and pMΦ proinflammatory cytokine release capacity under those conditions. In this regard, it has previously been shown that normal females in the proestrus state of the estrus cycle also maintain sMΦ and pMΦ function after trauma-hemorrhage (Knöferl 1999). Thus the findings that ovariectomy leads to a depression of sMΦ and pMΦ proinflammatory cytokine release after trauma-hemorrhage indicate that physiological levels of female sex steroids and, in particular, E2 are involved in maintaining macrophage proinflammatory cytokine release in the splenic and peritoneal compartment. Furthermore, the present finding that administration of E2 in ovariectomized females partially restored sMΦ and pMΦ proinflammatory cytokine release shows that this female sex steroid plays a critical role in regulating macrophage functions. In this regard, it should be noted that the pattern of immune depression observed in ovariectomized females after trauma-hemorrhage is comparable to the depression of immune functions seen in male mice after trauma-hemorrhage (Zellweger 1995). Thus the observation that high concentrations of testosterone as well as low levels of estradiol are associated with immunosuppression after trauma-hemorrhage could lead to the hypothesis that the ratio of male to female sex hormones is essential to the course of the immune response to a traumatic insult.

Comparable to the depression observed in sMΦ and pMΦ function, trauma-hemorrhage resulted in a significantly depressed splenocyte proliferative capacity and splenocyte cytokine production in ovariectomized females receiving vehicle. Administration of E2 at the end of trauma-hemorrhage, however, restored splenocyte proliferation to values comparable with sham-operated animals. Furthermore, E2 treatment normalized the depressed production of IFN-γ, IL-2, and IL-3 in ovariectomized females that underwent trauma- hemorrhage. IL-3 is a growth factor that influences growth of specific T lymphocyte subsets as well as proliferation of early T cell precursors (Mossalayi 1990; Schneider 1988). With regard to this finding, the suppression in splenocyte proliferation correlated with suppressed IL-3 production after trauma-hemorrhage, and the restoration of IL-3 production by E2 paralleled restored splenocyte proliferative responses. Previous studies have shown that suppressed IL-3 production correlates with lower immune functional capacity in aged mice (Hobbs 1993; Kahlke 2000). These findings suggest that E2 is involved in the reg ulation of splenocyte immune responses and that the decreased levels of E2 in ovariectomized females contribute to the depression of splenocyte immune functions after trauma-hemorrhage. Support for the idea that E2 has stimulatory effects on posthemorrhage splenocyte function comes from studies that have shown that administration of E2 in males restored splenocyte immune responses after trauma-hemor-rhage (Knöferl 2000). Previous findings do not allow for the distinction as to whether the stimulatory effects of E2 on splenocyte immune functions are due to the direct actions of this hormone on splenocytes or are also being mediated via indirect mechanisms, such as macrophage/splenocyte interactions. In this regard, these results indicate that administration of E2 restored sMΦ IL-12 production in ovari ectomized females that underwent trauma-hemorrhage. Because macrophages are present in splenocyte cultures, it is possible that macrophage-derived IL-12, a well-characterized stimulant of splenocyte immune functions (Trinchieri 1993), contributes to the beneficial effects of E2 treatment. Whether indirect mechanisms other than sMΦ IL-12 production are involved in restoring splenocyte immune functions in E2-treated ovariectomized females remains to be determined. An explanation for why E2 normalized many immune parameters in ovariectomized mice after trauma-hemorrhage is suppressed apoptosis. E2 has been shown to suppress apoptosis (Evans 1997; Gohel 1999) due to upregulation of Bcl-2, an antiapoptotic protein (Bynoe 2000). Additionally, decreased estrogen levels in ovariectomized females can also result in increased apoptosis.

In contrast to the depression of sMΦ proinflammatory cytokine release and splenocyte cytokine production observed in vehicle-treated ovariectomized females after trauma-hemorrhage, anti-inflammatory cytokine, i.e., IL-10, production by sMΦ and splenocytes was maintained under those conditions. The maintained production of IL-10 by sMΦ and splenocytes after trauma-hemorrhage was associated with a significantly depressed T lymphocyte proliferative capacity. It can be speculated that normal IL-10 production may play a role in the regulation of the inflammatory response by limiting T lymphocyte proliferation and the proinflammatory response. In ovariectomized females treated with E2, however, IL-10 production decreased after trauma-hemorrhage compared with sham-operated animals, and this was associated with maintained proinflammatory cytokine production. The anti-inflammatory cytokine IL-10 has previously been described as an important immunosuppressant of cell-mediated immunity (Howard 1992) and has been implicated in the suppression of splenocyte immune functions after hemorrhage (Ayala 1994). Therefore, E2 decreases anti-inflammatory cytokine production by sMΦ and splenocytes after trauma-hemorrhage and that the maintained production of IL-10 observed in ovariectomized females receiving vehicle can contribute to the depression of immune functions under those conditions.

5. Example 5

17β-Estradiol (E2) Administration After Major Blood Loss Improves Liver, ATP, 3-Hour Survival and Also Long Term Survival Following Prolonged Hypotension (3 Hour) and Fluid Resuscitation Although E2 administration after trauma-hemorrhage (T-H) and fluid resuscitation produces salutary effects on organ functions, it was not known if E2 has any beneficial effects after major blood loss in the absence of fluid resuscitation. Male SD rats ~250 g) underwent T-H (tissue trauma, BP 40 mmHg in 10 min and maintained at that BP by further blood withdrawal until maximum bleed out (MBO, 60% of total blood volume) occurred (45:t5 min)). E2 i.v. (1 mg/Kg, 0.4 ml/Kg volume, i.e., 120 μL/300 g body weight) or vehicle (cyclodextrin, CD) was then infused. No additional fluid was given for 3 hours. If rats survived, they received Ringer's lactate, 4× the MBO volume. A custom-fabricated 31p coil was placed on the surface of the rat's liver after laparotomy in another group, and spectra acquired using 4.7T NMR spectroscopy via a 31p coil in real time before and during hemorrhagic shock. Shock increased phosphomonoester and Pi with a concomitant decrease in B-ATP in both groups. The f3-ATP:Pi ratio was at a life-sustaining level in the E2 group as compared to the CD group. Since E2 infusion after major blood loss maintains higher liver ATP levels during severe hypotension, markedly improves 3-hour survival rates without fluid resuscitation and increases long-term survival after resuscitation, E2 is a novel hormone for preserving essential cellular energy status under conditions in which fluid resuscitation is not possible for a period of 3 hours following severe blood loss.

6. Example 6

Effect of 17β-Estradiol on Signal Transduction Pathways and Secondary Damage in Experimental Spinal Cord Trauma Since studies have shown that 17β-estradiol produces anti-inflammatory effects following various adverse circulatory conditions, it was examined whether administration of 17β-estradiol prior to spinal cord injury (SCI) has any salutary effects in reducing SCI.

SCI was induced by the application of vascular clips (force of 24 g) to the dura via a four-level T5-T8 laminectomy. In order to gain a better insight into the mechanism of action of the anti-inflammatory effects of 17β-estradiol, the following endpoints of the inflammatory process were evaluated: (1) spinal cord inflammation and tissue injury (histological score); (2) neutrophil infiltration (myeloperoxidase activity); (3) expression of iNOS, nitrotyrosine and COX-2; (4) apoptosis (TUNEL staining and Bax and Bcl-2 expression); (5) tissue TNFα, IL-6, IL-1β and MCP-1 levels. In another set of experiments, the pre or post treatment with 17β-estradiol significantly ameliorates the recovery of limb function (evaluated by motor recovery score).

In order to elucidate whether the protective effects of 17β-estradiol were mediated via the estrogen receptors, the effect of an estrogen receptor antagonist, ICI 182,780, on the protective effects of 17β-estradiol was investigated ICI 182,780 (500 μg/kg administered subcutaneously 1 hour prior to treatment with 17β-estradiol) significantly antagonized the effect of the 17β-estradiol and abolished the protective effect against SCI. Taken together, the results clearly demonstrate that administration of 17β-estradiol prior to SCI reduces the development of inflammation and tissue injury associated with spinal cord trauma.

(1) Introduction

Spinal cord injury (SCI) is a highly debilitating pathology (Maegele 2005). Although innovative medical care has improved patient outcome, advances in pharmacotherapy for the purpose of limiting neuronal injury and promoting regeneration have been limited. The complex pathophysiology of SCI can explain the difficulty in finding a suitable therapy. The primary traumatic mechanical injury to the spinal cord causes the death of a number of neurons that cannot be recovered and regenerated. Studies indicate that neurons continue to die for hours following traumatic SCI (Balentine 1985). The events that characterize this successive phase to mechanical injury are called "secondary damage." The secondary damage is determined by a large number of cellular, molecular, and biochemical cascades. The presence of a local inflammatory response has been demonstrated, which amplifies the secondary damage (Blight 1992). The cardinal features of inflammation, namely infiltration of inflammatory cells (polymorphonuclear neutrophils PMN, macrophage, and lymphocytes), release of inflammatory mediators, and activation of endothelial cells leading to increased vascular permeability, edema formation, and tissue destruction have been extensively characterized in animal models of SCI (Popovich 1996). Because SCI involves a complex pathophysiology, an effective therapy employs either multiple agents or a multi-active agent. It has been shown that treatment with the steroid hormone 17β-estradiol (estrogen) can attenuate several of the damaging pathways initiated after SCI (Szabo 1998). 17β-estradiol, the most abundant form of estrogen in the body, has been shown to be neuroprotective and produces therapeutic effects in various models of central nervous system (CNS) disease where inflammation and immune-mediated processes predominate (Sribnick 2003; Matejuk 2004; Palaszynski 2004; Sribnick 2005). 17β-estradiol exerts its neuroprotective effects, in part, by acting as an anti-inflammatory agent and also an anti-oxidant (Vegeto 2004).

In order to characterize the effect of 17β-estradiol in a model of SCI, the following endpoints of the inflammatory response were determined: (1) histological damage; (2) motor recovery; (3) neutrophil infiltration; (4) pro-inflammatory cytokines; (5) nitrotyrosine, iNOS and COX-2 expression; (6) apoptosis (TUNEL staining); (7) Bax and Bcl-2 expression. In addition, the effects of the systemic administration of estrogen receptor antagonist (ICI 182,780) on the above parameters of inflammation were investigated.

(2) Material and Methods (a) Animals

Adult male CD1 mice (25-30 g, Harlan Nossan, Milan, Italy) were housed in a controlled environment and provided with standard rodent chow and water. Animal care was in compliance with Italian regulations on protection of animals used for experimental and other scientific purpose (D.M. 116192), as well as with the EEC regulations (O.J. of E.C. L 358/1 12/18/1986).

(b) SCI

Mice were anaesthetized using chloral hydrate (400 mg/kg body weight) (Genovese 2006). A longitudinal incision was made on the midline of the back, exposing the paravertebral muscles. These muscles were dissected away exposing T5-T8 vertebrae. The spinal cord was exposed via a four-level T6-T7 laminectomy and SCI was produced by extradural compression using an aneurysm clip with a closing force of 24 g. Following surgery, 1 ml of saline was administered subcutaneously in order to replace the blood volume lost during surgery. During the surgery and recovery from anesthesia, the mice were placed on a warm heating pad and covered with a warm towel. The mice were singly housed in a temperature-controlled room at 27° C. and survival was measured over a period of 10 days. Food and water were provided to the mice ad libitum. During this time period, the animals' bladders were manually voided twice a day until the mice were able to regain normal bladder function. In all injured groups, the spinal cord was compressed for 1 min. Sham-injured animals were only subjected to laminectomy.

(c) Experimental Groups

Figure 30:
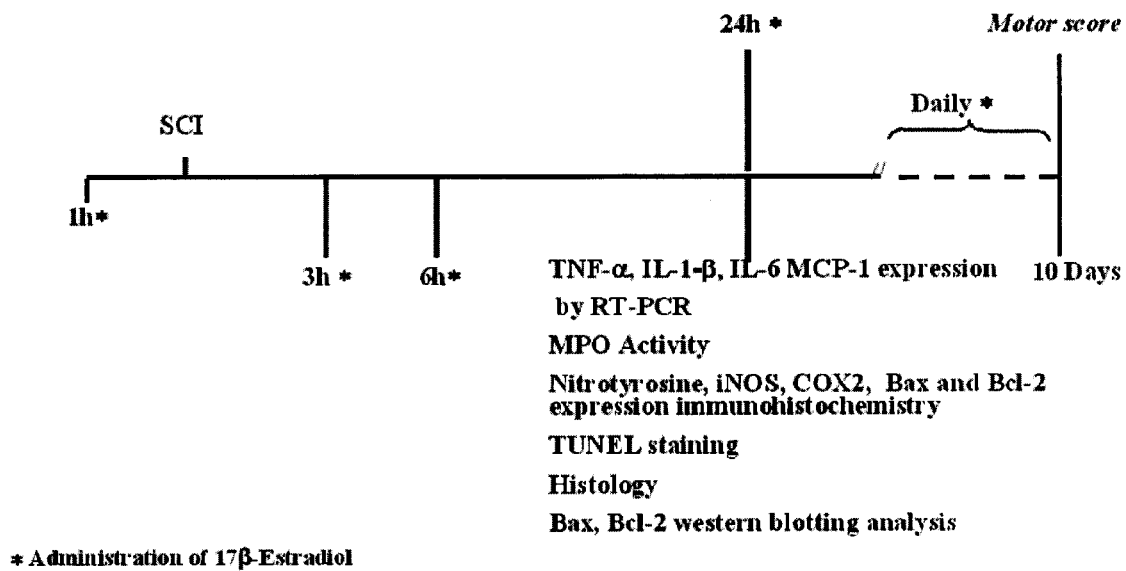
FIG. 30 shows mice were sacrificed at different time points in order to evaluate the various parameters (n=10 mice from each group for each time point). 17β-estradiol was administered subcutaneously at a dose of 300 μg/kg 1 h before SCI and 3 h and 6 h after SCI; ICI 182,780 (500 μg/kg subcutaneously) was administered 1 hour before the administration of 17β-estradiol.

Mice were randomly allocated into the following groups: (i) saline+SCI group, mice received saline subcutaneously and were subjected to SCI (n=40); (ii) 17β-estradiol group, same as the saline+SCI group but 17β-estradiol was administered subcutaneously at a dose of 300 µg/kg 1 h before SCI and 3 h and 6 h after SCI (n=40); (iii) ICI group, same as the 17β-estradiol group but they received ICI 182,780 at the dose of 500 µg/kg subcutaneously 1 hour before the administration of 17β-estradiol (iv) (n=40); (v) saline+sham group, mice were subjected to the surgical procedures as above group except that the aneurysm clip was not applied (n=40); (vi) sham+17β-estradiol group, identical to sham+saline group but they received an administration of 17β-estradiol; (vii) sham+ICI group, identical to sham+17β-estradiol group except that they received an administration of ICI 182,780 (n=40). In the experiments regarding the motor score, the animals from all the experimental groups were observed and treated daily for 9 days after SCI. At different time points (see FIG. 30), the mice (n=10 from each group for each of the 3 time points) were sacrificed in order to evaluate the various parameters as described below.

In a separate set of experiments, in order to elucidate the potential clinical significance of the protective effects of 17β-estradiol, it was also investigated whether the post-treatment with 17β-estradiol, administered subcutaneously at a dose of 300 µg/kg at 3 and 6 h after SCI attenuates the motor dysfunction assessed by motor score. The dose and the time of treatment of ICI 182,780 (500 µg/kg) was based on in vivo studies (Cuzzocrea 2000), as well as the dose of 17β-estradiol (Yune 2004).

(d) Total Protein Extraction and Western Blot Analysis for Bax and Bcl-2

Spinal cord tissue, obtained from animals killed 24 h after injury or sham-injured, was disrupted by homogenization with an Ultra-turrax T8 homogenizer on ice in lysis buffer (20 mM HEPES pH 7.9, 1.5 mM $MgCl_2$, 400 mM NaCl, 1 mM ethylenediaminetetraacetic acid [EDTA], 1 mM ethyleneglycoltetraacetic acid [EGTA], 1 mM dithiothreitol [DTT], 0.5 mM phenylmethylsulphonyl fluoride [PMSF], 1.5 µg/ml trypsin inhibitor, 3 µg/ml pepstatin, 2 µg/ml leupeptin, 40 µM benzidamin, 1% NP-40, 20% glycerol). After 1 hour, tissue lysates were obtained by centrifugation at 100,000×g for 15 min at 4° C. Protein concentrations were estimated by the Bio-Rad protein assay (Bio-Rad Laboratories, Segrate, Milan, Italy) using BSA as standard.

For Western blot analysis, 70 µg protein of lysates were mixed with gel loading buffer (50 mM Tris, 10% (w/v), sodium dodecyl sulphate (SDS), 10% (w/v) glycerol, 10% (v/v) 2- mercaptoethanol, 2 mg/ml bromophenol), boiled for 5 min, and subjected to SDSPAGE (12% polyacrylamide). The blot was performed by transferring proteins from a slab gel to nitrocellulose membrane at 240mA for 40 min at room temperature. The filter was then blocked with 1×PBS, 5% nonfat dried milk for 40 min at room temperature and probed with specific monoclonal antibodies against Bax (Santa Cruz Biotechnology, Inc., Santa Cruz, Calif.; 1:1,000), or Bcl-2 (Santa Cruz Biotechnology, Inc., Santa Cruz, Calif.; 1:1,000) in 1×PBS, 5% nonfat dried milk, 0.1% Tween 20 at 4° C., overnight. The AffiniPure Goat Anti-Rabbit IgG coupled to peroxidase secondary antibody (1:2000; Jackson Immuno Research, Laboratories, Inc., CA, USA) was incubated for 1 hour at room temperature. Subsequently, the blot was extensively washed with PBS, developed using SuperSignal West Pico chemiluminescence Substrate (PIERCE, Milan, Italy), according to the manufacturer's instructions, and exposed to Kodak X-Omat film (Eastman Kodak Co., Rochester, N.Y.). α-Tubulin protein (Sigma; 1:1000) Western blot was performed to ensure equal sample loading. The protein bands of Bax (23~kDa), or Bcl -2 (26~kDa) on x-ray film were scanned and densitometrically analyzed with a model GS-700 imaging densitometer (Bio-Rad Laboratories).

To ascertain that blots were loaded with equal amounts of protein lysates, they were also incubated in the presence of the antibody against α-tubulin protein (1:10,000 Sigma-Aldrich Corp.). The densitometric data for Western are normalized for loading control values.

(e) Light Microscopy

Spinal cord biopsies were taken at 24 hours following trauma. Tissue segments containing the lesion (1 cm on each side of the lesion) were paraffin embedded and cut into 5-µm-thick sections. Tissue sections were deparaffinized with xylene, stained with Haematoxylin/Eosin (H&E) and Luxol Fast Blue staining (used to assess demyelination) and studied using light microscopy (Dialux 22 Leitz).

The segments of each spinal cord were evaluated by an experienced histopathologist (RO). Damaged neurons were counted and the histopathologic changes of the gray matter were scored on a 6-point scale (Sirin 2000): 0, no lesion observed, 1, gray matter contained 1 to 5 eosinophilic neurons; 2, gray matter contained 5 to 10 eosinophilic neurons; 3, gray matter contained more than 10 eosinophilic neurons; 4, small infarction (less than one third of the gray matter area); 5, moderate infarction; (one third to one half of the gray matter area); 6, large infarction (more than half of the gray matter area). The scores from all the sections from each spinal cord were averaged to give a final score for an individual mice. All the histological studies were performed in a blinded fashion.

(f) Grading of Motor Disturbance

The motor function of mice subjected to compression trauma was assessed once a day for 10 days after injury. Recovery from motor disturbance was graded using the modified murine Basso, Beattie, and Bresnahan (BBB) (Basso 1995) hind limb locomotor rating scale (Joshi 2002a; Joshi 2002b). The following criteria were considered: 0=No hind limb movement; 1=Slight (<50% range of motion) movement of 1-2 joints; 2=Extensive (>50% range of motion) movement of 1 joint and slight movement of one other joint; 3=Extensive movement of 2 joints; 4=Slight movement in all 3 joints; 5=Slight movement of 2 joints and extensive movement of 1 joint; 6=Extensive movement of 2 joints and slight movement of 1 joint; 7=Extensive movement of all 3 joints; 8=Sweeping without weight support or plantar placement and no weight support; 9=Plantar placement with weight support in stance only or dorsal stepping with weight support; 10=Occasional (0-50% of the time) weight-supported plantar steps and no coordination (Front/hind limb coordination); 11=Frequent (50-94% of the time) to consistent (95-100% of the time) weight-supported plantar steps and no coordination; 12=Frequent to consistent weight-supported plantar steps and occasional coordination; 13=Frequent to consistent weight-supported plantar steps and frequent coordination; 14=Consistent weight-supported plantar steps, consistent coordination and predominant paw position is rotated during locomotion (lift off and contact) or frequent plantar stepping, consistent coordination and occasional dorsal stepping; 15=Consistent plantar stepping and coordination, no/occasional toe clearance, paw position is parallel at initial contact; 16=Consistent plantar stepping and coordination (Front/hind limb coordination) and frequent toe clearance and predominant paw position is parallel at initial contact and rotated at lift off; 17=Consistent plantar stepping and coordination and frequent toe clearance and predominant paw position is parallel at initial contact and lift off; 18=Consistent plantar stepping and coordination and consistent toe clearance and predominant paw position is parallel at initial contact and rotated at lift off; 19=Consistent plantar stepping and coordination and consistent toe clearance and predominant paw position is parallel at initial contact and lift off; 20=Consistent plantar stepping, coordinated gait, consistent toe clearance, predominant paw position is parallel at initial contact and lift off and trunk instability; 21=Consistent plantar stepping, coordinated gait, consistent toe clearance, predominant paw position is parallel at initial contact and lift off and trunk stability.

(g) Immunohistochemical Localization of Nitrotyrosine, iNOS, MPO, COX-2, Bax and Bcl-2

At 24 h after SCI, the tissues were fixed in 10% (w/v) PBS-buffered formaldehyde and 8-µm sections were prepared from paraffin embedded tissues. After deparaffinization, endogenous peroxidase was quenched with 0.3% (v/v) hydrogen peroxide in 60% (v/v) methanol for 30 min. The sections were permeabilized with 0.1% (w/v) Triton X-100 in PBS for 20 min. Non-specific adsorption was minimized by incubating the section in 2% (v/v) normal goat serum in PBS for 20 min. Endogenous biotin or avidin binding sites were blocked by sequential incubation for 15 min with biotin and avidin (DBA), respectively. Sections were incubated overnight with antinitrotyrosine rabbit polyclonal antibody (Upstate; 1:500 in PBS, v/v), with anti-iNOS polyclonal antibody rat (1:500 in PBS, v/v), anti-COX-2 monoclonal antibody (1:500 in PBS, v/v), anti-Bax rabbit polyclonal antibody (Santa Cruz Biotechnology, Inc., Santa Cruz, Calif.; 1:500 in PBS, v/v), or with anti-Bcl-2 polyclonal antibody rat (Santa Cruz Biotechnology, Inc., Santa Cruz, Calif.; 1:500 in PBS, v/v), or with anti-MPO polyclonal antibody (Santa Cruz Biotechnology, Inc., Santa Cruz, Calif.; 1:500 in PBS, v/v). Sections were washed with PBS, and incubated with secondary antibody. Specific labeling was detected with a biotin-conjugated goat anti-rabbit IgG and avidin-biotin peroxidase complex (DBA) and counterstained whith nuclear fast red. To verify the binding specificity for nitrotyrosine, iNOS, COX-2, Bax, and Bcl-2, some sections were also incubated with only the primary antibody (no secondary) or with only the secondary antibody (no primary). In these situations no positive staining was found in the sections indicating that the immunoreaction was positive in all the experiments carried out. Immunocytochemistry photographs (n=5) were assessed by densitometry as previously described (Shea 1994) by using Imaging Densitometer (AxioVision, Zeiss, Milan, Italy) and a computer program.

(h) Terminal Deoxynucleotidyltransferase-Mediated UTP end Labeling (TUNEL) Assay TUNEL assay was conducted by using a TUNEL detection kit according to the manufacturer's instructions (Apotag, HRP kit DBA, Milano, Italy). Briefly, sections were incubated with 15 µg/ml proteinase K for 15 minutes at room temperature and then washed with PBS. Endogenous peroxidase was inactivated by 3% hydrogen peroxide for 5 minutes at room temperature and then washed with PBS. Sections were immersed in terminal deoxynucleotidyltransferase (TdT) buffer containing deoxynucleotidyl transferase and biotinylated dUTP in TdT buffer, incubated in a humid atmosphere at 37° C. for 90 minutes, and then washed with PBS. The sections were incubated at room temperature for 30 minutes with anti-horseradish peroxidase-conjugated antibody, and the signals were visualized with diaminobenzidine. The number of TUNEL positive cells/high-power field was counted in 5 to 10 fields for each coded slide as previously described (Yamanishi 2002).

(i) Myeloperoxidase Activity

Myeloperoxidase (MPO) activity, an indicator of PMN accumulation, was determined as previously described (Mullane 1985) 24 h after SCI. At the specified time following SCI, spinal cord tissues were obtained and weighed and each piece homogenized in a solution containing 0.5% (w/v) hexadecyl-trimethyl-ammonium bromide dissolved in 10 mM potassium phosphate buffer (pH 7) and centrifuged for 30 minutes at 20,000×g at 4° C. An aliquot of the supernatant was then allowed to react with a solution of 1.6 mM tetramethylbenzidine and 0.1 mM hydrogen peroxide. The rate of change in absorbance was measured spectrophotometrically at 650 nm. MPO activity was defined as the quantity of enzyme degrading 1 µmol of peroxide per minute at 37° C. and was expressed in milliunits/g of wet tissue.

(j) Quantitative Real Time PCR

A segment of spinal cord (320±124 mg) encompassing lesion epicentre was homogenized in a solution of Tri-reagent (Sigma®, Germany) according to the manufacturer's instructions. Total cellular RNA was isolated from the aqueous phase then the levels of IL-α, TNF-α, MCP-1, IL-6 gene products were determined by Real Time PCR. The amount of each PCR product of gene target was normalized to Glyceraldehyde-3-phosphate dehydrogenase (GAPDH). The RNA extracted from spinal cord of individual mice was reverse trascripted into first strand cDNA with Random Hexamers and purified Avian Myeloblastosis Virus Reverse Transcriptase (Takara, Japan) in 20 ml of reaction after a DNAse treatment and stored at −80° C. until use. Primers pair for each cytokine was designed using the software Oligo (Molecular Biology Insights, Cascade, Colo., USA). The PCR reactions were performed using the following cycle conditions: a denaturation step for 15 minutes at 95° C. and 40 cycles of 30 seconds denaturation at 94° C., 30 seconds annealing (TNF-á 61° C., IL-6 54° C., IL-1β 61° C., MCP-1 54° C., GADPH 56° C.), 15 sec at 72° C. and 7 minutes of final extension at 72° C. The PCR products were visualized by electrophoresis on agarose gel 2% stained by ethidium bromide. The purified PCR products were cloned into a plasmid vector, transformed into the $E.$ $coli$ TOP 10 (Invitrogen) and purified with Turbo Kit (QBIOgene, Calif., USA). The recombinant plasmid was linearized upstream the target sequence using the restriction endonuclease PmeI (Fermentas, Canada). Tenfold dilutions of recombinant plasmid from $10^9$ copies down to $10^1$ copies were used as standards. The real time PCR assay was developed and evaluated on the Rotor-Gene 3000 system (Corbett Research, Australia). Reaction was carried out in a final volume of 25 µl containing 1× of SYBR PREMIX Ex Taq Takara, 200 nM each forward and reverse primers, 1× of Rox References Dye and 2 µl of cDNA. Cycling parameters were the following: 10 minutes at 95° C. for polymerase activation followed by 40 cycles of 15 seconds at 95° C., 15 seconds annealing (TNF-α 61° C., IL-10 54° C., IL-6 54° C., IL-1β 61° C., MCP-1 54° C. GADPH 56° C.) 20 sec at 72° C. The signal was acquired on the FAM channel (multichannel machine) (source, 470 nm; detector, 510 nm; gain set to 5) with the fluorescence reading taken at the end of each 72° C. step. A melt step was added after a cycling run performed with the same parameters of the SYBR Green assay. During the melt cycle the temperature was increased by increments of 1° C. from 72° C. to 95° C. and the signal was acquired on the FAM channel (source, 470 nm; detector, 510 nm; gain set to 5).

b) Materials

Unless otherwise stated, all compounds were obtained from Sigma-Aldrich Company Ltd. (Milan, Italy). All stock solutions were prepared in non-pyrogenic saline (0.9% NaCl; Baxter, Milan, Italy), 10% DMSO, or 10% ethanol.

(a) Statistical Evaluation

All values in the figures and text are expressed as mean±standard error of the mean (SEM) of the number (n) of observations. For the in vivo studies, n represents the number of animals studied. In the experiments involving histology or immunohistochemistry, the figures shown are representative of at least three experiments performed on different experimental days. The results were analyzed by one-way ANOVA followed by a Bonferroni post-hoc test for multiple comparisons. A p value of less than 0.05 was considered significant. BBB scale data were analyzed by the Mann-Whitney test and considered significant when p value was less than 0.05.

c) Results (a) 17β-estradiol Reduces the Severity of SCI

Figures 31A, 31B, 31C, 31D, 31E:
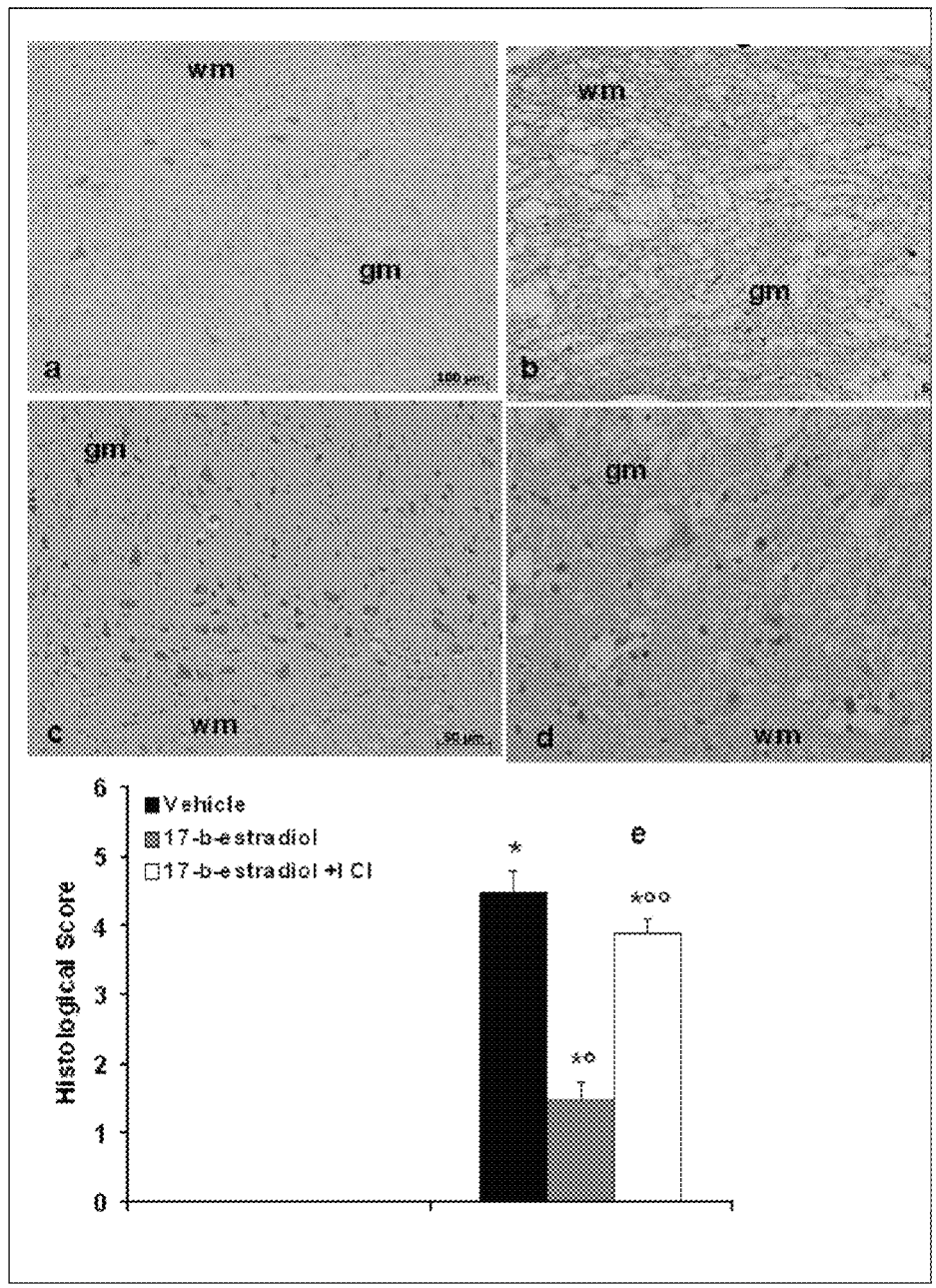
FIG. 31 shows the effect of 17β-estradiol on histological alterations of the spinal cord tissue 24 hours after injury. No histological alteration was observed in the spinal cord from sham-operated mice (a). 24 hours after trauma significant damage to the spinal cord in non-treated SCI-operated mice at the perilesional area was assessed by the presence of edema as well as alteration of the white matter (b). Notably, significant protection from the SCI was observed in the tissue collected from 17β-estradiol SCI-treated mice (c). Myelin structure was observed by Luxol fast blue staining. At 24 hours after the injury in non-treated SCI-operated, mice, a significant loss of myelin was observed. In contrast in 17β-estradiol SCI-treated mice myelin degradation was attenuated. Co-administration of ICI 182,780 and 17β-estradiol significantly blocked the effect of the 17β-estradiol on histological alteration (d) as well as on myelin structure. The histological score (e) was made by an independent observer. This figure is representative of at least 3 experiments performed on different experimental days. *p<0.01 versus SHAM, °P<0.01 versus SCI, p<0.01 vs. 17β-estradiol. wm: White matter; gm: gray matter.

The severity of the trauma at the level of the perilesional area, assessed as the presence of edema as well as alteration of the white matter (FIG. 31B, see histological score 31E), was evaluated at 24 hours after injury by Haematoxylin/Eosin. A significant damage to the spinal cord was observed in the spinal cord tissue of control mice subjected to SCI when compared with sham-operated mice (FIG. 31A see histological score 31E). Notably, a significant protection against the SCI-induced histological alteration was observed in 17β-estradiol-treated mice (FIG. 31C see histological score 31E). Myelin structure was observed by Luxol fast blue staining (FIG. 31F-H see histological score 31E). In sham animals myelin structure was clearly stained by Luxol fast blue in both lateral and dorsal funiculi of the spinal cord. At 24 hours after the injury, a significant loss of myelin in lateral and dorsal funiculi was observed in control mice subjected to SCI. (FIG. 31F see histological score 31E). In contrast, in 17β-estradiol-treated mice myelin degradation was attenuated in the central part of lateral and dorsal funiculi (FIG. 31G see histological score 31E). Co-administration of ICI 182,780 and 17β-estradiol significantly blocked the effect of the 17β-estradiol on the histological alteration (FIG. 31D see histological score 31E) as well as on the myelin structure (FIG. 31H see histological score 31E).

(b) Effects of 17β-estradiol on Neutrophil Infiltration

Figure 33:
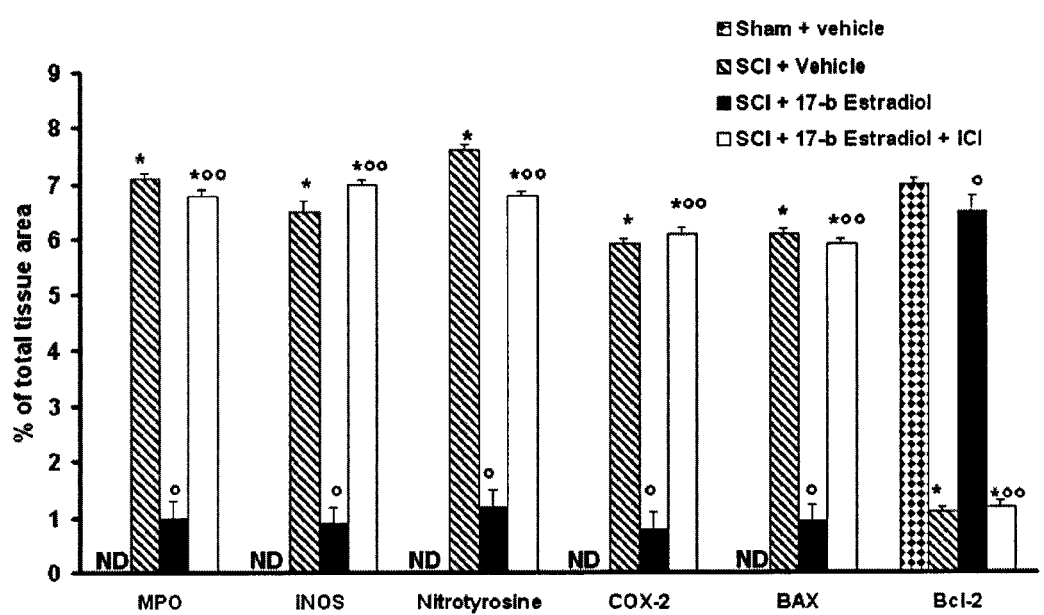
FIG. 33 shows typical densitometry evaluation. Densitometry analysis of immunocytochemistry photographs (n=5 photos from each sample collected from all mice in each experimental group) for MPO, iNOS, nitrotyrosine, COX-2, Bax and Bcl-2 from spinal cord tissues was assessed. The assay was carried out by using Optilab Graftek software on a Macintosh personal computer (CPU G3-266). Data are expressed as % of total tissue area. *P<0.01 vs. Sham; °P<0.01 vs. SCI. ND: not detectable.

The above mentioned histological pattern of SCI appeared to be correlated with the influx of leukocytes into the spinal cord. We therefore investigated the role of 17-β-estradiol on the neutrophil infiltration by measuring tissue MPO activity. MPO activity was significantly elevated in the spinal cord at 24 hours after injury in control mice subjected to SCI when compared with sham-operated mice (FIG. 32A). In 17β-estradiol-treated mice, the MPO activity in the spinal cord at 24 hours after injury was significantly attenuated in comparison to that observed in SCI control mice (FIG. 32A). Co-administration of ICI 182,780 and 17β-estradiol significantly blocked the effect of the 17β-estradiol on the neutrophils infiltration (FIG. 32A). In addition, tissue sections obtained at 24 hours from SCI-operated mice demonstrate positive staining for MPO mainly localized in the infiltrated inflammatory cells in injured area (FIG. 32C1 see densitometry analysis FIG. 33). In mice treated with the 17β-estradiol (FIG. 32D, see densitometry analysis FIG. 33), the staining for MPO was visibly and significantly reduced in comparison with the SCI-operated mice. There was no staining for MPO in spinal cord tissues obtained from the sham group of mice (FIG. 32B, see densitometry analysis FIG. 33). Co-administration of ICI 182,780 and 17β-estradiol significantly blocked the effect of the 17β-estradiol on the MPO (FIG. 32E1 see densitometry analysis FIG. 33).

(c) 17β-estradiol Modulates Expression of Cytokines and Chemokines

Figures 34A, 34B, 34C, 34D:
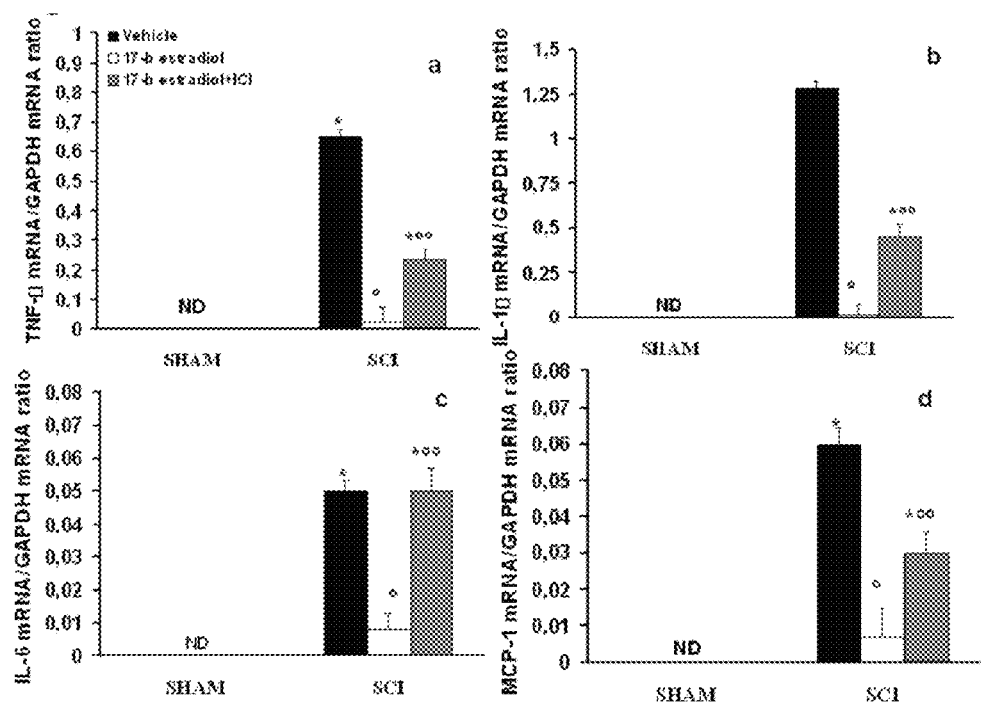
FIG. 34 shows the effects of 17β-estradiol on spinal cord levels of TNF-α IL1β, IL-6 and MCP-1. A significant increase of the TNF-α (a), IL-1β (b), IL-6 (c) and MCP-1 (d) mRNA levels was observed in the spinal cord tissues at 24 h after SCI. In the spinal cord tissues of 17β-estradioltreated SCI mice the TNF-α (a), IL-1β (b), IL-6 (c) and MCP-1 (d) mRNA levels were significantly reduced in comparison to those of SCI animals measured in the same conditions. Co-administration of ICI 182,780 and 17β-estradiol significantly blocked the effect of the 17β-estradiol on TNF-α, IL1β, IL-6 and MCP-1. The results of the quantitative real time PCR of the TNF-α, IL1β, IL-6 and MCP-1 mRNA expression are expressed a ratio between the number of copies of the target cytokine and the number of copies of the housekeeper (GAPDH) to have an absolute ratio. *p<0.05 vs. vehicle. °p<0.01 vs. SCI. °°p<0.01 vs. 17β-estradiol.

To determine whether 17β-estradiol may modulate the inflammatory process through the regulation of the secretion of several cytokines, the tissue levels of TNF-β, IL-6, and MCP-1 were analyzed. When compared with sham-operated mice, SCI caused a significant increase in the tissue levels of TNF-α, IL-1β, IL-6, MCP-1 in SCI control mice (FIG. 34). The increases in the tissue levels of TNF-α, IL-1β0, IL-6, MCP-1 seen in 17β-estradiol-treated mice subjected to SCI were significantly reduced in comparison with the vehicle-treated mice (FIG. 34). Co-administration of ICI 182,780 and 17β-estradiol significantly but parti4).

Figure 35A:
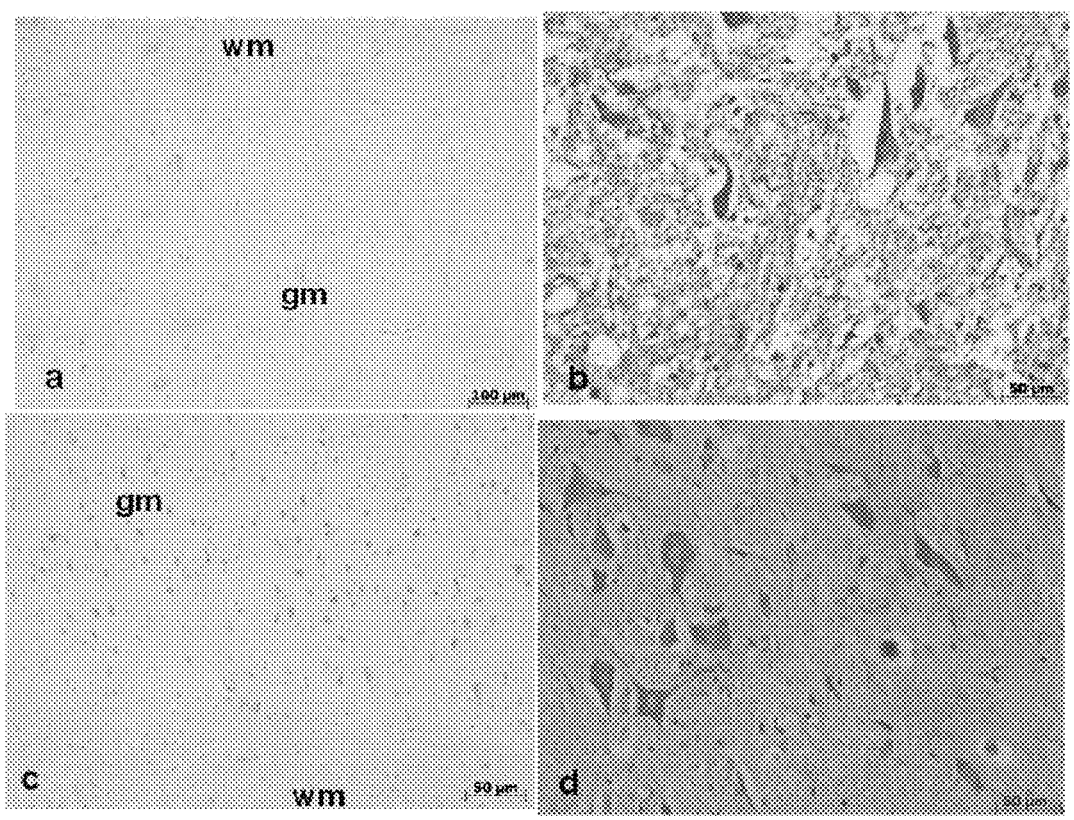
FIG. 35 shows immunohistochemical localization of iNOS (A) and nitrotyrosine (B). No positive staining for iNOS (a) and for nitrotyrosine (e) was observed in the spinal cord tissues collected from sham-operated mice. Administration of 17β-estradiol to SCI-operated mice produced a marked reduction in the immunostaining for iNOS (c) and nitrotyrosine (g) in spinal cord tissue, when compared to positive staining for iNOS (b) and nitrotyrosine (f) obtained from the spinal cord tissue of mice 24 hours after the injury. Co-administration of ICI 182,780 and 17β-estradiol significantly blocked the effect of the 17β-estradiol on iNOS (d) and nitrotyrosine (h). This figure is representative of at least 3 experiments performed on different experimental days. wm: White matter; gm: gray matter.
Figure 35B:
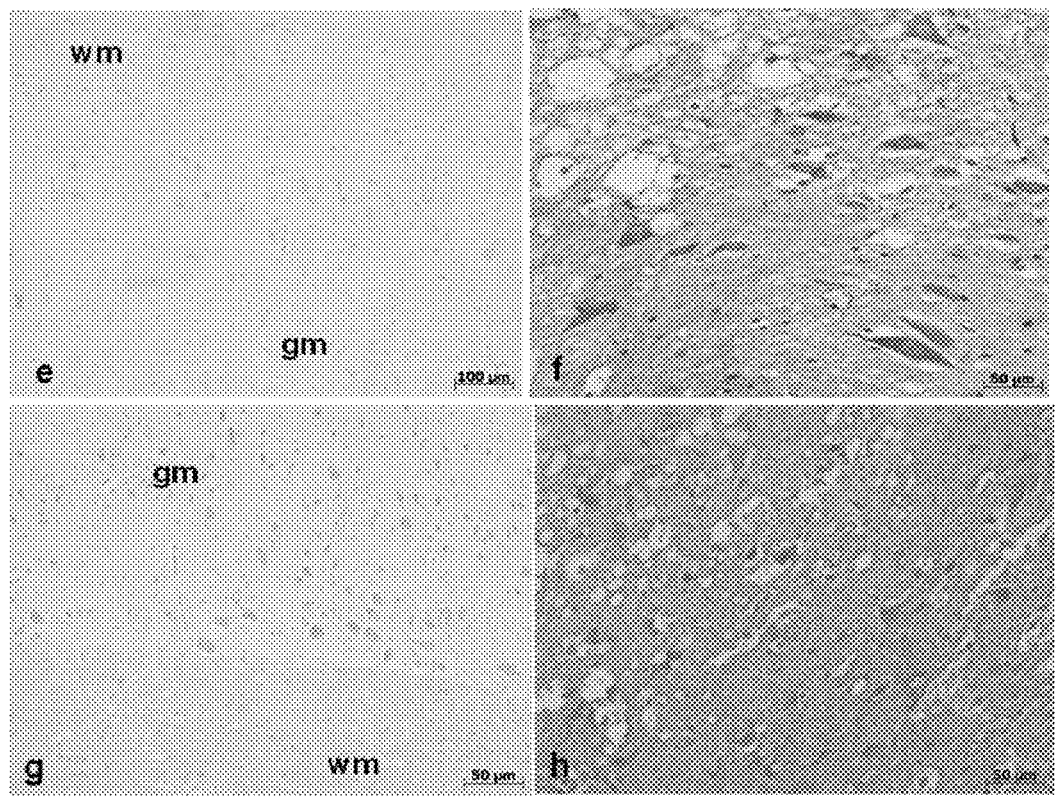

(d) 17β-estradiol Modulates Expression of iNOS and the Nitrotyrosine Formation After SCI Immunohistological staining for iNOS in the spinal cord was determined 24 hours after injury. Sections of spinal cord from sham-operated mice did not stain for iNOS (FIG. 35A see densitometry analysis FIG. 33), whereas spinal cord sections obtained from SCI control mice exhibited positive staining for iNOS (FIG. 35B see densitometry analysis FIG. 33) mainly localized in inflammatory cells as well as in nuclei of Schwann cells in the white and gray matter of the spinal cord tissues.

Treatment of mice subjected to SCI with 17β-estradiol reduced the degree of positive staining for iNOS (FIG. 35C see densitometry analysis FIG. 33) in the spinal cord. To determine the localization of "peroxynitrite formation" and/or other nitrogen derivatives produced during SCI, nitrotyrosine, a specific marker of nitrosative stress, was measured by immunohistochemical analysis in the spinal cord sections at 24 hours after SCI. Sections of spinal cord from sham-operated mice did not stain for nitrotyrosine (FIG. 35E see densitometry analysis FIG. 33), whereas spinal cord sections obtained from SCI control mice exhibited positive staining for nitrotyrosine (FIG. 35F see densitometry analysis FIG. 33) mainly localized in inflammatory cells as well as in nuclei of Schwann cells in the white and gray matter of the spinal cord tissues. Treatment of mice subjected to SCI with 17β-estradiol reduced the degree of positive staining for nitrotyrosine (FIG. 35G see densitometry analysis FIG. 33) in the spinal cord. Co-administration of ICI 182,780 and 17β-estradiol significantly blocked the effect of the 17β-estradiol on iNOS expression (FIG. 35D see densitometry analysis FIG. 33) and nitrotyrosine formation (FIG. 35H see densitometry analysis FIG. 33).

(e) 17β-estradiol Modulates Expression of COX-2 After SCI

Figures 36A, 36B, 36C, 36D:
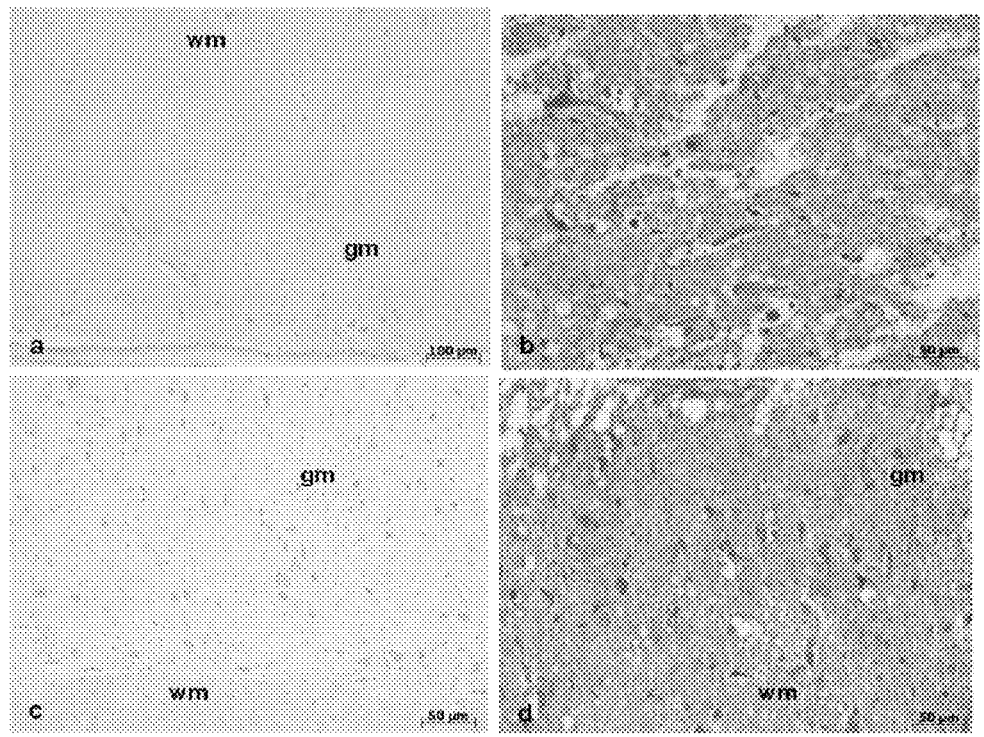
FIG. 36 shows immunohistochemical localization of COX-2. No positive staining for COX-2 (a) was observed in the spinal cord tissues collected from sham-operated mice. Administration of 17β-estradiol to SCI-operated mice produced a marked reduction in the immunostaining for COX-2 (c) in spinal cord tissue, when compared to positive staining for COX-2 (b) obtained from the spinal cord tissue of mice 24 h after the injury. Co-administration of ICI 182,780 and 17β-estradiol significantly blocked the effect of the 17β-estradiol on COX-2 (d). This figure is representative of at least 3 experiments performed on different experimental days. wm: White matter; gm: gray matter.

Immunohistological staining for COX-2 in the spinal cord was also determined 24 hours after injury. Sections of spinal cord from sham-operated mice did not stain for COX-2 (FIG. 36A see densitometry analysis FIG. 33), whereas spinal cord sections obtained from SCI control mice exhibited positive staining for COX-2 (FIG. 36B see densitometry analysis FIG. 33) mainly localized in inflammatory cells as well as in nuclei of Schwann cells in the white and gray matter of the spinal cord tissues. Treatment of mice subjected to SCI with 17β-estradiol reduced the degree of positive staining for COX-2 (FIG. 36C see densitometry analysis FIG. 33) in the spinal cord. Co-administration of ICI 182,780 and 17β-estradiol significantly blocked the effect of the 17β-estradiol on COX-2 expression (FIG. 36D see densitometry analysis FIG. 33).

(f) Effect of 17β-estradiol on Apoptosis in Spinal Cord After Injury

To test whether spinal cord damage was associated with cell death by apoptosis, TUNEL-like staining was measured in the perilesional spinal cord tissue. Almost no apoptotic cells were detected in the spinal cord from sham-operated mice. At 24 hours after the trauma, tissues obtained from SCI-operated mice demonstrated a marked appearance of dark brown apoptotic cells and intercellular apoptotic fragments (FIG. 37A TUNEL+cells were 3.01±0.13 per field,) associated with a specific apoptotic morphology characterized by the compaction of chromatin into uniformly dense masses in perinuclear membrane, the formation of apoptotic bodies as well as the membrane blebbing. In contrast, tissues obtained from mice treated with 17β-estradiol (FIG. 37B TUNEL+cells were 0.45±0.12 per field) demonstrated a small number of apoptotic cells or fragments. Co-administration of ICI 182,780 and 17β-estradiol significantly blocked the effect of the 17β-estradiol on the presence of apoptotic cell (FIG. 37C TUNEL+cells were 2.80±0.18 per field). Section d demonstrates the positive staining in the Kit positive control tissue.

(g) Effect of 17β-estradiol on Bax and Bcl-2 Expression

Figures 39A, 39B, 39C, 39D, 39E, 39F, 39G, 39H:
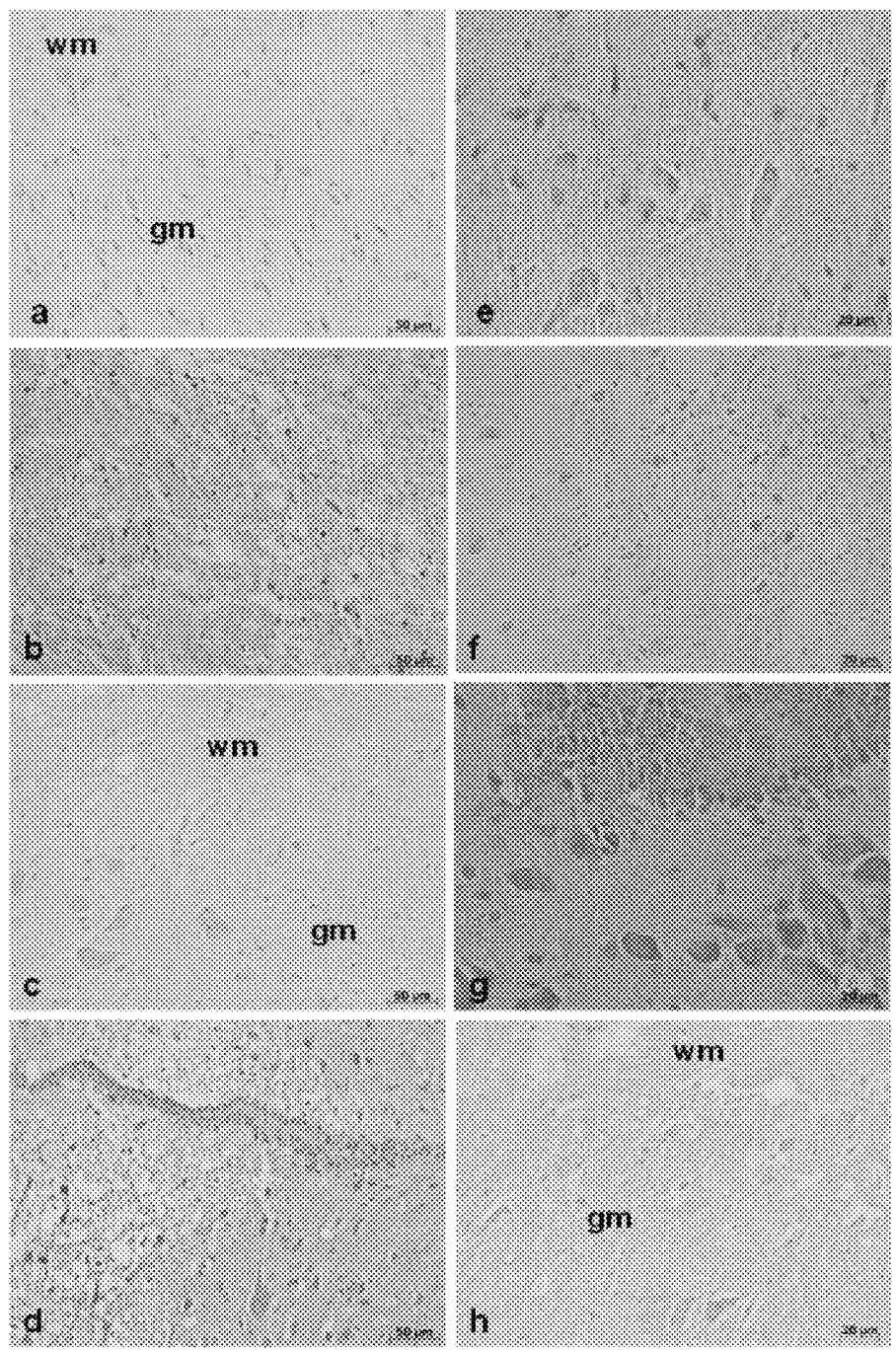
FIG. 39 shows immunohistochemical expression of Bax and Bcl-2. No positive staining for Bax was observed in the tissue section from sham-operated mice (a). SCI caused, at 24 hours, an increase in the release of Bax expression (b). Treatment with 17β-estradiol significantly inhibited the SCI-induced increase in Bax expression (c). On the contrary positive staining for Bcl-2 was observed in the spinal cord tissues of sham-operated mice (e). At 24 hours after SCI significantly less staining for Bcl-2 was observed (f). The 17β-estradiol treatment significantly prevents the loss of Bcl-2 expression induced by SCI (g). Co-administration of ICI 182,780 and 17β-estradiol significantly blocked the effect of the 17β-estradiol on Bax (d) and Bcl-2 (h). Figure is representative of at least 3 experiments performed on different experimental days. wm: White matter; gm: gray matter.
Figure 40:
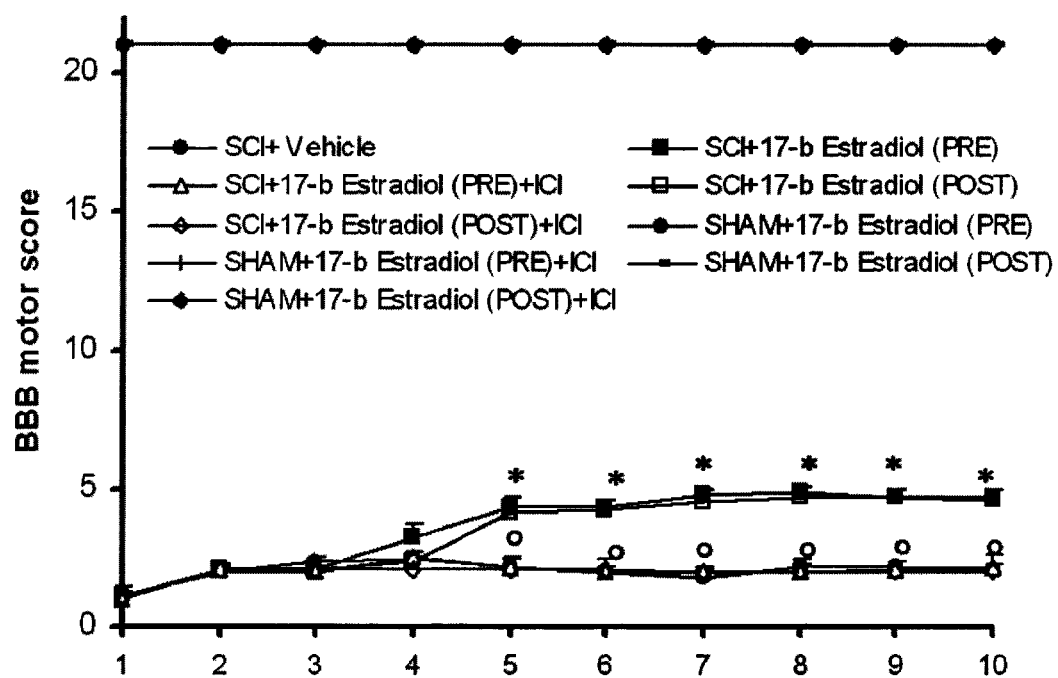
FIG. 40 shows the effect of 17β-estradiol on hind limb motor disturbance after spinal cord injury. The degree of motor disturbance was assessed every day for 10 days after SCI by Basso, Beattie, and Bresnahan criteria. Pre or post treatment with 17β-estradiol reduces the motor disturbance after SCI. Co-administration of ICI 182,780 and 17β-estradiol significantly blocked the effect of the 17β-estradiol on the motor disturbance after SCI. Values shown are mean±S.E. mean of 10 mice for each group. *$p<0.01$ vs. SCI; °$p<0.01$ vs. SCI+17β-estradiol.

The appearance of Bax in homogenates of spinal cord was investigated by Western blot at 24 hours after SCI. A basal level of Bax was detected in the spinal cord from sham-operated animals (FIG. 38A). Bax levels were substantially increased in the spinal cord from control mice subjected to SCI (FIG. 38A). On the contrary, 17β-estradiol treatment prevented the SCI-induced Bax expression (FIG. 38A). Co-administration of ICI 182,780 and 17β-estradiol significantly blocked the effect of the 17β-estradiol on Bax expression (FIG. 38A). To detect Bcl-2 expression, whole extracts from spinal cord of each rat were also analyzed by Western blot analysis. A low basal level of Bcl-2 expression was detected in spinal cord from sham-operated mice (FIG. 38B). Twenty four hours after SCI, the Bcl-2 expression was significantly reduced in whole extracts obtained from spinal cord of SCI control mice (FIG. 38B). Treatment of mice with 17β-estradiol significantly reduced the SCI-induced inhibition of Bcl-2 expression (FIG. 38B). Co-administration of ICI 182,780 and 17β-estradiol significantly blocked the effect of the 17β-estradiol on the Bcl2 expression (FIG. 38B). The samples of spinal cord tissue were also taken at 24 hours after SCI in order to determine the immunohistological staining for Bax and Bcl-2. Sections of spinal cord from sham-operated mice did not stain for Bax (FIG. 39A) whereas spinal cord sections obtained from SCI control mice exhibited a positive staining for Bax (FIG. 39B). 17β-estradiol treatment reduced the degree of positive staining for Bax in the spinal cord of mice subjected to SCI (FIG. 39C). In addition, sections of spinal cord from sham-operated mice demonstrated positive staining for Bcl-2 (FIG. 39D) while in SCI control mice the staining for Bcl-2 was significantly reduced (FIG. 39E). 17β-estradiol treatment attenuated the loss of positive staining for Bcl-2 in the spinal cord in mice subjected to SCI (FIG. 39F). Co-administration of ICI 182,780 and 17β-estradiol significantly blocked the effect of the 17β-estradiol on Bax (FIG. 39G) and Bcl-2 (FIG. 39H) expression.Effect of 17β-estradiol on motor function In order to elucidate the potential clinical significance of the protective effects of 17β-estradiol, it was investigated whether the pre or post-treatment with 17β-estradiol modified the motor dysfunction evaluated by the modified BBB hind limb locomotor rating scale score associated with SCI. While motor function was only slightly impaired in sham mice, mice subjected to SCI had significant deficits in hind limb movement (FIG. 40). A significant amelioration of hind limb motor disturbances was observed in 17β-estradiol-pretreated as well as post-treated mice (FIG. 40). Co-administration of ICI 182,780 and 17β-estradiol significantly blocked the effect of the 17β-estradiol on the motor recovery (FIG. 40).

d) Discussion and Conclusions

SCI induces lifetime disability, and no suitable therapy is available to treat victims or to minimize their sufferings. 17β-estradiol has been shown to be therapeutic in a variety of models of neurological disease including SCI (Sribnick 2005). In this study, it is shown that 17β-estradiol exerts beneficial effects in a mouse model of SCI. In particular, it was demonstrated that 17β-estradiol reduced: (1) the degree of spinal cord damage; (2) infiltration of neutrophils; (3) pro-inflammatory cytokine and chemokine expression; (4) expression of iNOS, nitrotyrosine, and COX-2; and (5) apoptosis.

It is well known that a significant increase in percentage of water in spinal cord tissue occurs after injury (Hsu 1985). In this study, it was observed by histological examination that the increase in tissue water was prevented by estrogen pre-treatment. SCI induced by the application of vascular clips to the dura via a four-level T5-T8 laminectomy resulted in edema and loss of myelin in lateral and dorsal funiculi. This histological damage was associated with the loss of motor function. In this study, it was demonstrated that 17β-estradiol pre-treatment significantly reduced the SCI-induced spinal cord tissue alteration as well as improved the motor function. A number of studies have clearly demonstrated that after SCI, an inflammatory response characterized by the infiltration of neutrophils and the activation of microglia develops within hours (McTigue 2002). This primary event is followed by a second wave of response to localize the inflammatory response within the spinal cord tissue and to down regulate this response. It was shown that using MPO activity assay the infiltration of neutrophils at 24 h after SCI was confirmed. Moreover, administration of 17β-estradiol reduces the infiltration of neutrophils when compared to the SCI control group. The recruitment of inflammatory cells like neutrophils is responsible for the production of several immunomodulatory factors, such as cytokines and lipid mediators. Among the cytokines, TNF-α and IL-1 are paradigmatic pro-inflammatory mediators responsible for leukocyte activation and recruitment (Maier 2005). Furthermore, there is good evidence that TNF-α and IL-1α are clearly involved in the pathogenesis of SCI (Genovese 2006). Moreover, it has been demonstrated that in SCI the expression of proinflammatory cytokines, including TNF-α and IL-1α, at the site of injury regulates the precise cellular events after spinal cord injury. In the present study, a significant increase of TNF-α IL-1β, IL-6 and MCP-1 have clearly been demonstrated in spinal cord tissues at 24 hours after SCI. Treatment with 17β-estradiol significantly reduced the expression of TNF-α, IL-1β and MCP-1. It has also been shown that cytokines also play an important role in the induction of inducible nitric oxide synthase (iNOS) which is known to play an important role in the development of SCI (Matsuyama 1998). Our results indicated that 17β-estradiol treatment reduces the expression of iNOS in SCI-operated mice and that the attenuation of the induction of iNOS expression observed in SCI-operated mice which are treated with 17β-estradiol is secondary to a reduced formation of endogenous TNF-α and IL-1β. Like iNOS, the expression of COX-2 is also mediated by TNF-a and IL-1 (Tonai 2006). In the pathological processes of acute SCI the upregulation of COX-2, a key enzyme in the synthesis of prostaglandins (PGs), has also been postulated to be involved. It is well known that COX-1 and COX-2 mRNA and protein are present in the spinal cord tissue and that COX-2 protein is expressed in white matter astrocytes during basal conditions (Beiche 1998). Conditions related to inflammation and pain induces COX-2 expression, which may be widespread (Venegas 2003). The results demonstrated that in sections of spinal cord of 17β-estradiol-treated mice, there is a markedly less positive staining for COX-2 when compared with that of saline+SCI sham mice. Our results, in agreement with others' observation (29) demonstrated a relationship between TNF-α production and the COX-2 expression. In addition to prostaglandins and NO, several studies have implicated the formation of reactive oxygen species (ROS) and reactive nitrogen species (RNS) in the secondary neuronal damage of SCI (Xu 2001). In particular it has been demonstrated that peroxynitrite likely contributes to secondary neuronal damage through pathways resulting from the chemical modification of cellular proteins and lipids (Xu 2001). To confirm the pathological contributions of peroxynitrite to secondary damage after SCI, the nitrotyrosine formation was evaluated in the injured tissue. The results showed that the immunostaining for nitrotyrosine was reduced in SCI-operated mice treated with 17β-estradiol. Nitrotyrosine formation, along with its detection by immunostaining, was initially proposed as a relatively specific marker for the detection of the endogenous formation "footprint"ofperoxynitrite (Beckman 1996). There is, however, recent evidence that certain other reactions can also induce tyrosine nitration; e.g., the reaction of nitrite with hypochlorous acid and the reaction of myeloperoxidase with hydrogen peroxide can lead to the formation of nitrotyrosine (Endoh 1994). Increased nitrotyrosine staining is considered, therefore, as an indication of "increased nitrosative stress" rather than a specific marker of the peroxynitrite generation. Recent studies have demonstrated the induction of apoptosis in different cell line in response to ROS, peroxynitrite and nitric oxide (Merrill 1993). In the present study, using the TUNEL coloration it was clearly confirmed that 17β-estradiol plays an important role in the attenuation of apoptosis during SCI. Moreover, it is well known that Bax, a pro-apoptotic gene, plays an important role in developmental cell death (Chittenen 1994) and in CNS injury. Similarly, it has been shown that the administration of Bcl-xL fusion protein, (Bcl-2 is the most expressed antiapoptotic molecule in adult central nervous system) into injured spinal cords significantly increased neuronal survival, showing that SCI-induced changes in Bcl-xL contribute considerably to neuronal death (Nesic-Taylor 2005). Base on these evidences, proapoptotic transcriptional changes, including upregulation of proapoptotic Bax and down regulation of antiapoptotic Bcl-2, were identified using Western blot assay and by immunohistochemical staining. The results demonstrate that treatment with 17β-estradiol prior to SCI prevents the loss of the antiapoptotic way and reduced the proapoptotic pathway activation. Estrogens have been reported to have anti-oxidative activities, which might in part explain some of the findings reported in the present study. However, the antioxidant activity of 17β-estradiol is observed at pharmacological concentrations of the hormone and is not blocked by antagonists of the estrogen receptors. It thus appears that the lack of spinal cord tissue injury in 17β-estradiol pre-treated mice reported here is not due to estrogen's anti-oxidant action because mice were treated with a dose of the hormone at which is not anti-oxidant as well as more importantly the observed protective effects of 17β-estradiol were abrogated by the co-administration of the antagonist of estrogen receptor, ICI 82,780. The observed effects are therefore receptor-mediated.

Throughout this application, various publications are referenced. The disclosures of these publications in their entireties are hereby incorporated by reference into this application in order to more fully describe the state of the art to which this invention pertains.

REFERENCES

1. Ahmed S T and Ivashkiv L B. Inhibition of IL-6 and IL-10 signaling and Stat activation by inflammatory and stress path-ways. J Immunol 165: 5227-5237 (2000).
2. Angele M K, Xu Y X, Ayala A, Schwacha M G, Catania R K, Cioffi W G, Bland K I, and Chaudry I H. Gender dimorphism in trauma-hemorrhage-induced thymocyte apoptosis. Shock 12:316-322 (1999).
3. Angele M K, Knoferl M W, Schwacha M G, et al. Sex steroids regulate pro- and anti-inflammatory cytokine release by macrophages after trauma-hemorrhage. Am J Physiol 277: C35-C42 (1999).
4. Angele M K, Smail N, Wang P, et al. L-arginine restores the depressed cardiac output and regional perfusion after trauma-hemorrhage. Surgery 124:394-401 (1998).
5. Angele M K, Ayala A, Monfils B A, Cioffi W G, Bland K I, and Chaudry Testosterone and/or low estradiol: normally required but harmful immunologically for males after trauma-hemorrhage. J Trauma 44: 78-85 (1998).
6. Angele M K, Wichmann M W, Ayala A, et al. Testosterone receptor blockade following hemorrhage in males. Restoration of the depressed immune functions and improved survival after subsequent sepsis. Arch Surg 132:1207-1214 (1997).
7. Ayala A, Lehman D L, Herdon C D, et al. Mechanism of enhanced susceptibility to sepsis after hemorrhage: Interleukin (IL)-10 suppression of T-cell response is mediated by eicosanoid induced IL-4 release. Arch Surg 129:1172-1178 (1994).
8. Ayala A, Perrin M M, Kisala J M, et al. Polymicrobial sepsis selectively activates peritoneal but not alveolar macrophage to release inflammatory mediators (IL-1, IL-6 and TNF). Circ Shock 36:191-199 (1992).
9. Ayala A, Perrin M M, Chaudry I H. Defective macrophage antigen presentation following haemorrhage is associated with the loss of MHC class II (Ia) antigens. Immunology 70:33-39 (1990).
10. Ayala A, Perrin M M, Ertel W, et al. Differential effects of haemorrhage on Kupffer cells: decreased antigen presentation despite increased inflammatory cytokine (IL-1, IL-6 and TNF) release. Cytokine 4:66-75 (1992).
11. Ayala A, Perrin M M, Chaudry I H. Increased susceptibility to sepsis following hemorrhage: Defective Kupffer cell mediated antigen presentation. Surg Forum 40:102-104 (1989).
12. Ayala A, Perrin M M, Wagner M A., et al. Enhanced susceptibility to sepsis after simple hemorrhage: Depression of Fc and C3b receptor mediated phagocytosis. Arch Surg; 125:70-75 (1990).
13. Ayala A, Perrin M M, Wang P, et al. Hemorrhage induces enhanced Kupffer cell cytotoxicity while decreasing peritoneal or splenic mac-rophage capacity: involvement of cell-associated TNF and reactive nitrogen. J Immunol 147: 4147-4154 (1991).
14. Baker C C, Chaudry I H, Gaines H O, et al. Evaluation of factors affecting mortality rate after sepsis in murine cecal ligation and puncture model. Surgery 94:331-335 (1983).
15. Barton R G and Cerra F B. Initial management of trauma. The first 5 minutes. Postgrad Med 88: 83-90 (1990).
16. Baue A E, Durham R, Faist E. Systemic inflammatory response syndrome (SIRS), multiple organ dysfunction syndrome (MODS), multiple organ failure (MOF): are we winning the battle? Shock ; 10:79-89 (1998).
17. Baumann H, Prowse K R, Marinkovic S, Won K A, and Jahreis G P. Stimulation of hepatic acute phase response by cytokines and glucocorticoids. Ann NY Acad Sci 557:280-295 (1989).
18. Bone R C. Toward an epidemiology and natural history of SIRS (systemic inflammatory response syndrome). JAMA 268:3452-3455 (1992).
19. Bynoe M S, Grimaldi C M, Diamond B. Estrogen up-regulates Bcl-2 and blocks tolerance induction of naive B cells. Proc Natl Acad Sci USA 97:2703-2708 (2000).
20. Caulin-Glaser T, Garcia-Cardena G, Sarrel P, Sessa W C, and Bender JR. 17b-Estradiol regulation of human endothelial cell basal nitric oxide release, independent of cytosolic $Ca^{-1}$ mobilization. Circ Res 81: 885-892 (1997).
21. Chaudry I H, Ayala A. Immunological aspects of hemorrhage. Austin, Tex.: Medical Intelligence Unit; R. G. Landes Co.,1-132 (1992)
22. Chaudry I H, Wang P, Singh G, Hauptman J G, and Ayala A. Rat and mouse models of hypovolemic-traumatic shock. In: Pathophysiology of Shock: Sepsis and Organ Failure, edited by Schlag G and Redl H. Berlin: Springer-Verlag, p. 371-383 (1993).
23. Chaudry I H, Ayala A, Ertel W, Stephan R N. Hemorrhage and resuscitation: immunological aspects. Am J Physiol 259:R663-R678 (1990).
24. Chen Z, Yuhanna I S, Galcheva-Gargova Z, Karas R H, Mendelsohn M E, and Shaul P W. Estrogen receptor a mediates the nongenomic activation of endothelial nitric oxide synthase by estrogen. J Clin Invest 103: 401-406 (1999).
25. Deshpande R, Khalili H, Pergolizzi R G, et al. Estradiol down-regulates LPS-induced cytokine production and NF B activation in murine macrophages. Am J Reprod Immunol 1997; 38:46-54.
26. Diano S, Horvath T L, Mor G, et al. Aromatase and estrogen receptor immunoreactivity in the coronary arteries of monkeys and human subjects. Menopause; 6:21-28 (1999).
27. Diodato M D, Knöferl M W, Schwacha M G, et al. Gender differences in the inflammatory response and survival following haemorrhage and subsequent sepsis. Cytokine 14:162-169 (2000).
28. Diodato M D, Knöferl M W, Angele M K, Schwacha M G, Ci-offi W G, Bland K I, and Chaudry I H. Females tolerate the deleterious consequences of hemorrhage better than males (Abstract). Shock 11: 68 (1999).
29. Douketis J D, Gordon M, Johnston M, et al. The effects of hormone replacement therapy on thrombin generation, fibrinolysis inhibition, and resistance to activated protein C: prospective cohort study and review of literature. Thromb Res 99:25-34 (2000).
30. Dubal D B, Shughrue P J, Wilson M E, et al. Estradiol modulates bcl-2 in cerebral ischemia: a potential role for estrogen receptors. J Neurosci 19:6385-6393 (1999).

31. Eachempati S R, Hydo L, Bane P S. Gender-based differences in outcome in patients with sepsis. *Arch Surg* 134:1342-1347 (1999).

32. Echeverria O M, Gonzalez M A, Traish A M, et al. Immuno-electron microscopic localization of estradiol receptor in cells of male and female reproductive and non-reproductive organs. *Biol Cell;* 81:257-265 (1994).

33. Ertel W, Morrison M H, Ayala A, et al. Chloroquine attenuates hemorrhagic shock induced suppression of Kupffer cell antigen presentation and MHC class II antigen expression through blockade of tumor necrosis factor and prostaglandin release. *Blood* 78:1781-1788 (1991).

34. Ertel W, Morrison M H, Ayala A, et al. Biological significance of elevated TNF levels: in vivo administration of monoclonal antibody against TNF after haemorrhage shock increases the capacity of macrophages to release TNF while restoring immunoresponsiveness. *Cytokine* 6:624-632 (1994).

35. Evans M J, MacLaughlin S, Marvin R D, et al. Estrogen decreases in vitro apoptosis of peripheral blood mononuclear cells from women with normal menstrual cycles and decreases TNF-alpha production in SLE but not in normal cultures. *Clin Immunol Immunopathol* 82:258-262 (1997).

36. Everson G T. Gastrointestinal motility in pregnancy. *Gastroenterol Clin North Am* 21:751-776 (1992).

37. Fraser H, Davidge S T, Clanachan A S. Enhancement of post-ischemic myocardial function by chronic 17b-estradiol treatment: role of alterations in glucose metabolism. *J Mol Cell Cardiol* 31:1539-1549 (1999).

38. Frazier-Jessen M R, Mott F J, Witte P L, et al. Estrogen suppression of connective tissue deposition in a murine model of peritoneal adhesion formation. *J Immunol* 156: 3036-3042 (1996).

39. Freay A D, Curtis S W, Korach K S, and Rubanyi G M. Mech-anism of vascular smooth muscle relaxation by estrogen in depolarized rat and mouse aorta. Role of nuclear estrogen receptor and Ca-1 uptake. *Circ Res* 81: 242-248 (1997).

40. Gohel A, McCarthy M B, Gronowicz G. Estrogen prevents glucocor- ticoid-induced apoptosis in osteoblasts in vivo and in vitro. *Endocrinology* 140:5339-5347 (1999).

41. Gregory M S, Duffner L A, Faunce D E, et al. Estrogen mediates the sex difference in post-burn immunosuppression. *J Endocrinol* 164:129-138 (2000).

42. Gulshan S, McCruden A B, and Stimson W H. Oestrogen receptors in macrophages. *Scand J Immunol* 31: 691-697 (1990).

43. Hauptman J G, Wang P, DeJong G K, and Chaudry N. Improved methodology for the evaluation of the velocity of clearance of indocyanine green in the rat. *Circ Shock* 33: 26-32 (1991).

44. Hauptman J G, DeJong G K, Blasko K A, Chaudry I H. Measurement of hepatocellular function, cardiac output, effective blood volume, and oxygen saturation in rats. *Am J Physiol* 257:R439-R444 (1989).

45. Harbrecht B G, Wu B, Watkins S C, Marshall H P Jr, Peitz man A B, and Billiar T R. Inhibition of nitric oxide synthase during hemorrhagic shock increases hepatic injury. *Shock* 4:332-337 (1995).

46. Hierholzer C, Harbrecht B, Menezes J M, Kane J, Mac-Micking J, Nathan C F, Peitzman A B, Billiar T R, and Tweardy D J. Essential role of induced nitric oxide in the initiation of the inflammatory response after hemorrhagic shock. *J Exp Med* 187: 917-928 (1998).

47. Hobbs M V, Weigle W O, Noonan D J, Torbett B E, McEvilly R J, Koch R J, Cardenas G J, and Ernst D N. Patterns of cytokine gene expression by CD41 T cells from young and old mice. *J Immunol* 150: 3602-3614 (1993).

48. Hofmann-Lehmann R, Holznagel E, and Lutz H. Female cats have lower rates of apoptosis in peripheral blood lympho-cytes than male cats: correlation with estradiol-17β, but not with progesterone blood levels. *Vet Immunol Immunopathol* 65: 151-

49. 160 (1998).

50. Homo-Delarche F, Fitzpatrick F, Christeff N, et al. Sex steroids, glucocorticoids, stress and autoimmunity. *J Steroid Biochem Mol Biol;* 40:619- 637 (1991).

51. Howard M, O'Garra A, Ishida H, et al. Biological properties of interleukin 10. *J Clin Immunol* 12:239-247 (1992).

52. Howard M and O'Garra A. Biological properties of interleukin-10. *Immunol Today* 13:198-200 (1992).

53. Ihle J N, Keller J, Greenberger J S, Henderson L, Yetter R A, and Morse H C. Phenotypic characteristics of cell lines requiring IL-3 for growth. *J Immunol* 129:1377-1383 (1982).

54. Jarrar D, Wang P, Cioffi W G, Bland K I, Chaudry I H. The female reproductive cycle is an important variable in the response to trauma-hemorrhage. *Am J Physiol Heart Circ Physiol* 279(3):H1015-H1021 (2000).

55. Jarrar D, Wang P, Knoferl M W, Kuebler J F, Cioffi W G, Bland Ki, Chaudry I H. Insight into the mechanism by which estradiol improves organ functions after trauma-hemorrhage. *Surgery* 128(2):246-25 (2000)

56. Jarrar D, Wang P, Song G Y, Knoferl M W, Cioffi W G, Bland K I, and Chaudry I H. Metoclopramide: a novel adjunct for improving cardiac and hepatocellular functions after trauma- hemorrhage. Am J Physiol Endocrinol Metab 278: E90-E95 (2000).

57. Jarrar D, Chaudry I H, and Wang P. Organ dysfunction following hemorrhage and sepsis: mechanisms and therapeutic approaches. *Int J Mol Med* 4: 575-583 (1999).

58. Jarrar D, Wang P, Cioffi W G, et al. The female reproductive cycle is an important variable in the response to trauma-hemorrhage and re-suscitation [abstract]. *Shock* 11(suppl1):70 (1999).

59. Kahlke V, Angele M K, Ayala A, et al. Immune dysfunction following trauma-haemorrhage: influence of gender and age. *Cytokine* 12:69-77 (2000).

60. Kahlke V, Angele M K, Schwacha M G, et al. Reversal of sexual dimorphism in splenic T lymphocyte responses after trauma-hemorrhage with aging. *Am J Physiol Cell Physiol;* 278:C509-0516 (2000).

61. Kahlke V, Angele M K, Schwacha M G, Ayala A, Cioffi W G, Bland K I, and Chaudry I H. Gender and age are important factors that influence immune responses after trauma-hemorrhage (Abstract). *Shock* 11, Suppl 1: 70 (1999).

62. Karas R H and Mendelsohn M E. Rapid vasomotor effects of estrogen: men are part of the club. Chest 114: 1508-1509 (1998).

63. Kerger H, Waschke K F, Ackern K V, Tsai A G, and Intaglietta M. Systemic and microcirculatory effects of autologous whole blood resuscitation in severe hemorrhagic shock. *Am J Physiol Heart Circ Physiol* 276: H2035-H2043 (1999).

64. Kitazawa T, Hamada E, Kitazawa K, and Gaznabi A K. Non-genomic mechanism of 17β-oestradiol-induced inhibition of contraction in mammalian vascular smooth muscle. *J Physiol* (Lond) 499: 497-511 (1997).

65. Knöferl M, Angele M K, Diodato M D, Schwacha M G, Ayala A, Cioffi W G, Bland K I, Chaudry Ho Female sex hormones regulate macrophage function after trauma-hemorrhage and prevent increased death rate from subsequent sepsis. *Ann Surg* 235:105-112 (2002).

66. Knöferl M, Jarrar D, Angele M K, Ayala A, Schwacha M G, Bland K I, Chaudry I H. 171~estradiol normalizes 67. Knöferl M W, Diodato M D, Angele M K, et al. Do female sex steroids adversely or beneficially affect the depressed immune responses in males after trauma-hemorrhage? *Arch Surg* 135:425-433 (2000).

68. Knöferl M W, Angele M K, Diodato M D, Ayala A, Cioffi W G, Bland K I, and Chaudry I H. Surgical ovariectomy produces immunodepression following trauma-hemorrhage and increases mortality from subsequent sepsis. *Surg Forum* 50: 235-237 (1999).

69. LaFlamme A C, MacDonald A S, and Pearce E J. Role of IL-6 in directing the initial immune response to schistosome eggs. *J Immunol* 164: 2419-2426 (2000).

70. Lantin-Hermoso R L, Rosenfeld C R, Yuhanna I S, German Z, Chen Z, and Shaul P W. Estrogen acutely stimulates nitric oxide synthase activity in fetal pulmonary artery endothelium. *Am J Physiol Lung Cell Mol Physiol* 273: L119-L126 (1997).

71. Lefer A M. Endotoxin, cytokines, and nitric oxide in shock. *Shock* 1:79-80 (1994).

72. Lindner V, Kim S K, Karas R H, Kuiper G G, Gustafsson J A, and Mendelsohn M E. Increased expression of estrogen receptor-b mRNA in male blood vessels after vascular injury. *Circ Res* 83: 224-229 (1998).

73. McGowan J E, Barnes M W, Finland N. Bacteremia at Boston City Hospital: occurrence and mortality during 12 selected years (1935-972) with special reference to hospital-acquired cases. *J Infect Dis* 132:316-335 (1975).

74. McLauchlan G J, Anderson I D, Grant I S, et al. Outcome of patients with abdominal sepsis treated in an intensive care unit. *Br J Surg* 82:524-529 (1995).

75. Meldrum D R, Ayala A, Perrin M M, Ertel W, and Chaudry I H. Diltiazem restores IL-2, IL-3, IL-6 and IFN-γ synthesis and decreases susceptibility to sepsis following hemorrhage. *J Surg Res* 51: 158-164 (1991).

76. Mendelsohn M E and Karas R H. The protective effects of estrogen on the cardiovascular system. *N Engl J Med* 340:1801-1811 (1999).

77. Miller R A. Cellular and biochemical changes in the aging mouse immune system. *Nutr Rev* 53: S8-S14 (1995).

78. Mizel S B. Production and quantitation of lymphocyte-activating factor (interleukin 1). In: Manual of Macrophage Methodology, edited by Herscowitz H B, Holden H T, Bellanti J A, and Ghaffar A. New York: Dekker, p. 407-441 (1981).

79. Mizushima Y, Wang P, Jarrar D, Cioffi W G, Bland K I, Chaudry I H. Estradiol administration following trauma-hemorrhage improves cardiovascular and hepatocellular functions in males. *Ann Surg* 232: 673-679 (2000).

80. Mizushima Y, Wang P, Jarrar D, Cioffi W G, Bland K I, and Chaudry I H. Preinduction of heat shock proteins protects cardiac and hepatic functions following trauma and hemorrhage. *Am J Physiol Regulatory Integrative Comp Physiol* 278: R352-R359 (2000).

81. Mossalayi M D, Dalloul A H, Bertho J M, Lecron J C, deLaforest P G, and Debre P. In vitro differentiation and proliferation of purified human thymic and bone marrow CD71 CD22 T-cell precursors. *Exp Hematol* 18: 326-331 (1990).

82. Nathan L, Pervin S, Singh R, Rosenfeld M, and Chaudhuri G. Estradiol inhibits leukocyte adhesion and transendothelial migration in rabbits in vivo: possible mechanisms for gender differences in atherosclerosis. *Circ Res* 85: 377-385 (1999).

83. Noppens R R, Kofler J, Hurn P D, Traystman R J. Dose-dependent neuroprotection by 17beta-estradiol after cardiac arrest and cardiopulmonary resuscitation. *Crit Care Med* 33(7):1595-1602 (2005).

84. Ogle T F, Kitay J I. Ovarian and adrenal steroids during pregnancy and the oestrous cycle in the rat. *J Endocrinol* 74:89-98 (1977).

85. O'Neill P J, Ayala A, Wang P, et al. Role of Kupffer cells in interleu-kin-6 release after trauma-hemorrhage and resuscitation. *Shock* 1:43-47 (1994).

86. Papanicolaou D A, Wilder R L, Manolagas S C, and Chrousos G P. The pathophysiologic roles of interleukin-6 in human disease. *Ann Intern Med* 128: 127-137 (1998).

87. Pines A, Eckstein N, Dotan I, et al. Effect of estradiol on rat ileum. *Gen Pharmacol* 31:735-736 (1998).

88. Purtilo D T, Hallgren H M, Yunis E J. Depressed maternal lymphocyte response to phytohaemagglutinin in human pregnancy. *Lancet* 1:769-771 (1972).

89. Ramachandran C, Catelli M G, Schneider W, and Shyamala G. Estrogenic regulation of uterine 90-kilodalton heat shock protein. *Endocrinology* 123:956-961 (1988).

90. Remmers D E, Cioffi W G, Bland K I, Wang P, Angele M K, and Chaudry I H. Testosterone: the crucial hormone responsible for depressing myocardial function in males after trauma-hemorrhage. *Ann Surg* 227: 790-799 (1998).

91. Remmers D E, Wang P, Cioffi W G, et al. Chronic resuscitation after trauma-hemorrhage and acute fluid replacement improves hepatocellular function and cardiac output. *Ann Surg* 227:112-119 (1998).

92. Remmers D E, Wang P, Cioffi W G, Bland K I, and Chaudry I H. Testosterone receptor blockade after trauma-hemorrhage improves cardiac and hepatic functions in males. *Am J Physiol Heart Circ Physiol* 273: H2919-H2925 (1997).

93. Robinson D A, Wang P, and Chaudry I H. Pentoxifylline re-stores the depressed cardiac performance after trauma-hemorrhage and resuscitation. *J Surg Res* 66: 51-56 (1996).

94. Rossouw J E. Hormone replacement therapy and cardiovascular disease. *Curr Opin Lipidol* 10:429-434 (1999).

95. Samy T S, Schwacha M G, Cioffi W G, Bland K I, and Chaudry I H. Androgen and estrogen receptors in splenic T lymphocytes: effects of flutamide and trauma-hemorrhage. *Shock* 14: 465-470 (2000).

96. Schneider E M, Lorenz I, Leippold S, Zischler H, Clark S C, and Wernet P. Generation of mature CD31 and T cell receptor 1 T cells from a leukemic analogue of the putative human (TCR) stem cell by T cell conditioned medium containing IL-3, IL-2, and GM-CSF. *Leukemia* 2: 282-289 (1988).

97. Schroder J, Kahlke V, Staubach K H, Zabel P, and Stuber F. Gender differences in human sepsis. *Arch Surg* 133: 1200-1205 (1998).

98. Schwacha M G, Knöferl M W, Samy TSA, et al. The immunologic consequences of hemorrhagic shock. *Crit Care Shock* 2:42-64 (1999).

99. Slimmer L M and Blair M L. Female reproductive cycle influences plasma volume and protein restitution after hemorrhage in the conscious rat. *Am J Physiol Regulatory Integrative Comp Physiol* 271: R626-R633 (1996).

100. Smith M S, Freeman M E, and Neill J D. The control of progesterone secretion during the estrous cycle and early pseudo- pregnancy in the rat: prolactin, gonadotropin and steroid levels associated with rescue of the corpus luteum of pseudopregnancy. *Endocrinology* 96: 219-226 (1975).

101. Stampfer M J, Colditz G A, Willett W C, et al. Post-menopausal estrogen therapy and cardiovascular disease: ten-year follow-up from the nurses' health study. *N Engl J Med* 325:756-762 (1991).

102. Starr R, Willson T A, Viney E M, Murray L J, Rayner J R, Jenkins B J, Gonda T J, Alexander W S, Metcalf D, Nicola N A, and Hilton D J. A family of cytokine-inducible inhibitors of signalling. *Nature* 387: 917-921 (1997).

103. Stephan R N, Kupper T S, Geha A S, Baue A S, and Chaudry I H. Hemorrhage without tissue trauma produces immunosup pression and enhances susceptibility to sepsis. *Arch Surg* 122:62-68 (1987).

104. Tilg H, Trehu E, Atkins M B, Dinarello C A, and Mier J W. Interleukin-6 (IL-6) as an anti-inflammatory cytokine: induction of circulating IL-i receptor antagonist and soluble tumor necro- sis factor receptor p55. *Blood* 83: 113-118 (1994).

105. Trinchieri G. Interleukin-12 and its role in the generation of TH1 cells. *Immunol Today* 14: 335-338 (1993).

106. Wang P, Ba Z F, Jarrar D, Cioffi W G, Bland K I, and Chaudry I H. Mechanism of adrenal insufficiency following trauma and severe hemorrhage: role of hepatic 11b-hydroxysteroid dehydrogenase. *Arch Surg* 134: 394-401 (1999).

107. Wang W, Wang P, Chaudry I H. Intestinal alkaline phosphatase: role in the depressed gut lipid transport after trauma-hemorrhagic shock. *Shock* 8:40-44 (1997).

108. Wang P, Ba Z F, Lu M C, Ayala A, Harkema J M, and Chaudry I H. Measurement of circulating blood volume in vivo after trauma-hemorrhage and hemodilution. *Am J Physiol Regulatory Integrative Comp Physiol* 266: R368-R374 (1994).

109. Wang P and Chaudry I H. Crystalloid resuscitation restores but does not maintain cardiac output following severe hemorrhage. *J Surg Res* 50: 163-169 (1991).

110. Wang P, Hauptman J G, and Chaudry I H. Hepatocellular dysfunction occurs early after hemorrhage and persists despite fluid resuscitation. *J Surg Res* 48:464-470 (1990).

111. Watanakunakorn C. *Staphylococcus aureus* endocarditis at a commu-nity teaching hospital, 1980 to 1991. An analysis of 106 cases. *Arch Intern Med* 154:2330-2335 (1994).

112. Wichmann M W, Ayala A, Chaudry I H. Male sex steroids are respon-sible for depressing macrophage immune function after trauma-hemorrhage. *Am J Physiol* 273:C1335-C1340 (1997).

113. Wichmann M W, Angele M K, Ayala A, et al. Flutamide. A novel agent for restoring the depressed cell-mediated immunity following soft-tissue trauma and hemorrhagic shock. *Shock* 8:1-7 (1997).

114. Wichmann M W, Angele M K, Ayala A, Cioffi W G, and Chaudry I H. Flutamide: a novel agent for restoring the depressed cell-mediated immunity following soft-tissue trauma and hemorrhagic shock. *Shock* 8: 1-7; 242-248 (1997).

115. Wichmann M W, Zellweger R, DeMaso C M, et al. Enhanced immune responses in females as opposed to decreased responses in males following hemorrhagic shock. *Cytokine* 8:853-863 (1996).

116. Wichmann M W, Zellweger R, DeMaso C M, et al. Mechanism of immunosuppression in males following trauma-hemorrhage: critical role of testosterone. *Arch Surg;* 131:1186-1191 (1996).

117. Xu Y X, Ayala A, Chaudry I H. Prolonged immunodepression after trauma and hemorrhagic shock. *J Trauma* 44:335-341 (1998).

118. Zellweger R, Wichmann W, Ayala A, Stein S, DeMaso C M, Chaudry I H. Females in proestrus state maintain splenic immune functions and tolerate sepsis better than males. *Crit Care Med* 25:106-110 (1997).

119. Zellweger R, Zhu X-H, Wichmann M W, et al. Prolactin administration following hemorrhagic shock improves macrophage cytokine release capacity and decreases mortality from subsequent sepsis. *J Immunol* 157:5748-5754 (1996).

120. Zellweger R, Ayala A, DeMaso C M, and Chaudry I H. Trauma-hemorrhage causes prolonged depression in cellular immunity. *Shock* 4: 149-153 (1995).

121. Maegele M, Riess P, Sauerland S, Bouillon B, Hess S, McIntosh T K, Mautes A, Brockmann M, Koebke J, Knifka J, Neugebauer E A: Characterization of a new rat model of experimental combined neurotrauma. *Shock* 23: 476-48 1, 2005.

122. Balentine J D: Hypotheses in spinal cord trauma research. In: Becker D P & Povlishock J T, (eds). Central Nervous System Trauma Status Report: NIH Bethesda Md. pp 455-461, 1985.

123. Blight A R: Macrophages and inflammatory damage in spinal cord injury. J Neurotrauma 1: 83-91, 1992.

124. Popovich P G, Stokes B T, Whitacre C C: Concept of autoimmunity following spinal cord injury: possible roles for T lymphocytes in the traumatized central nervous system J Neurosci Res 45: 349-363, 1996.

125. Szabo C, Virag L, Cuzzocrea S, Scott G S, Hake P, O'Connor M P, Zingarelli B, Salzman A, Kun E: Protection against peroxynitrite-induced fibroblast injury and arthritis development by inhibition of poly (ADP-ribose) synthetase. Proc Natl Acad Sci USA 95: 3867-3872., 1998.

126. Sribnick E A, Wingrave J M, Matzelle D D, Ray S K, Banik N L: Estrogen as a neuroprotective agent in the treatment of spinal cord injury. Ann N Y Acad Sci 993: 125-133, 2003.

127. Matejuk A, Bakke A C, Hopke C, Dwyer J, Vandenbark A A, Offner H: Estrogen treatment induces a novel population of regulatory cells, which suppresses experimental autoimmune encephalomyelitis. J Neurosci Res 77: 119-126, 2004.

128. Palaszynski K M, Liu H, Loo K K, Voskuhl R R: Estriol treatment ameliorates disease in males with experimental autoimmune encephalomyelitis: implications for multiple sclerosis. J Neuroimmunol 149: 84-89, 2004.

129. Sribnick A, Wingrave J M, Matzelle D D, Wilford G G, Ray S K, Banik N L: Estrogen attenuated markers of inflammation and decreased lesion volume in acute spinal cord injury in rats. J Neurosci Res 82: 283-293, 2005.

130. Vegeto S, Ghisletti C, Meda S, Etteri S, Belcredito S, Maggi A: Regulation of the lipopolysaccharide signal transduction pathway by 17beta-estradiol in macrophage cells. J Steroid Biochem Mol Biol 91: 59-66, 2004.

131. Genovese T, Mazzon E, Menegazzi M, Di Paola R, Muia C, Crisafulli C, Bramanti P, Suzuki H, Cuzzocrea S: Neuroprotection and enhanced recovery with hypericum perforatum extract after experimental spinal cord injury in mice. Shock 25: 608-6 17, 2006

132. Cuzzocrea S, Santagati S, Sautebin L, Mazzon E, Calabro G, Serraino I, Caputi A P, Maggi A: 17beta-estradiol antiinflammatory activity in carrageenan-induced pleurisy. Endocrinology 141: 1455-1463, 2000

133. Yune T Y, Kim S J, Lee S M, Lee Y K, Oh Y J, Kim Y C, Markelonis G J, Oh T H: Systemic administration of 17beta-estradiol reduces apoptotic cell death and improves functional recovery following traumatic spinal cord injury in rats. J Neurotrauma 21: 293-306, 2004

134. Sirin B H, Ortac R, Cerrahoglu M, Saribulbul O, Baltalarli A, Celebisoy N, Iskesen I, Rendeci O: Ischaemic preconditioning reduces spinal cord injury in transient ischaemia. Acta Cardiol 57: 279-285, 2002

135. Basso D M, Beattie M S, Bresnahan J C: A sensitive and reliable locomotor rating scale for open field testing in rats. J Neurotrauma 12: 1-2 1, 1995

136. Joshi M, Fehlings M G Development and characterization of a novel, graded model of clip compressive spinal cord injury in the mouse: Part 1. Clip design, behavioral outcomes, and histopathology. J Neurotrauma 19: 175-190, 2002a 137. 17. Joshi M, Fehlings M G Development and characterization of a novel, graded model of clip compressive spinal cord injury in the mouse: Part 2. Quantitative neuroanatomical assessment and analysis of the relationships between axonal tracts, residual tissue, and locomotor recovery. J Neurotrauma 19: 19 1-203, 2002b 138. Shea T B Technical report. An inexpensive densitometric analysis system using a Macintosh computer and a desktop scanner. Biotechniques 16: 1126-1128, 1994

139. Yamanishi Y, Boyle D L, Pinkoski M J, Mahboubi A, Lin T, Han Z, Zvaifler N J., Green D R, Firestein G S: Regulation of joint destruction and inflammation by p53 in collagen-induced arthritis. Am J Pathol 160: 123-130, 2002

140. Mullane K M, Kraemer R, Smith B: Myeloperoxidase activity as a quantitative assessment of neutrophil infiltration into ischemic myocardium. J Pharmacol Meth 14: 157-167, 1985

141. Hsu C Y, Hogan E L, Gadsden R H Jr, Spicer K M, Shi M P, Cox R D: Vascular permeability in experimental spinal cord injury. J Neurol Sci 70: 275-282, 1985

142. McTigue D M, Popovich P G, Jakeman L B, Stokes B T: Strategies for spinal cord injury repair. Prog Brain Res 128: 3-8, 2000

143. Maier B, Lehnert M, Laurer H L, Mautes A E, Steudel W I, Marzi I: Delayed elevation of soluble tumor necrosis factor receptors p75 and p55 in cerebrospinal fluid and plasma after traumatic brain injury. Shock 26: 122-127, 2006

144. Genovese T, Mazzon E, Crisafulli C, Di Paola R, Muia C, Bramanti P, Cuzzocrea S Immunomodulatory effects of etanercept in an experimental model of spinal cord injury. J Pharmacol Exp Ther 316: 1006-1016, 2005

145. Matsuyama Y, Sato K, Kamiya M, Yano J, Iwata H, Isobe K: Nitric oxide: a possible etiologic factor in spinal cord cavitation. J Spinal Disord 11: 248-252, 1998

146. Tonai T, Taketani Y, Ueda N, Nishisho T, Ohmoto Y, Sakata Y, Muraguchi M, Wada K, Yamamoto S: Possible involvement of interleukin-1 in cyclooxygenase-2 induction after spinal cord injury in rats. J Neurochem 72: 302-309, 1999

147. Beiche F, Brune K, Geisslinger G, Goppelt-Struebe M: Expression of cyclooxygenase isoforms in the rat spinal cord and their regulation during adjuvant-induced arthritis. Inflamm Res 47: 482-487, 1998

148. Vanegas H, Schaible H G: Prostaglandins and cyclooxygenases [correction of cycloxygenases] in the spinal cord. Prog Neurobiol 64: 327-63, 2001

149. Sairanen T, Ristimäki A, Karjalainen-Lindsberg M-L, Paetau A, Kaste M, Lindsberg P J: Cyclooxygenase-2 is induced globally in infarcted human brain. Ann Neurol 43: 738-747, 1998

150. Xu J, Kim G M, Chen S, Yan P, Ahmed S H, Ku G, Beckman J S, Xu X M, Hsu C Y: iNOS and nitrotyrosine expression after spinal cord injury. J Neurotrauma 18: 523-532, 2001

151. Beckman J S: Oxidative damage and tyrosine nitration from peroxynitrite. Chem Res Toxicol 9: 866-844, 1996

152. Endoh M, Maiese K, Wagner J: Expression of the inducible form of nitric oxide synthase by reactive astrocytes after transient global ischemia. Brain Res 651: 92-100, 1994

153. Merrill J E, Ignarro L J, Sherman M P, Melinek J, Lane T E: Microglial cell cytotoxicity of oligodendrocytes is mediated through nitric oxide. J Immunol 151: 2132-2141, 1993

154. Chittenden T, Harrington E A, O'Connor R, Flemington C, Lutz R J, Evan G I, Guild B C: Induction of apoptosis by the Bcl-2 homologue Bak. Nature 374: 733-736, 1995

155. Nesic-Taylor O, Cittelly D, Ye Z, Xu G Y, Unabia G, Lee J C, Svrakic N M, Liu X H, Youle R J, Wood T G, McAdoo D, Westlund K N, Hulsebosch C E, Perez-Polo J R: Exogenous BclxL fusion protein spares neurons after spinal cord injury. J Neurosci Res 79: 628-637, 2005

What is claimed is:

1. A method of ameliorating one or more effects of a traumatic injury in a human subject, the method comprising administering to the human subject, a single estrogen, wherein the estrogen is administered at between 0.3 and 3.0 mg/kg body weight and is in a water-soluble form, wherein the volume of the water-soluble form of the single estrogen is 0.5 ml/kg of body weight or less, wherein the single estrogen is administered at least one minute prior to fluid resuscitation, and wherein the traumatic injury involves severe blood loss.

2. The method of claim 1, wherein the administration is intravenous or intraosseous.

3. The method of claim 1, wherein the estrogen is ethinyl estradiol or 17β-estradiol sulfate.

4. The method of claim 1, wherein the traumatic injury involves an inflammatory response.

5. The method of claim 1, wherein the traumatic injury involves low blood pressure compared to a control blood pressure.

6. The method of claim 1, wherein the severe blood loss comprises 40% or more blood loss from the subject.

7. The method of claim 1, wherein administration of estrogen maintains a state of permissive hypotension.

8. The method of claim 1, wherein the estrogen is administered after the traumatic injury but prior to treatment.

9. A method of ameliorating one or more effects of severe blood loss in a subject, the method comprising administering to the human subject, a single estrogen, wherein the estrogen is administered at between 0.3 and 3.0 mg/kg body weight and is in water-soluble form, wherein the volume of the water-soluble form of the single estrogen is 0.5 ml/kg of body weight or less, wherein the single estrogen is administered prior to fluid resuscitation.

10. The method of claim 9, wherein the administration is intravenous or intraosseous.

11. The method of claim 9, wherein the estrogen is ethinyl estradiol or 17β-stradiol sulfate.

12. The method of claim 9, wherein the severe blood loss comprises 40% or more blood loss from the subject.

13. The method of claim 9, wherein the severe blood loss comprises 50% or more blood loss from the subject.

14. The method of claim 9, wherein the severe blood loss comprises 60% or more blood loss from the subject.

15. The method of claim 9, wherein the estrogen is administered after the severe blood loss but prior to treatment.

16. The method of claim 1, wherein the estrogen comprises 17β-estradiol sulfate.

17. The method of claim 1, wherein the estrogen is administered at 0.5 mg/kg body weight.

18. The method of claim 9, wherein the estrogen is administered at between 0.3 and 3.0 mg/kg body weight.

19. The method of claim 9, wherein the estrogen is administered at 0.5 mg/kg body weight.

20. The method of claim 1, wherein the estrogen is administered at 1 mg/kg body weight.

21. The method of claim 18, wherein the estrogen is administered at 1 mg/kg body weight.

22. The method of claim 1, wherein the single estrogen is administered at least 10 minutes prior to fluid resuscitation.

\* \* \* \* \*